(12) United States Patent
Finlay

(10) Patent No.: US 11,779,723 B2
(45) Date of Patent: Oct. 10, 2023

(54) CONNECTOR FOR POSITIONING AND STABILISING STRUCTURE

(71) Applicant: RESMED PTY LTD, Bella Vista (AU)

(72) Inventor: Iain McNicol Finlay, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/796,615

(22) PCT Filed: Jan. 28, 2021

(86) PCT No.: PCT/AU2021/050049
§ 371 (c)(1),
(2) Date: Jul. 29, 2022

(87) PCT Pub. No.: WO2021/151148
PCT Pub. Date: Aug. 5, 2021

(65) Prior Publication Data
US 2023/0061582 A1  Mar. 2, 2023

(30) Foreign Application Priority Data

Jan. 29, 2020  (AU) .............................. 2020900227

(51) Int. Cl.
*A61M 16/06* (2006.01)
*A61M 16/08* (2006.01)

(52) U.S. Cl.
CPC .... *A61M 16/0616* (2014.02); *A61M 16/0683* (2013.01); *A61M 16/0816* (2013.01); *A61M 16/0875* (2013.01)

(58) Field of Classification Search
CPC .......... A01K 1/0613; A42B 1/02; A42B 1/04; A42B 3/0406; A42B 3/20; A42B 3/288;
(Continued)

(56) References Cited

U.S. PATENT DOCUMENTS 2,867,812 A * 1/1959 Roth .................... A62B 18/084
 2/9
2,942,602 A * 6/1960 Seeler .................. A62B 18/084
 74/503
(Continued)

FOREIGN PATENT DOCUMENTS

EP  2 022 528 A2  11/2009
WO  WO 98/004310 A1  2/1998
(Continued)

OTHER PUBLICATIONS

"Respiratory Physiology", by John B. West, Lippincott Williams & Wilkins, 9th edition published 2012, 8 pages.
(Continued)

*Primary Examiner* — Annette Dixon
(74) *Attorney, Agent, or Firm* — Nixon & Vanderhye P.C.

(57) ABSTRACT

A patient interface comprising a plenum chamber pressurisable to a therapeutic pressure, a seal-forming structure constructed and arranged to maintain said therapeutic pressure in the plenum chamber, a positioning and stabilising structure to provide a force to hold a seal-forming structure in a therapeutically effective position on a patients head. The positioning and stabilising structure comprising at least one arm configured to be positioned adjacent to a cheek of the patient, and a strap removably received around the arm and configured to contact a posterior region of the patients head. The strap comprising a first coupling having a mechanical connector that is configured to engage the arm and limit movement of the arm into and out of the cavity, a second coupling spaced apart from an outer surface of the first coupling, and a sleeve being folded over the second coupling and positioned between the first and second couplings.

23 Claims, 36 Drawing Sheets

(58) Field of Classification Search
CPC .... A44B 11/266; A61F 5/3707; A61M 16/06; A61M 16/0605; A61M 16/0622; A61M 16/0633; A61M 16/0666; A61M 16/0672; A61M 16/0683; A61M 16/0816; A61M 16/0825; A61M 16/127; A61M 2210/0618; A62B 18/00; A62B 18/084; B68B 5/06; E05B 69/00; F16B 19/00; F16B 2/16; F16B 2/18; F16G 11/10; F16G 11/101; F16G 11/105; F16G 11/106; F16G 11/108; Y10S 24/44; Y10S 24/48; Y10T 24/45063; Y10T 24/45215; Y10T 24/45461; Y10T 24/45476; Y10T 24/45534; Y10T 24/4589; Y10T 24/50; Y10T 292/444; Y10T 74/20468

See application file for complete search history.

(56) References Cited

U.S. PATENT DOCUMENTS

| | | | | |
|---|---|---|---|---|
| 3,035,573 | A | * | 5/1962 | Morton, Jr. .......... A62B 18/084 2/6.2 |
| 3,040,741 | A | * | 6/1962 | Carolan ............... A62B 18/084 128/207.11 |
| 3,065,747 | A | * | 11/1962 | Forkel .................. A62B 18/084 128/201.24 |
| 3,095,876 | A | * | 7/1963 | Meister ................ A62B 18/084 2/9 |
| 3,513,841 | A | * | 5/1970 | Seeler .................. A62B 18/084 128/201.23 |
| 4,136,403 | A | * | 1/1979 | Walther ................ A42B 3/288 2/10 |
| 4,782,832 | A | | 11/1988 | Trimble et al. |
| 4,848,334 | A | * | 7/1989 | Bellm .................. A61M 16/06 D24/110.4 |
| 4,869,245 | A | * | 9/1989 | Nowakowski ....... A62B 18/084 2/422 |
| 4,944,310 | A | | 7/1990 | Sullivan |
| 5,441,046 | A | * | 8/1995 | Starr .................. A61M 16/0683 128/207.11 |
| 5,675,875 | A | * | 10/1997 | Servatius ............... F16B 19/00 2/9 |
| 5,687,715 | A | | 11/1997 | Landis |
| 6,532,959 | B1 | | 3/2003 | Berthon-Jones |
| 6,581,594 | B1 | | 6/2003 | Drew et al. |
| 7,866,944 | B2 | | 1/2011 | Kenyon et al. |
| 8,636,479 | B2 | | 1/2014 | Kenyon et al. |
| 8,638,014 | B2 | | 1/2014 | Sears et al. |
| 8,733,349 | B2 | | 5/2014 | Bath et al. |
| 9,302,065 | B2 | * | 4/2016 | Smith ............... A61M 16/0672 |
| 2009/0044808 | A1 | | 2/2009 | Guney et al. |
| 2009/0050156 | A1 | | 2/2009 | Ng et al. |
| 2010/0000534 | A1 | | 1/2010 | Kooij et al. |
| 2015/0144139 | A1 | * | 5/2015 | Lockhart .......... A61M 16/0622 128/205.25 |
| 2015/0352306 | A1 | | 12/2015 | Scheiner et al. |
| 2016/0296720 | A1 | | 10/2016 | Henry et al. |
| 2018/0140795 | A1 | | 5/2018 | Wells et al. |
| 2018/0250488 | A1 | | 9/2018 | Haskard et al. |
| 2019/0083734 | A1 | * | 3/2019 | Hammer .................. A42B 1/04 |

FOREIGN PATENT DOCUMENTS

| | | |
|---|---|---|
| WO | WO 98/034665 A1 | 8/1998 |
| WO | WO 2000/078381 A1 | 12/2000 |
| WO | WO 2004/073778 A1 | 9/2004 |
| WO | WO 2005/063328 A1 | 7/2005 |
| WO | WO 2006/074513 A1 | 7/2006 |
| WO | WO 2006/130903 A1 | 12/2006 |
| WO | 2008/011682 A1 | 1/2008 |
| WO | 2008/106716 A1 | 9/2008 |
| WO | WO 2009/052560 A1 | 4/2009 |
| WO | WO 2010/135785 A1 | 12/2010 |
| WO | 2011/110962 A1 | 9/2011 |
| WO | WO 2012/171072 A1 | 12/2012 |
| WO | WO 2013/020167 A1 | 2/2013 |
| WO | 2014/015382 A1 | 1/2014 |
| WO | 2014/025267 A1 | 2/2014 |
| WO | 2014/110626 A1 | 7/2014 |
| WO | 2016/193859 A1 | 12/2016 |
| WO | 2017/124152 A1 | 7/2017 |
| WO | 2018/176094 A1 | 10/2018 |
| WO | 2020/157559 A1 | 8/2020 |
| WO | 2020/188495 A1 | 9/2020 |
| WO | 2021/012005 A1 | 1/2021 |
| WO | 2021/046605 A1 | 3/2021 |

OTHER PUBLICATIONS

International Search Report dated May 12, 2021 in International Application No. PCT/AU2021/050049, 24 pages.

Written Opinion of the International Searching Authority dated May 12, 2021 in International Application No. PCT/AU2021/050049, 10 pages.

International Preliminary Report on Patentability dated Jul. 28, 2022 issued in International Application No. PCT/AU2021/050049 (11 pages).

* cited by examiner

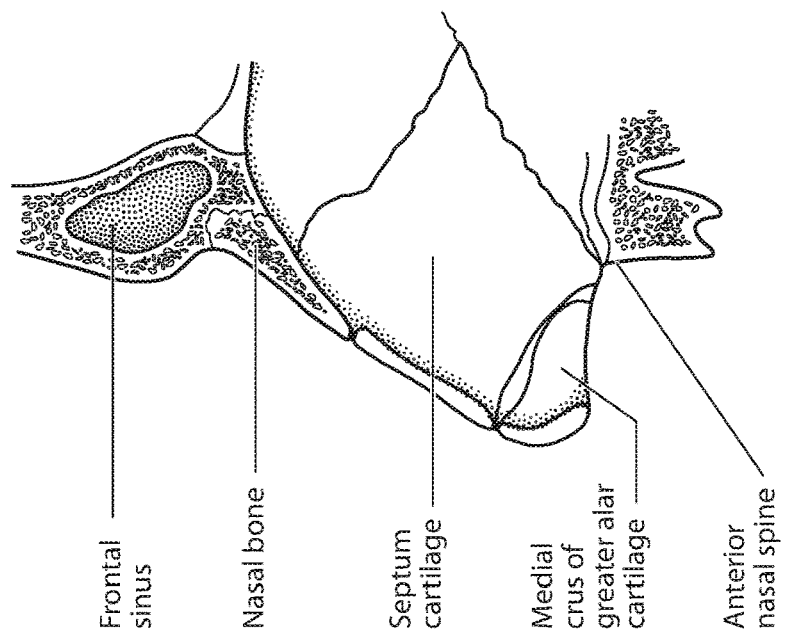
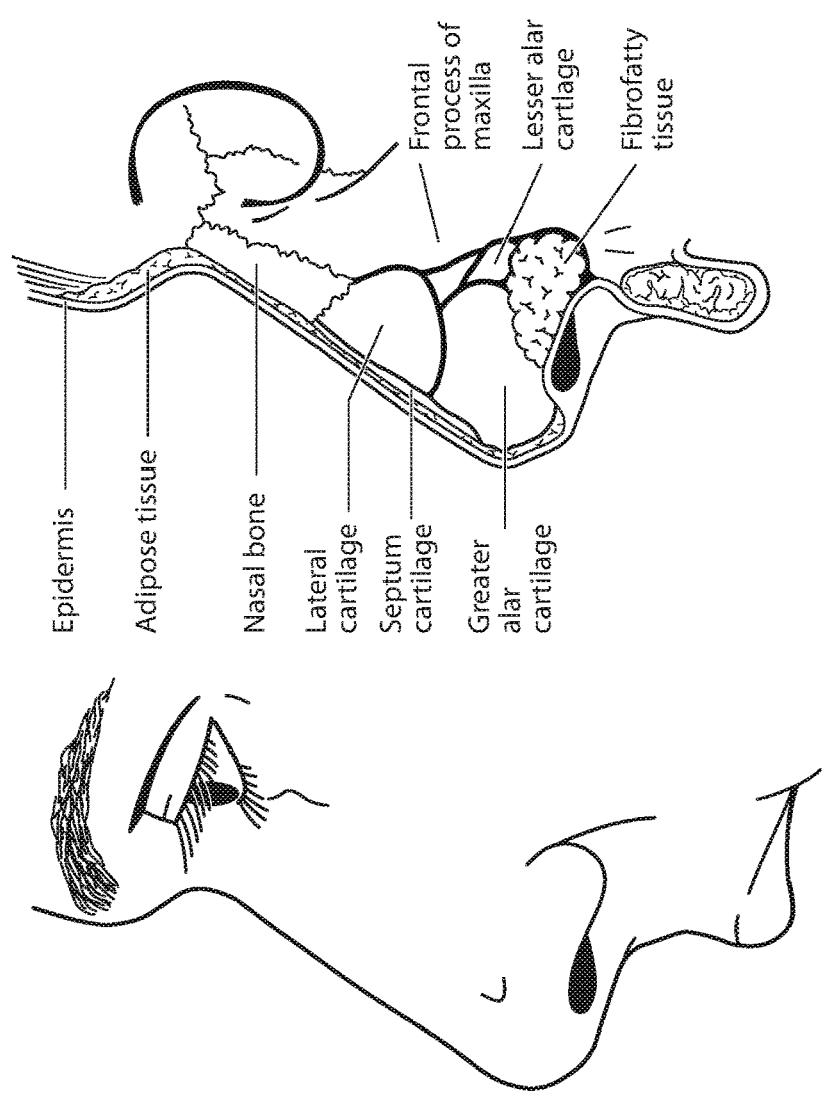
FIG. 2G  FIG. 2H  FIG. 2I

Relatively Large Positive Curvature

Relatively Small Positive Curvature

Zero Curvature

Relatively Small Negative Curvature

Relatively Large Negative Curvature

Copyright 2015 ResMed Limited

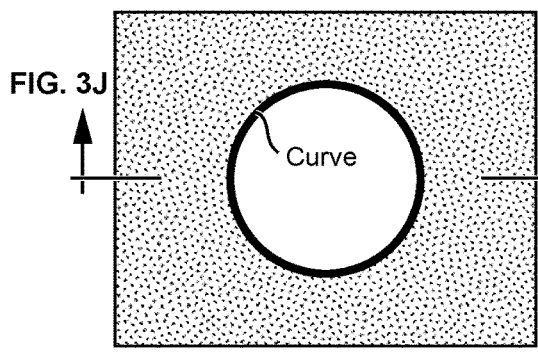
FIG. 3I
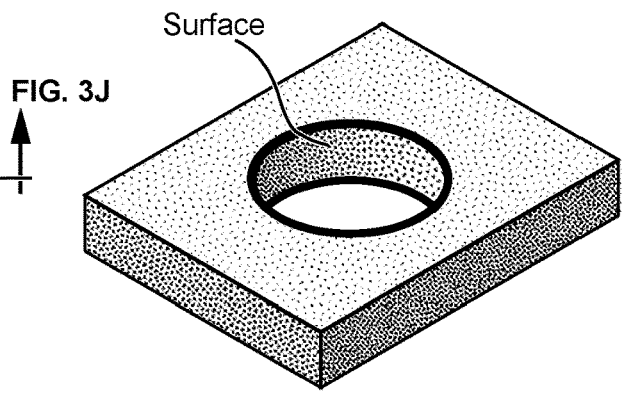
FIG. 3K
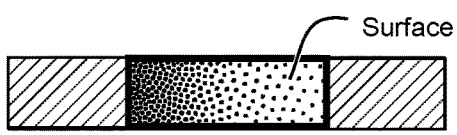
FIG. 3J
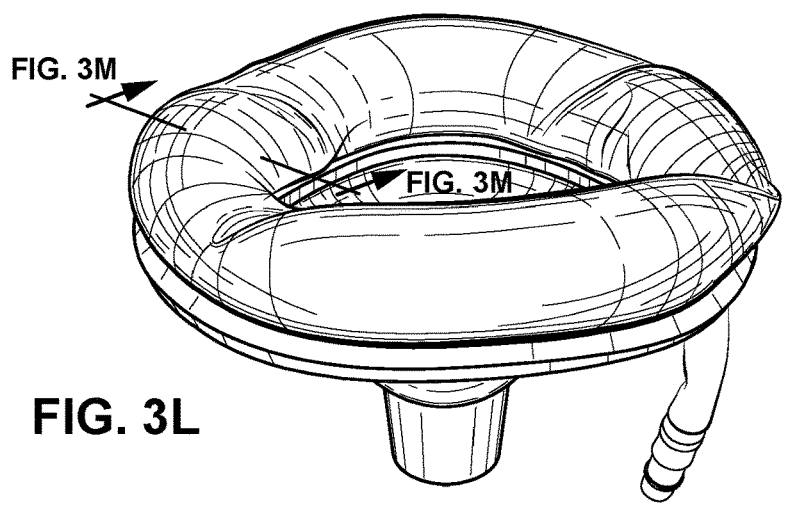
FIG. 3L
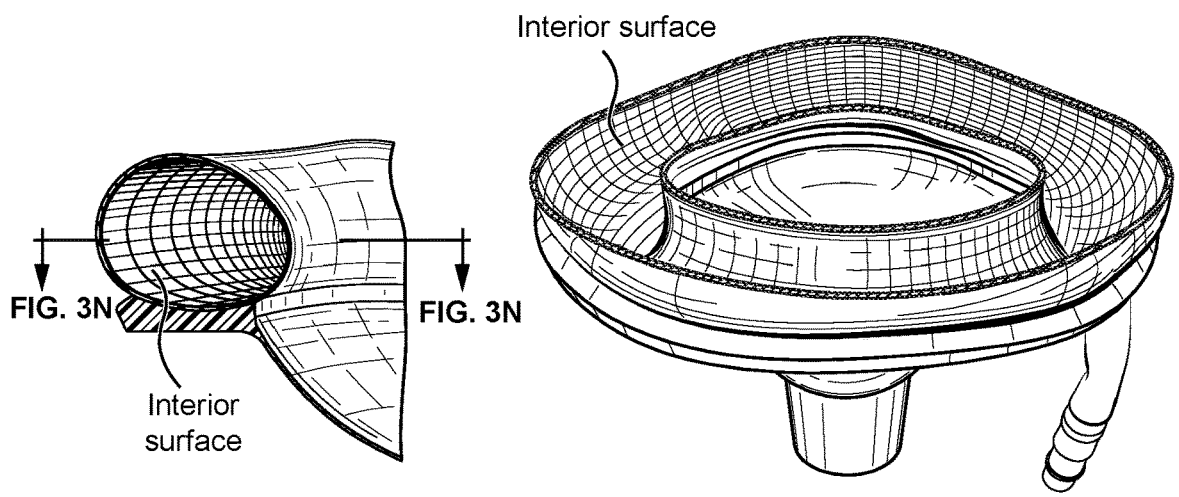
FIG. 3M     FIG. 3N
Copyright 2015 ResMed Limited

Left-hand rule  Right-hand rule
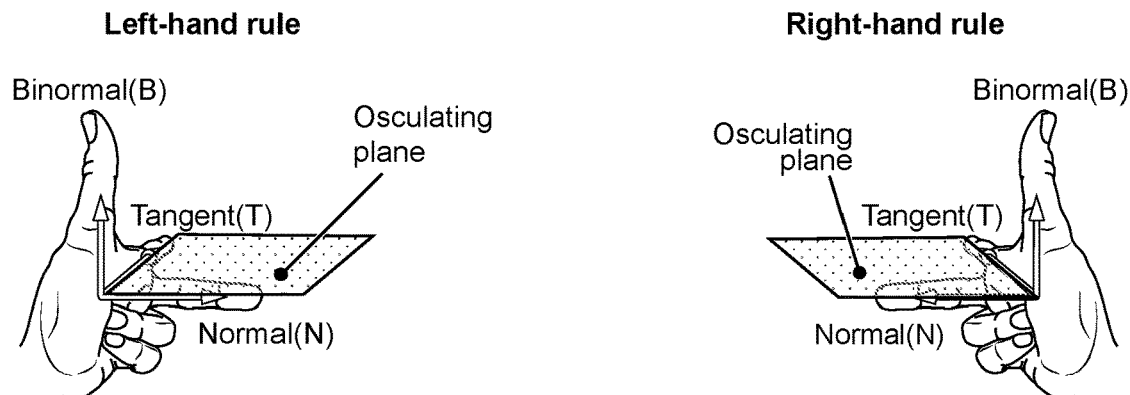
FIG. 3O  FIG. 3P
Left ear helix  Right ear helix
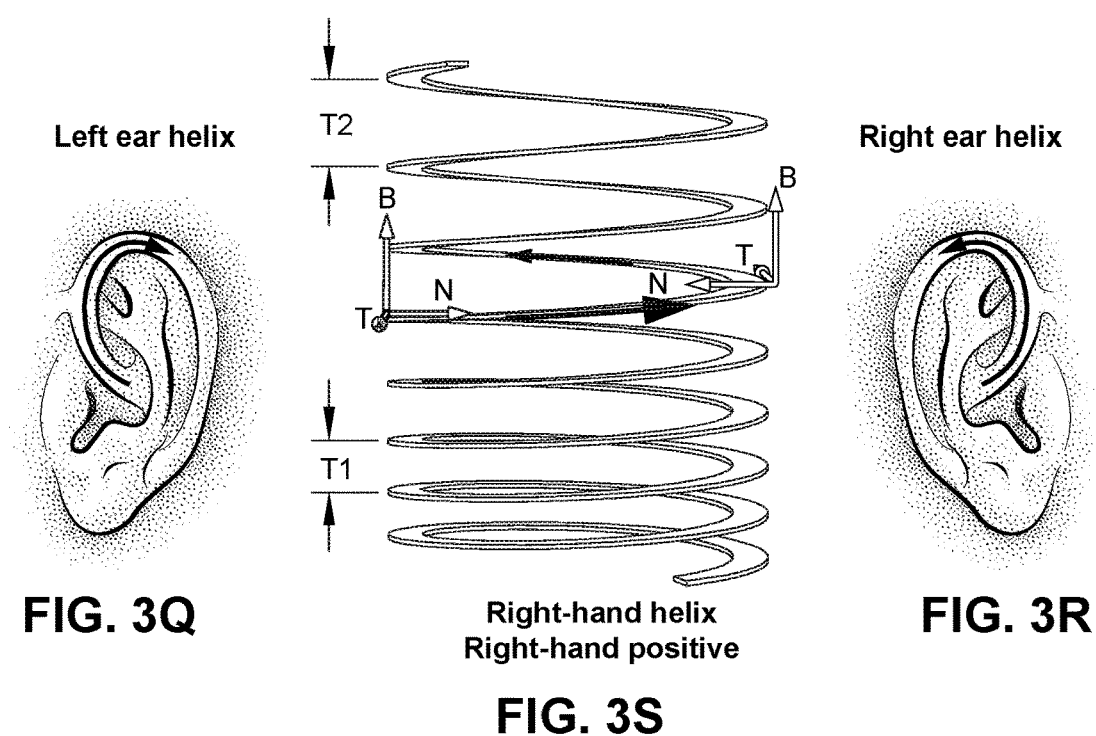
FIG. 3Q  
Right-hand helix  
Right-hand positive  
FIG. 3R
FIG. 3S
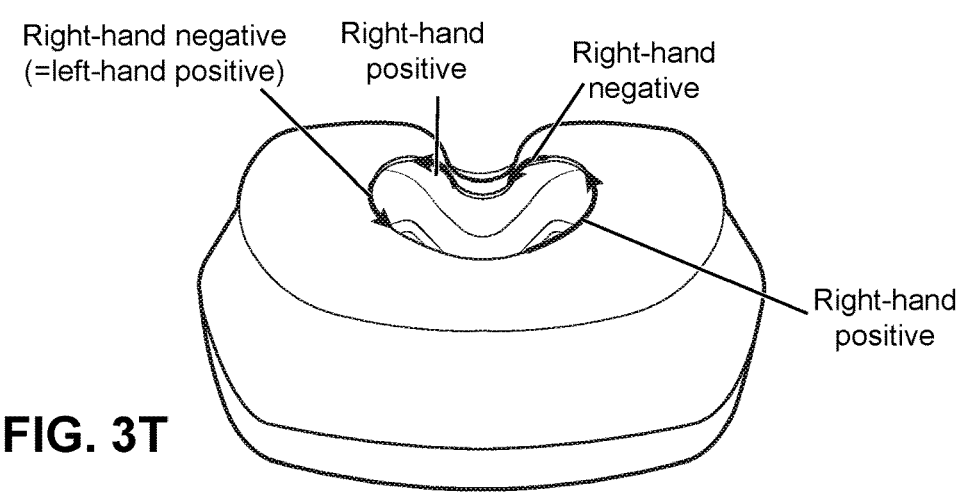
FIG. 3T
Copyright 2015 ResMed Limited

CONNECTOR FOR POSITIONING AND STABILISING STRUCTURE

1 CROSS-REFERENCE TO RELATED APPLICATIONS

This application is the U.S. national phase of International Application No. PCT/AU2021/050049 filed Jan. 28, 2021 which designated the U.S. and claims priority to Australian Provisional Application No. 2020900227 filed Jan. 29, 2020, the entire contents of each of which are hereby incorporated by reference.

2 BACKGROUND OF THE TECHNOLOGY

2.1 Field of the Technology

The present technology relates to one or more of the screening, diagnosis, monitoring, treatment, prevention and amelioration of respiratory-related disorders. The present technology also relates to medical devices or apparatus, and their use.

2.2 Description of the Related Art 2.2.1 Human Respiratory System and its Disorders The respiratory system of the body facilitates gas exchange. The nose and mouth form the entrance to the airways of a patient.

The airways include a series of branching tubes, which become narrower, shorter and more numerous as they penetrate deeper into the lung. The prime function of the lung is gas exchange, allowing oxygen to move from the inhaled air into the venous blood and carbon dioxide to move in the opposite direction. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See "*Respiratory Physiology*", by John B. West, Lippincott Williams & Wilkins, 9th edition published 2012.

A range of respiratory disorders exist. Certain disorders may be characterised by particular events, e.g. apneas, hypopneas, and hyperpneas.

Examples of respiratory disorders include Obstructive Sleep Apnea (OSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD) and Chest wall disorders.

Obstructive Sleep Apnea (OSA), a form of Sleep Disordered Breathing (SDB), is characterised by events including occlusion or obstruction of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds in duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Respiratory failure is an umbrella term for respiratory disorders in which the lungs are unable to inspire sufficient oxygen or exhale sufficient $CO_2$ to meet the patient's needs. Respiratory failure may encompass some or all of the following disorders.

A patient with respiratory insufficiency (a form of respiratory failure) may experience abnormal shortness of breath on exercise.

A range of therapies have been used to treat or ameliorate such conditions. Furthermore, otherwise healthy individuals may take advantage of such therapies to prevent respiratory disorders from arising. However, these have a number of shortcomings.

2.2.2 Therapies

Various respiratory therapies, such as Continuous Positive Airway Pressure (CPAP) therapy, Non-invasive ventilation (NIV), Invasive ventilation (IV), and High Flow Therapy (HFT) have been used to treat one or more of the above respiratory disorders.

2.2.2.1 Respiratory Pressure Therapies

Respiratory pressure therapy is the application of a supply of air to an entrance to the airways at a controlled target pressure that is nominally positive with respect to atmosphere throughout the patient's breathing cycle (in contrast to negative pressure therapies such as the tank ventilator or cuirass).

Continuous Positive Airway Pressure (CPAP) therapy has been used to treat Obstructive Sleep Apnea (OSA). The mechanism of action is that continuous positive airway pressure acts as a pneumatic splint and may prevent upper airway occlusion, such as by pushing the soft palate and tongue forward and away from the posterior oropharyngeal wall. Treatment of OSA by CPAP therapy may be voluntary, and hence patients may elect not to comply with therapy if they find devices used to provide such therapy one or more of: uncomfortable, difficult to use, expensive and aesthetically unappealing.

2.2.2.2 Flow Therapies

Not all respiratory therapies aim to deliver a prescribed therapeutic pressure. Some respiratory therapies aim to deliver a prescribed respiratory volume, by delivering an inspiratory flow rate profile over a targeted duration, possibly superimposed on a positive baseline pressure. In other cases, the interface to the patient's airways is 'open' (unsealed) and the respiratory therapy may only supplement the patient's own spontaneous breathing with a flow of conditioned or enriched gas. In one example, High Flow therapy (HFT) is the provision of a continuous, heated, humidified flow of air to an entrance to the airway through an unsealed or open patient interface at a "treatment flow rate" that is held approximately constant throughout the respiratory cycle. The treatment flow rate is nominally set to exceed the patient's peak inspiratory flow rate. HFT has been used to treat OSA, CSR, respiratory failure, COPD, and other respiratory disorders. One mechanism of action is that the high flow rate of air at the airway entrance improves ventilation efficiency by flushing, or washing out, expired $CO_2$ from the patient's anatomical deadspace. Hence, HFT is thus sometimes referred to as a deadspace therapy (DST). Other benefits may include the elevated warmth and humidification (possibly of benefit in secretion management) and the potential for modest elevation of airway pressures. As an alternative to constant flow rate, the treatment flow rate may follow a profile that varies over the respiratory cycle.

Another form of flow therapy is long-term oxygen therapy (LTOT) or supplemental oxygen therapy. Doctors may prescribe a continuous flow of oxygen enriched air at a specified oxygen concentration (from 21%, the oxygen fraction in ambient air, to 100%) at a specified flow rate (e.g., 1 litre per minute (LPM), 2 LPM, 3 LPM, etc.) to be delivered to the patient's airway.

2.2.2.3 Supplementary Oxygen

For certain patients, oxygen therapy may be combined with a respiratory pressure therapy or HFT by adding supplementary oxygen to the pressurised flow of air. When oxygen is added to respiratory pressure therapy, this is referred to as RPT with supplementary oxygen. When oxygen is added to HFT, the resulting therapy is referred to as HFT with supplementary oxygen.

2.2.3 Respiratory Therapy Systems

These respiratory therapies may be provided by a respiratory therapy system or device. Such systems and devices may also be used to screen, diagnose, or monitor a condition without treating it.

A respiratory therapy system may comprise a Respiratory Pressure Therapy Device (RPT device), an air circuit, a humidifier, a patient interface, an oxygen source, and data management.

2.2.3.1 Patient Interface

A patient interface may be used to interface respiratory equipment to its wearer, for example by providing a flow of air to an entrance to the airways. The flow of air may be provided via a mask to the nose and/or mouth, a tube to the mouth or a tracheostomy tube to the trachea of a patient. Depending upon the therapy to be applied, the patient interface may form a seal, e.g., with a region of the patient's face, to facilitate the delivery of gas at a pressure at sufficient variance with ambient pressure to effect therapy, e.g., at a positive pressure of about 10 cmH$_2$O relative to ambient pressure. For other forms of therapy, such as the delivery of oxygen, the patient interface may not include a seal sufficient to facilitate delivery to the airways of a supply of gas at a positive pressure of about 10 cmH$_2$O. For flow therapies such as nasal HFT, the patient interface is configured to insufflate the nares but specifically to avoid a complete seal. One example of such a patient interface is a nasal cannula.

Certain other mask systems may be functionally unsuitable for the present field. For example, purely ornamental masks may be unable to maintain a suitable pressure. Mask systems used for underwater swimming or diving may be configured to guard against ingress of water from an external higher pressure, but not to maintain air internally at a higher pressure than ambient.

Certain masks may be clinically unfavourable for the present technology e.g. if they block airflow via the nose and only allow it via the mouth.

Certain masks may be uncomfortable or impractical for the present technology if they require a patient to insert a portion of a mask structure in their mouth to create and maintain a seal via their lips.

Certain masks may be impractical for use while sleeping, e.g. for sleeping while lying on one's side in bed with a head on a pillow.

The design of a patient interface presents a number of challenges. The face has a complex three-dimensional shape. The size and shape of noses and heads varies considerably between individuals. Since the head includes bone, cartilage and soft tissue, different regions of the face respond differently to mechanical forces. The jaw or mandible may move relative to other bones of the skull. The whole head may move during the course of a period of respiratory therapy.

As a consequence of these challenges, some masks suffer from being one or more of obtrusive, aesthetically undesirable, costly, poorly fitting, difficult to use, and uncomfortable especially when worn for long periods of time or when a patient is unfamiliar with a system. Wrongly sized masks can give rise to reduced compliance, reduced comfort and poorer patient outcomes. Masks designed solely for aviators, masks designed as part of personal protection equipment (e.g. filter masks), SCUBA masks, or for the administration of anaesthetics may be tolerable for their original application, but nevertheless such masks may be undesirably uncomfortable to be worn for extended periods of time, e.g., several hours. This discomfort may lead to a reduction in patient compliance with therapy. This is even more so if the mask is to be worn during sleep.

CPAP therapy is highly effective to treat certain respiratory disorders, provided patients comply with therapy. If a mask is uncomfortable, or difficult to use a patient may not comply with therapy. Since it is often recommended that a patient regularly wash their mask, if a mask is difficult to clean (e.g., difficult to assemble or disassemble), patients may not clean their mask and this may impact on patient compliance.

While a mask for other applications (e.g. aviators) may not be suitable for use in treating sleep disordered breathing, a mask designed for use in treating sleep disordered breathing may be suitable for other applications.

For these reasons, patient interfaces for delivery of CPAP during sleep form a distinct field.

2.2.3.1.1 Seal-Forming Structure

Patient interfaces may include a seal-forming structure. Since it is in direct contact with the patient's face, the shape and configuration of the seal-forming structure can have a direct impact the effectiveness and comfort of the patient interface.

A patient interface may be partly characterised according to the design intent of where the seal-forming structure is to engage with the face in use. In one form of patient interface, a seal-forming structure may comprise a first sub-portion to form a seal around the left naris and a second sub-portion to form a seal around the right naris. In one form of patient interface, a seal-forming structure may comprise a single element that surrounds both nares in use. Such single element may be designed to for example overlay an upper lip region and a nasal bridge region of a face. In one form of patient interface a seal-forming structure may comprise an element that surrounds a mouth region in use, e.g. by forming a seal on a lower lip region of a face. In one form of patient interface, a seal-forming structure may comprise a single element that surrounds both nares and a mouth region in use. These different types of patient interfaces may be known by a variety of names by their manufacturer including nasal masks, full-face masks, nasal pillows, nasal puffs and oro-nasal masks.

A seal-forming structure that may be effective in one region of a patient's face may be inappropriate in another region, e.g. because of the different shape, structure, variability and sensitivity regions of the patient's face. For example, a seal on swimming goggles that overlays a patient's forehead may not be appropriate to use on a patient's nose.

Certain seal-forming structures may be designed for mass manufacture such that one design fit and be comfortable and effective for a wide range of different face shapes and sizes. To the extent to which there is a mismatch between the shape of the patient's face, and the seal-forming structure of the mass-manufactured patient interface, one or both must adapt in order for a seal to form.

One type of seal-forming structure extends around the periphery of the patient interface, and is intended to seal against the patient's face when force is applied to the patient interface with the seal-forming structure in confronting engagement with the patient's face. The seal-forming structure may include an air or fluid filled cushion, or a moulded or formed surface of a resilient seal element made of an elastomer such as a rubber. With this type of seal-forming structure, if the fit is not adequate, there will be gaps between the seal-forming structure and the face, and additional force will be required to force the patient interface against the face in order to achieve a seal.

Another type of seal-forming structure incorporates a flap seal of thin material positioned about the periphery of the mask so as to provide a self-sealing action against the face of the patient when positive pressure is applied within the mask. Like the previous style of seal forming portion, if the match between the face and the mask is not good, additional force may be required to achieve a seal, or the mask may leak. Furthermore, if the shape of the seal-forming structure does not match that of the patient, it may crease or buckle in use, giving rise to leaks.

Another type of seal-forming structure may comprise a friction-fit element, e.g. for insertion into a naris, however some patients find these uncomfortable.

Another form of seal-forming structure may use adhesive to achieve a seal. Some patients may find it inconvenient to constantly apply and remove an adhesive to their face.

A range of patient interface seal-forming structure technologies are disclosed in the following patent applications, assigned to ResMed Limited: WO 1998/004,310; WO 2006/074,513; WO 2010/135,785.

One form of nasal pillow is found in the Adam Circuit manufactured by Puritan Bennett. Another nasal pillow, or nasal puff is the subject of U.S. Pat. No. 4,782,832 (Trimble et al.), assigned to Puritan-Bennett Corporation.

ResMed Limited has manufactured the following products that incorporate nasal pillows: SWIFT™ nasal pillows mask, SWIFT™ II nasal pillows mask, SWIFT™ LT nasal pillows mask, SWIFT™ FX nasal pillows mask and MIRAGE LIBERTY™ full-face mask. The following patent applications, assigned to ResMed Limited, describe examples of nasal pillows masks: International Patent Application WO2004/073,778 (describing amongst other things aspects of the ResMed Limited SWIFT™ nasal pillows), US Patent Application 2009/0044808 (describing amongst other things aspects of the ResMed Limited SWIFT™ LT nasal pillows); International Patent Applications WO 2005/063,328 and WO 2006/130,903 (describing amongst other things aspects of the ResMed Limited MIRAGE LIBERTY™ full-face mask); International Patent Application WO 2009/052,560 (describing amongst other things aspects of the ResMed Limited SWIFT™ FX nasal pillows).

2.2.3.1.2 Positioning and Stabilising

A seal-forming structure of a patient interface used for positive air pressure therapy is subject to the corresponding force of the air pressure to disrupt a seal. Thus a variety of techniques have been used to position the seal-forming structure, and to maintain it in sealing relation with the appropriate portion of the face.

One technique is the use of adhesives. See for example US Patent Application Publication No. US 2010/0000534. However, the use of adhesives may be uncomfortable for some.

Another technique is the use of one or more straps and/or stabilising harnesses. Many such harnesses suffer from being one or more of ill-fitting, bulky, uncomfortable and awkward to use.

2.2.3.2 Respiratory Pressure Therapy (RPT) Device

A respiratory pressure therapy (RPT) device may be used individually or as part of a system to deliver one or more of a number of therapies described above, such as by operating the device to generate a flow of air for delivery to an interface to the airways. The flow of air may be pressure-controlled (for respiratory pressure therapies) or flow-controlled (for flow therapies such as HFT). Thus RPT devices may also act as flow therapy devices. Examples of RPT devices include a CPAP device and a ventilator.

Air pressure generators are known in a range of applications, e.g. industrial-scale ventilation systems. However, air pressure generators for medical applications have particular requirements not fulfilled by more generalised air pressure generators, such as the reliability, size and weight requirements of medical devices. In addition, even devices designed for medical treatment may suffer from shortcomings, pertaining to one or more of: comfort, noise, ease of use, efficacy, size, weight, manufacturability, cost, and reliability.

An example of the special requirements of certain RPT devices is acoustic noise.

Table of noise output levels of prior RPT devices (one specimen only, measured using test method specified in ISO 3744 in CPAP mode at 10 cmH$_2$O).

| RPT Device name | A-weighted sound pressure level dB(A) | Year (approx.) |
| --- | --- | --- |
| C-Series Tango ™ | 31.9 | 2007 |
| C-Series Tango ™ with Humidifier | 33.1 | 2007 |
| S8 Escape ™ II | 30.5 | 2005 |
| S8 Escape ™ II with H4i ™ Humidifier | 31.1 | 2005 |
| S9 AutoSet ™ | 26.5 | 2010 |
| S9 AutoSet ™ with H5i Humidifier | 28.6 | 2010 |

One known RPT device used for treating sleep disordered breathing is the S9 Sleep Therapy System, manufactured by ResMed Limited. Another example of an RPT device is a ventilator. Ventilators such as the ResMed Stellar™ Series of Adult and Paediatric Ventilators may provide support for invasive and non-invasive non-dependent ventilation for a range of patients for treating a number of conditions such as but not limited to NMD, OHS and COPD.

The ResMed Elisée™ 150 ventilator and ResMed VS III™ ventilator may provide support for invasive and non-invasive dependent ventilation suitable for adult or paediatric patients for treating a number of conditions. These ventilators provide volumetric and barometric ventilation modes with a single or double limb circuit. RPT devices typically comprise a pressure generator, such as a motor-driven blower or a compressed gas reservoir, and are configured to supply a flow of air to the airway of a patient. In some cases, the flow of air may be supplied to the airway of the patient at positive pressure. The outlet of the RPT device is connected via an air circuit to a patient interface such as those described above.

The designer of a device may be presented with an infinite number of choices to make. Design criteria often conflict, meaning that certain design choices are far from routine or inevitable. Furthermore, the comfort and efficacy of certain aspects may be highly sensitive to small, subtle changes in one or more parameters.

2.2.3.3 Air Circuit

An air circuit is a conduit or a tube constructed and arranged to allow, in use, a flow of air to travel between two components of a respiratory therapy system such as the RPT device and the patient interface. In some cases, there may be separate limbs of the air circuit for inhalation and exhalation. In other cases, a single limb air circuit is used for both inhalation and exhalation.

2.2.3.4 Humidifier

Delivery of a flow of air without humidification may cause drying of airways. The use of a humidifier with an RPT device and the patient interface produces humidified gas that minimizes drying of the nasal mucosa and increases patient airway comfort. In addition, in cooler climates, warm air applied generally to the face area in and about the patient interface is more comfortable than cold air.

A range of artificial humidification devices and systems are known, however they may not fulfil the specialised requirements of a medical humidifier.

Medical humidifiers are used to increase humidity and/or temperature of the flow of air in relation to ambient air when required, typically where the patient may be asleep or resting (e.g. at a hospital). A medical humidifier for bedside placement may be small. A medical humidifier may be configured to only humidify and/or heat the flow of air delivered to the patient without humidifying and/or heating the patient's surroundings. Room-based systems (e.g. a sauna, an air conditioner, or an evaporative cooler), for example, may also humidify air that is breathed in by the patient, however those systems would also humidify and/or heat the entire room, which may cause discomfort to the occupants. Furthermore, medical humidifiers may have more stringent safety constraints than industrial humidifiers While a number of medical humidifiers are known, they can suffer from one or more shortcomings. Some medical humidifiers may provide inadequate humidification, some are difficult or inconvenient to use by patients.

2.2.3.5 Data Management

There may be clinical reasons to obtain data to determine whether the patient prescribed with respiratory therapy has been "compliant", e.g. that the patient has used their RPT device according to one or more "compliance rules". One example of a compliance rule for CPAP therapy is that a patient, in order to be deemed compliant, is required to use the RPT device for at least four hours a night for at least 21 of 30 consecutive days. In order to determine a patient's compliance, a provider of the RPT device, such as a health care provider, may manually obtain data describing the patient's therapy using the RPT device, calculate the usage over a predetermined time period, and compare with the compliance rule. Once the health care provider has determined that the patient has used their RPT device according to the compliance rule, the health care provider may notify a third party that the patient is compliant.

There may be other aspects of a patient's therapy that would benefit from communication of therapy data to a third party or external system.

Existing processes to communicate and manage such data can be one or more of costly, time-consuming, and error-prone.

2.2.3.6 Mandibular Repositioning

A mandibular repositioning device (MRD) or mandibular advancement device (MAD) is one of the treatment options for sleep apnea and snoring. It is an adjustable oral appliance available from a dentist or other supplier that holds the lower jaw (mandible) in a forward position during sleep. The MRD is a removable device that a patient inserts into their mouth prior to going to sleep and removes following sleep. Thus, the MRD is not designed to be worn all of the time. The MRD may be custom made or produced in a standard form and includes a bite impression portion designed to allow fitting to a patient's teeth. This mechanical protrusion of the lower jaw expands the space behind the tongue, puts tension on the pharyngeal walls to reduce collapse of the airway and diminishes palate vibration.

In certain examples a mandibular advancement device may comprise an upper splint that is intended to engage with or fit over teeth on the upper jaw or maxilla and a lower splint that is intended to engage with or fit over teeth on the upper jaw or mandible. The upper and lower splints are connected together laterally via a pair of connecting rods. The pair of connecting rods are fixed symmetrically on the upper splint and on the lower splint.

In such a design the length of the connecting rods is selected such that when the MRD is placed in a patient's mouth the mandible is held in an advanced position. The length of the connecting rods may be adjusted to change the level of protrusion of the mandible. A dentist may determine a level of protrusion for the mandible that will determine the length of the connecting rods.

Some MRDs are structured to push the mandible forward relative to the maxilla while other MADs, such as the ResMed Narval CC™ MRD are designed to retain the mandible in a forward position. This device also reduces or minimises dental and temporo-mandibular joint (TMJ) side effects. Thus, it is configured to minimises or prevent any movement of one or more of the teeth.

2.2.3.7 Vent Technologies

Some forms of treatment systems may include a vent to allow the washout of exhaled carbon dioxide. The vent may allow a flow of gas from an interior space of a patient interface, e.g., the plenum chamber, to an exterior of the patient interface, e.g., to ambient.

The vent may comprise an orifice and gas may flow through the orifice in use of the mask. Many such vents are noisy. Others may become blocked in use and thus provide insufficient washout. Some vents may be disruptive of the sleep of a bed partner 1100 of the patient 1000, e.g. through noise or focussed airflow.

ResMed Limited has developed a number of improved mask vent technologies. See International Patent Application Publication No. WO 1998/034,665; International Patent Application Publication No. WO 2000/078,381; U.S. Pat. No. 6,581,594; US Patent Application Publication No. US 2009/0050156; US Patent Application Publication No. 2009/0044808.

Table of noise of prior masks (ISO 17510-2:2007, 10 cmH$_2$O pressure at 1 m)

| Mask name | Mask type | A-weighted sound power level dB(A) (uncertainty) | A-weighted sound pressure dB(A) (uncertainty) | Year (approx.) |
|---|---|---|---|---|
| Glue-on (*) | nasal | 50.9 | 42.9 | 1981 |
| ResCare standard (*) | nasal | 31.5 | 23.5 | 1993 |
| ResMed Mirage ™ (*) | nasal | 29.5 | 21.5 | 1998 |
| ResMed UltraMirage ™ | nasal | 36 (3) | 28 (3) | 2000 |
| ResMed Mirage Activa ™ | nasal | 32 (3) | 24 (3) | 2002 |

-continued

| Mask name | Mask type | A-weighted sound power level dB(A) (uncertainty) | A-weighted sound pressure dB(A) (uncertainty) | Year (approx.) |
|---|---|---|---|---|
| ResMed Mirage Micro ™ | nasal | 30 (3) | 22 (3) | 2008 |
| ResMed Mirage ™ SoftGel | nasal | 29 (3) | 22 (3) | 2008 |
| ResMed Mirage ™ FX | nasal | 26 (3) | 18 (3) | 2010 |
| ResMed Mirage Swift ™ (*) | nasal pillows | 37 | 29 | 2004 |
| ResMed Mirage Swift ™ II | nasal pillows | 28 (3) | 20 (3) | 2005 |
| ResMed Mirage Swift ™ LT | nasal pillows | 25 (3) | 17 (3) | 2008 |
| ResMed AirFit P10 | nasal pillows | 21 (3) | 13 (3) | 2014 |

Sound pressure values of a variety of objects are listed below

| Object | A-weighted sound pressure dB(A) | Notes |
|---|---|---|
| Vacuum cleaner: Nilfisk Walter Broadly Litter Hog: B+ Grade | 68 | ISO 3744 at 1 m distance |
| Conversational speech | 60 | 1 m distance |
| Average home | 50 | |
| Quiet library | 40 | |
| Quiet bedroom at night | 30 | |
| Background in TV studio | 20 | |

2.2.4 Screening, Diagnosis, and Monitoring Systems

Polysomnography (PSG) is a conventional system for diagnosis and monitoring of cardio-pulmonary disorders, and typically involves expert clinical staff to apply the system. PSG typically involves the placement of 15 to 20 contact sensors on a patient in order to record various bodily signals such as electroencephalography (EEG), electrocardiography (ECG), electrooculograpy (EOG), electromyography (EMG), etc. PSG for sleep disordered breathing has involved two nights of observation of a patient in a clinic, one night of pure diagnosis and a second night of titration of treatment parameters by a clinician. PSG is therefore expensive and inconvenient. In particular it is unsuitable for home screening/diagnosis/monitoring of sleep disordered breathing.

Screening and diagnosis generally describe the identification of a condition from its signs and symptoms. Screening typically gives a true/false result indicating whether or not a patient's SDB is severe enough to warrant further investigation, while diagnosis may result in clinically actionable information. Screening and diagnosis tend to be one-off processes, whereas monitoring the progress of a condition can continue indefinitely. Some screening/diagnosis systems are suitable only for screening/diagnosis, whereas some may also be used for monitoring.

Clinical experts may be able to screen, diagnose, or monitor patients adequately based on visual observation of PSG signals. However, there are circumstances where a clinical expert may not be available, or a clinical expert may not be affordable. Different clinical experts may disagree on a s condition. In addition, a given clinical expert may apply a different standard at different times.

3 BRIEF SUMMARY OF THE TECHNOLOGY

The present technology is directed towards providing medical devices used in the screening, diagnosis, monitoring, amelioration, treatment, or prevention of respiratory disorders having one or more of improved comfort, cost, efficacy, ease of use and manufacturability.

A first aspect of the present technology relates to apparatus used in the screening, diagnosis, monitoring, amelioration, treatment or prevention of a respiratory disorder.

Another aspect of the present technology relates to methods used in the screening, diagnosis, monitoring, amelioration, treatment or prevention of a respiratory disorder.

An aspect of certain forms of the present technology is to provide methods and/or apparatus that improve the compliance of patients with respiratory therapy.

One form of the present technology is directed to a patient interface that may comprise: a plenum chamber; a seal-forming structure; and a positioning and stabilising structure. The patient interface may further comprise a vent structure. The patient interface may further be configured to leave the patient's mouth uncovered, or if the seal-forming structure is configured to seal around the patient's nose and mouth, the patient interface may be further configured to allow the patient to breathe from ambient in the absence of a flow of pressurised air through the plenum chamber inlet port.

Another aspect of the present technology is directed to a face-mounted interface that may comprise: a facial interface, and a positioning and stabilising structure. The facial interface may be configured to contact a user's (such as a patient's) face. The positioning and stabilising structure structured to hold the facial interface in an effective position against the user's face.

In some aspects, the face-mounted interface is a patient interface used in screening, diagnosis, monitoring, amelioration, treatment or prevention of a respiratory disorder. However, the face-mounted interface may be any device worn on a user's face. The user may be a patient, an operator, an observer, or any other person.

Another aspect of one form of the present technology is directed to a positioning and stabilising structure configured to connect to a facial interface (e.g., a plenum chamber of a patient interface) and to provide a force to hold the facial interface in an effective position on a user's head.

Another aspect of one form the present technology is directed to a patient interface comprising: a plenum chamber pressurisable to a therapeutic pressure; a seal-forming structure constructed and arranged to form a seal with a region of a patient's face surrounding an entrance to a patient's airways for sealed delivery of a flow of air at the therapeutic pressure, the seal-forming structure constructed and arranged to maintain said therapeutic pressure in the plenum chamber throughout the patient's respiratory cycle in use; and a positioning and stabilising structure to provide a force to hold a seal-forming structure in a therapeutically effective position on a patient's head, the positioning and stabilising structure comprising: at least one rigidized arm configured, in use, to be positioned adjacent to a cheek of the patient, and a strap removably received around the rigidized arm and configured to contact, in use, a posterior region of the patient's head.

Another aspect of one form of the present technology is directed to a positioning and stabilising structure configured to support a facial interface (e.g., a plenum chamber of a patient interface), the positioning and stabilising structure comprising: at least one rigidized arm configured, in use, to be positioned adjacent to a cheek of the user, and a strap removably received around the rigidized arm and configured to contact, in use, a posterior region of the user's head.

Another aspect of one form of the present technology is the a patient interface comprising: a plenum chamber pressurisable to a therapeutic pressure; a seal-forming structure constructed and arranged to form a seal with a region of a patient's face surrounding an entrance to a patient's airways for sealed delivery of a flow of air at the therapeutic pressure, and the seal-forming structure constructed and arranged to maintain said therapeutic pressure in the plenum chamber throughout the patient's respiratory cycle in use; and a positioning and stabilising structure to provide a force to hold a seal-forming structure in a therapeutically effective position on a patient's head, the positioning and stabilising structure comprising: at least one arm, a strap removably received around the arm, the strap comprising a first rigid coupling having a mechanical connection that engages the rigidized arm and limits movement of the rigidized arm into and out of a cavity of the strap.

Another aspect of one form of the present technology is directed to a positioning and stabilising structure configured to support a facial interface (e.g., a plenum chamber of a patient interface), the positioning and stabilising structure comprising: at least one arm, a strap removably received around the arm, the strap comprising a first rigid coupling having a mechanical connection that engages the rigidized arm and limits movement of the rigidized arm into and out of a cavity of the strap.

Another aspect of one form of the present technology is the a patient interface comprising: a plenum chamber pressurisable to a therapeutic pressure; a seal-forming structure constructed and arranged to form a seal with a region of a patient's face surrounding an entrance to a patient's airways for sealed delivery of a flow of air at the therapeutic pressure, and the seal-forming structure constructed and arranged to maintain said therapeutic pressure in the plenum chamber throughout the patient's respiratory cycle in use; and a positioning and stabilising structure to provide a force to hold a seal-forming structure in a therapeutically effective position on a patient's head, the positioning and stabilising structure comprising: a strap configured to contact, in use, a posterior region of the patient's head, the strap comprising, a first rigid coupling, a second rigid coupling spaced apart from an outer surface of the first rigid coupling, and the sleeve being folded over the second rigid coupling and positioned between the first rigid coupling and the second rigid coupling.

Another aspect of one form of the present technology is directed to a positioning and stabilising structure configured to support a facial interface (e.g., a plenum chamber of a patient interface), the positioning and stabilising structure comprising: a strap configured to contact, in use, a posterior region of the user's head, the strap comprising, a first rigid coupling, a second rigid coupling spaced apart from an outer surface of the first rigid coupling, and the sleeve being folded over the second rigid coupling and positioned between the first rigid coupling and the second rigid coupling.

Another aspect of one form of the present technology is the a patient interface comprising: a plenum chamber pressurisable to a therapeutic pressure; a seal-forming structure constructed and arranged to form a seal with a region of a patient's face surrounding an entrance to a patient's airways for sealed delivery of a flow of air at the therapeutic pressure; and a positioning and stabilising structure to provide a force to hold a seal-forming structure in a therapeutically effective position on a patient's head, the positioning and stabilising structure comprising: a first rigid coupling, and a sleeve constructed from a flexible material, the sleeve being folded over the first rigid coupling.

Another aspect of one form of the present technology is directed to a positioning and stabilising structure configured to support a facial interface (e.g., a plenum chamber of a patient interface), the positioning and stabilising structure comprising: a first rigid coupling, and a sleeve constructed from a flexible material, the sleeve being folded over the first rigid coupling.

Another aspect of one form of the present technology is the a patient interface comprising: a plenum chamber pressurisable to a therapeutic pressure; a seal-forming structure constructed and arranged to form a seal with a region of a patient's face surrounding an entrance to a patient's airways for sealed delivery of a flow of air at the therapeutic pressure, and the seal-forming structure constructed and arranged to maintain said therapeutic pressure in the plenum chamber throughout the patient's respiratory cycle in use; and a positioning and stabilising structure to provide a force to hold a seal-forming structure in a therapeutically effective position on a patient's head, the positioning and stabilising structure comprising: at least one arm, and a strap removably received around the rigidized arm, the strap comprising, a first coupling having a mechanical connector that is configure to engage the arm, a second coupling spaced apart from an outer surface of the first coupling, and a sleeve constructed from a flexible material.

Another aspect of one form of the present technology is directed to a positioning and stabilising structure configured to support a facial interface (e.g., a plenum chamber of a patient interface), the positioning and stabilising structure comprising: at least one arm, and a strap removably received around the rigidized arm, the strap comprising, a first coupling having a mechanical connector that is configure to engage the arm, a second coupling spaced apart from an outer surface of the first coupling, and a sleeve constructed from a flexible material.

Another aspect of one form of the present technology is a patient interface comprising: a plenum chamber pressurisable to the therapeutic pressure of at least 6 cmH$_2$O above ambient air pressure, said plenum chamber including a plenum chamber inlet port sized and structured to receive a flow of air at a therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and a positioning and stabilising structure to provide a force to hold a seal-forming structure in a therapeutically effective position on the patient's head, the positioning and stabilising structure comprising: at least one rigidized arm configured, in use, to be positioned adjacent to a cheek of the patient; and a strap removably received around the rigidized arm and configured to contact, in use, a posterior region of the patient's head, the strap comprising, a first rigid coupling forming an opening to a cavity, the rigidized arm being positionable through the opening and into the cavity, the first rigid coupling having a mechanical connector that is configured to engage the rigidized arm and limit movement of the rigidized arm into and out of the cavity, a second rigid coupling spaced apart from an outer surface of the first rigid coupling, and a sleeve constructed from a flexible material, the sleeve being folded over the second rigid coupling and positioned between the first rigid coupling and the second rigid coupling.

In certain forms, the sleeve includes an outer surface that comprises the outermost surface of the strap, and an inner surface that comprises a boundary of the cavity.

In certain forms, the mechanical connector of the first rigid coupling includes a projection, and the rigidized arm includes a recess configured to receive the projection.

In certain forms, the projection extends at an angle between 40° and 60° from an inner surface of the first rigid coupling.

In certain forms, the mechanical connector comprises a snap-fit connection.

In certain forms, the flexible material is a textile.

In certain forms, the flexible material is elastic and/or elastomeric.

In certain forms, the first rigid coupling and the second rigid coupling have a generally circular shape, the rigidized arm further including an extension having at least a portion of the generally circular shape.

In certain forms, the rigidized arm is configured to not extend in a posterior direction further than the patient's ear.

In certain forms, the strap includes a first piece and a second piece coupled together using a length adjuster, wherein the length adjuster is configured to change a usable length of the strap.

In certain forms, the strap is bifurcated.

In certain forms, the at least one rigidized arm comprises a first rigidized arm configured, in use, to be positioned on a left side of the patient's head, a second rigidized arm coupled to the positioning and stabilising structure and configured, in use, to be positioned adjacent to a right cheek of the patient, and the strap is removably received around the second rigidized arm, the strap comprising: a third rigid coupling defining a second opening to the cavity, the second rigidized arm being positionable through the second opening and into the cavity, the third rigid coupling having a mechanical connector that engages the second rigidized arm and limits movement of the second rigidized arm into and out of the second opening of the cavity, a fourth rigid coupling spaced apart from an outer surface of the first rigid coupling, and the sleeve being folded over the fourth rigid coupling and positioned between the third rigid coupling and the fourth rigid coupling.

In certain forms, the plenum chamber inlet port is a first plenum chamber inlet port, the plenum chamber further includes a second plenum chamber inlet port, the first plenum chamber inlet port configured to receive the flow of air at the therapeutic pressure, and the second plenum chamber inlet port configured to receive a plug configured to prevent the flow of air at the therapeutic pressure from escaping.

In certain forms, the rigidized arm includes the plug.

In certain forms, the plug is removable from the second opening in order to permit pressurized air to flow through the second opening.

In certain forms, the rigidized arm is at least partially flexible in order to adjust a contour to substantially correspond to the cheek of the patient.

In certain forms, the seal-forming structure defines nasal pillows or a cradle.

In certain forms, the first rigid coupling, the second rigid coupling, and the sleeve are coupled together using an adhesive.

In certain forms, the cavity includes a width less than a width of the rigidized arm, and wherein the sleeve is configured to stretch upon receiving the rigidized arm.

Another aspect of one form of the present technology is a patient interface that is moulded or otherwise constructed with a perimeter shape which is complementary to that of an intended wearer.

An aspect of one form of the present technology is a method of manufacturing the patient interface.

In certain forms, the method comprises the steps of forming the strap by: providing the flexible material; inserting the second coupling into the cavity of the flexible material; folding an end of the flexible material into the cavity to enclose the second coupling; and inserting the first coupling into the cavity.

In certain forms, the method comprises the steps of connecting the positioning and stabilising structure to the seal-forming structure by: providing a plenum chamber with a connection opening; and inserting a plug of the rigidized arm into the connection opening.

In certain forms, the method comprises applying an adhesive around the connection opening in order to secure the plug within the opening.

In certain forms, the method comprises removing the plug from the connection opening.

Another aspect of one form of the present technology is directed to a patient interface that may comprise: a plenum chamber; a seal-forming structure; and a positioning and stabilising structure. The seal-forming structure may include an inlet port and the plenum chamber may include at least one connection port.

In certain forms, the inlet port is configured to receive pressurized air and the at least one connection port is configured to receive a plug to limit fluid flow through the connection port.

In certain forms, the inlet port is configured to receive a cover and the at least one connection port is configured to receive pressurized air.

In certain forms, the positioning and stabilising structure is connected at the connection port. The positioning and stabilising structure may be either conduit headgear that conveys fluid from a top of a patient's head to the plenum chamber. Or, the positioning and stabilising structure may be a plug connected to a rigidized arm.

Another aspect of one form of the present technology is directed to a positioning and stabilising structure configured to support a facial interface (e.g., a plenum chamber of a patient interface), the positioning and stabilising structure comprising: at least one rigidized arm configured, in use, to be positioned adjacent to a cheek of the user; and a strap removably received around the rigidized arm and configured to contact, in use, a posterior region of the user's head, the strap comprising, a first rigid coupling forming an opening to a cavity, the rigidized arm being positionable through the opening and into the cavity, the first rigid coupling having a mechanical connector that is configured to engage the rigidized arm and limit movement of the rigidized arm into and out of the cavity, a second rigid coupling spaced apart from an outer surface of the first rigid coupling, and a sleeve constructed from a flexible material, the sleeve being folded over the second rigid coupling and positioned between the first rigid coupling and the second rigid coupling.

An aspect of one form of the present technology is a method of manufacturing the positioning and stabilising structure.

In certain forms, the method of manufacturing the positioning and stabilising structure comprises the steps of forming the strap by: providing the flexible material; inserting the second coupling into the cavity of the flexible material; folding an end of the flexible material into the cavity to enclose the second coupling; and inserting the first coupling into the cavity.

Another aspect of one form of the present technology is a patient interface comprising: a plenum chamber pressurisable to a therapeutic pressure of at least 6 cmH2O above ambient air pressure, said plenum chamber including a plenum chamber inlet port sized and structured to receive a flow of air at the therapeutic pressure for breathing by the patient, and a connection inlet port sized and structured to receive a flow of air at the therapeutic pressure for breathing by a patient; a seal-forming structure constructed and arranged to form a seal with a region of the patient's face surrounding an entrance to the patient's airways, said seal-forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and wherein the connection inlet port is configured to removably receive a positioning and stabilising structure to provide a force to hold a seal-forming structure in a therapeutically effective position on the patient's head, the positioning and stabilising structure comprising at least one of: a rigidized arm configured to limit fluid flow through the connection inlet port, and the arm configured to be positioned along the patient's cheek while in use; and a conduit headgear configured to convey the flow of air through the connection inlet port to the patient.

In certain forms, the rigidized arm is coupled to the connection inlet port, the rigidized arm comprises: a plug removably received within the connection inlet port and configured to limit the flow of air through the connection inlet port; and a rigidized arm portion configured to be positioned adjacent to a cheek of the patient.

In certain forms, the plenum chamber inlet port is configured to receive the flow of air when in use.

In certain forms, the conduit headgear is coupled to the connection inlet port, the conduit headgear comprising: an inlet configured to receive the flow of air, the inlet disposed on a superior portion of the patient's head in use; and a hollow tube configured to convey the flow of air to the plenum chamber.

In certain forms, a cover is removably received within the plenum chamber inlet port while the conduit headgear is coupled to the connection inlet port, the cover limiting fluid flow through the plenum chamber inlet port.

In certain forms, the rigidized arm and the conduit headgear are interchangeably connectable to the connection inlet port.

An aspect of one form of the present technology is a method of using the patient interface.

In certain forms, the method comprises: providing the seal forming structure; selecting the positioning and stabilising structure from one of the rigidized arm and the conduit headgear; connecting the positioning and stabilising structure to the connection inlet port; connecting one of an air circuit and a cover to the plenum chamber inlet port; and providing a flow of air through one of the positioning and stabilising structure and the air circuit, and limiting the flow of air using one of the cover and the positioning and stabilising structure.

Another aspect of one form of the present technology is directed to a positioning and stabilising structure configured to support a facial interface (e.g., a plenum chamber of a patient interface), the positioning and stabilising structure comprising at least one of: a rigidized arm configured to limit fluid flow through the connection inlet port, and the arm configured to be positioned along the user's cheek while in use; and a conduit headgear configured to convey the flow of air through the connection inlet port to the user.

An aspect of one form of the present technology is a method of using the positioning and stabilising structure.

An aspect of certain forms of the present technology is a medical device that is easy to use, e.g. by a person who does not have medical training, by a person who has limited dexterity, vision or by a person with limited experience in using this type of medical device.

An aspect of one form of the present technology is a portable RPT device that may be carried by a person, e.g., around the home of the person.

An aspect of one form of the present technology is a patient interface that may be washed in a home of a patient, e.g., in soapy water, without requiring specialised cleaning equipment. An aspect of one form of the present technology is a humidifier tank that may be washed in a home of a patient, e.g., in soapy water, without requiring specialised cleaning equipment.

The methods, systems, devices and apparatus described may be implemented so as to improve the functionality of a processor, such as a processor of a specific purpose computer, respiratory monitor and/or a respiratory therapy apparatus. Moreover, the described methods, systems, devices and apparatus can provide improvements in the technological field of automated management, monitoring and/or treatment of respiratory conditions, including, for example, sleep disordered breathing.

Of course, portions of the aspects may form sub-aspects of the present technology. Also, various ones of the sub-aspects and/or aspects may be combined in various manners and also constitute additional aspects or sub-aspects of the present technology.

Other features of the technology will be apparent from consideration of the information contained in the following detailed description, abstract, drawings and claims.

4 BRIEF DESCRIPTION OF THE DRAWINGS

The present technology is illustrated by way of example, and not by way of limitation, in the figures of the accompanying drawings, in which like reference numerals refer to similar elements including:

4.1 Respiratory Therapy Systems

FIG. 1A shows a system including a patient 1000 wearing a patient interface 3000, in the form of nasal pillows, receiving a supply of air at positive pressure from an RPT device 4000. Air from the RPT device 4000 is humidified in a humidifier 5000, and passes along an air circuit 4170 to the patient 1000. A bed partner 1100 is also shown. The patient is sleeping in a supine sleeping position.

FIG. 1B shows a system including a patient 1000 wearing a patient interface 3000, in the form of a nasal mask, receiving a supply of air at positive pressure from an RPT device 4000. Air from the RPT device 4000 is humidified in a humidifier 5000, and passes along an air circuit 4170 to the patient 1000.

FIG. 1C shows a system including a patient 1000 wearing a patient interface 3000, in the form of a full-face mask, receiving a supply of air at positive pressure from an RPT device 4000. Air from the RPT device is humidified in a humidifier 5000, and passes along an air circuit 4170 to the patient 1000. The patient is sleeping in a side sleeping position.

4.2 Respiratory System and Facial Anatomy

Figure 1A:
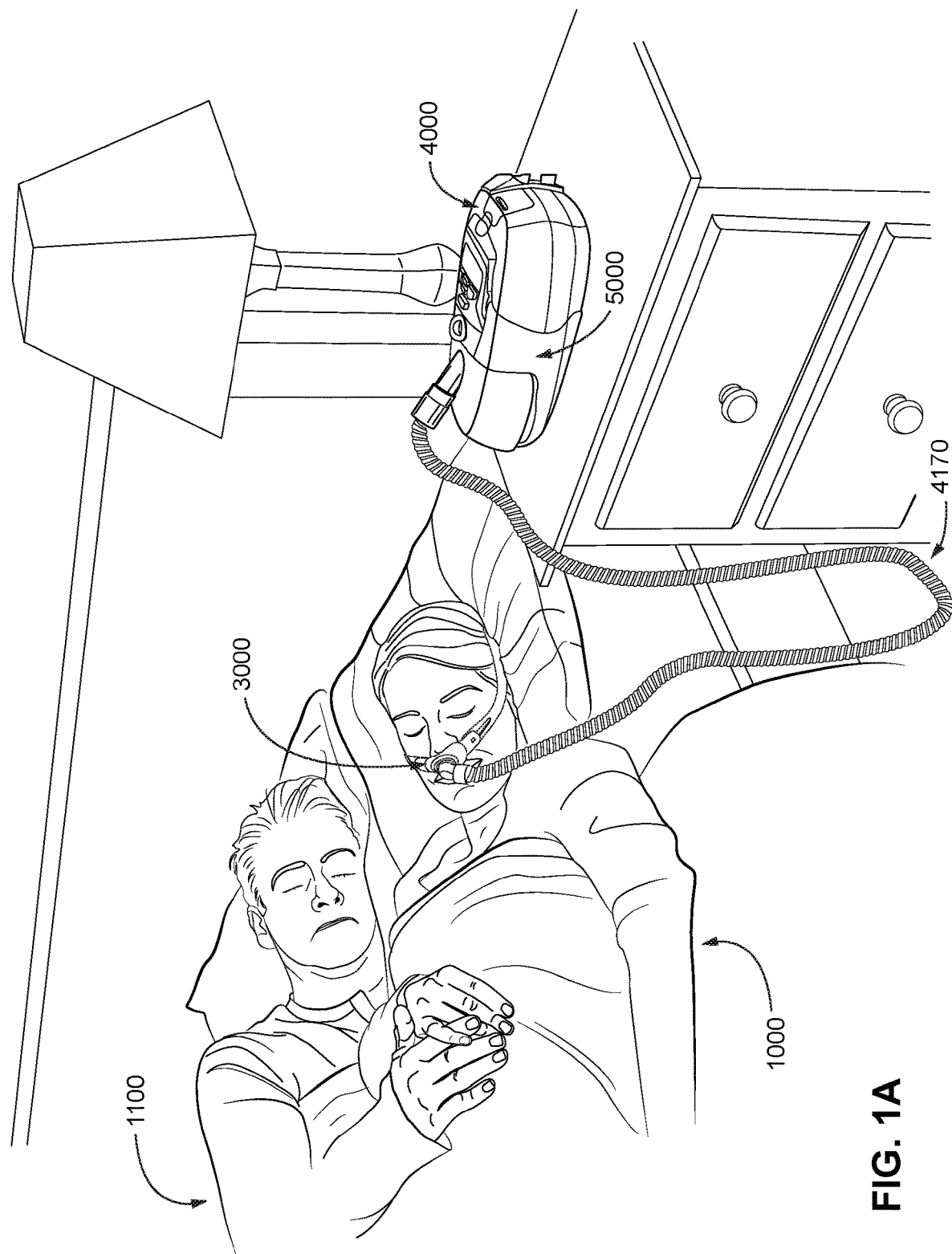
Figure 1B:
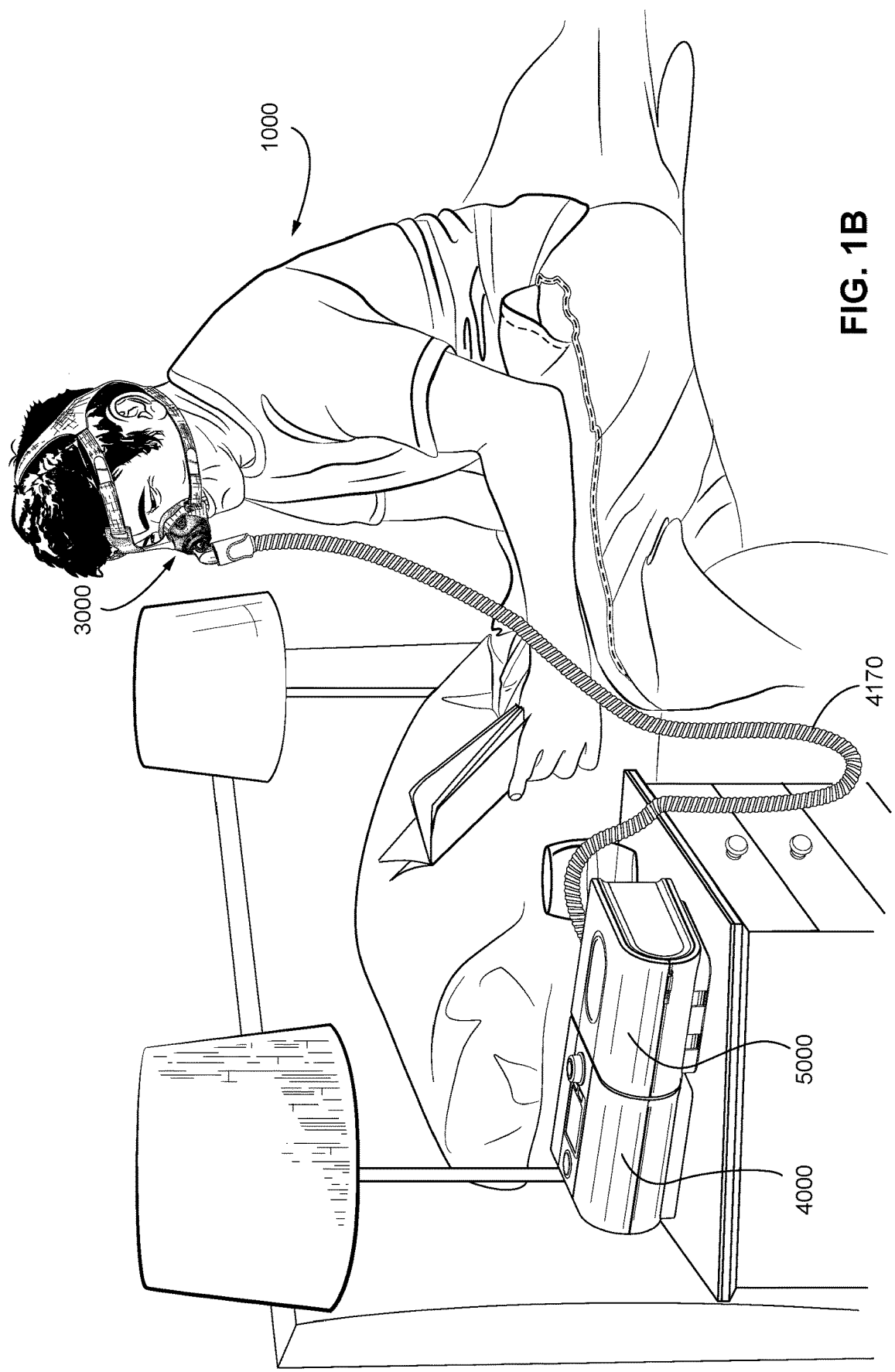
Figure 1C:
Figure 2A:
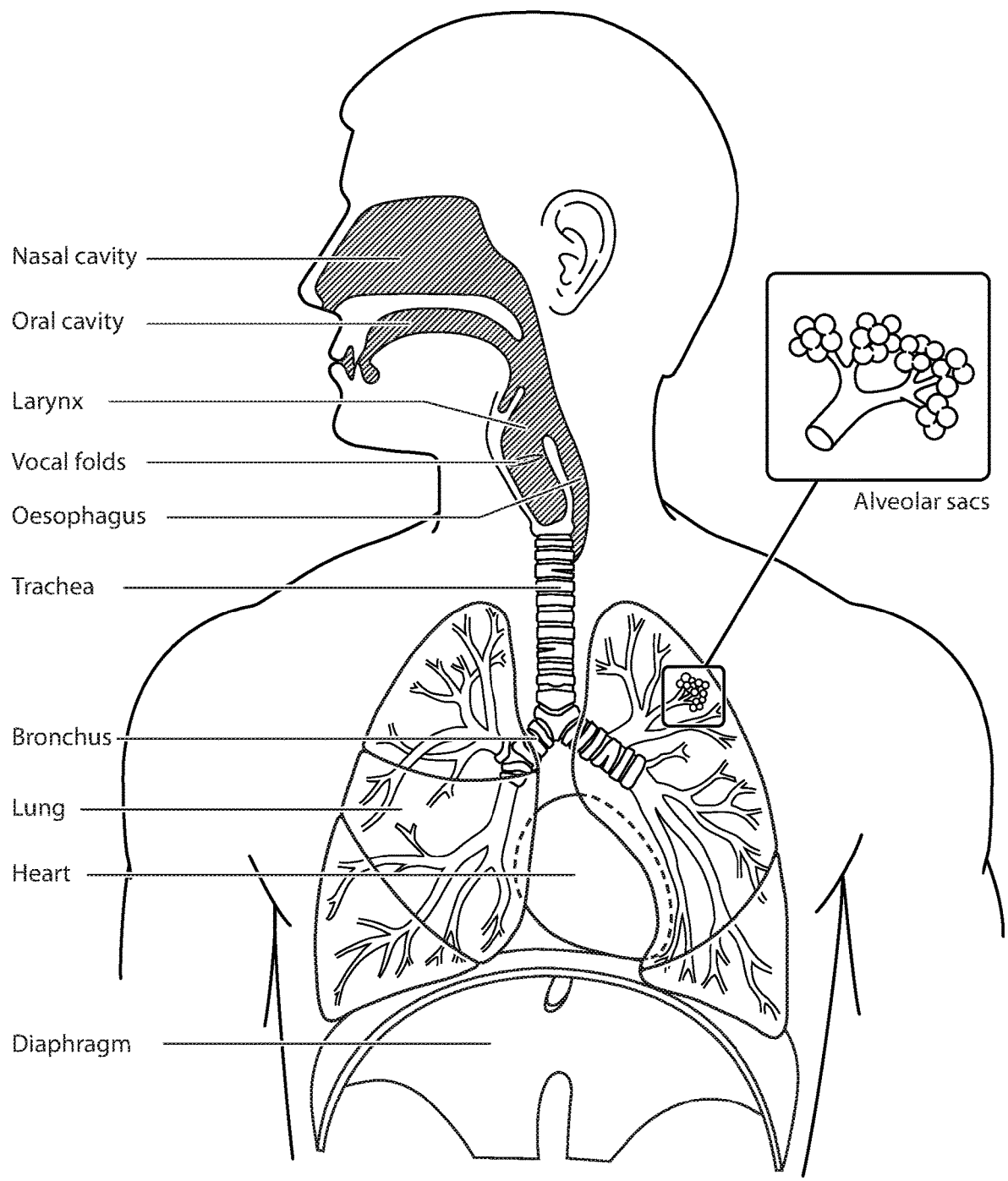
FIG. 2A shows an overview of a human respiratory system including the nasal and oral cavities, the larynx, vocal folds, oesophagus, trachea, bronchus, lung, alveolar sacs, heart and diaphragm.
Figure 2B:
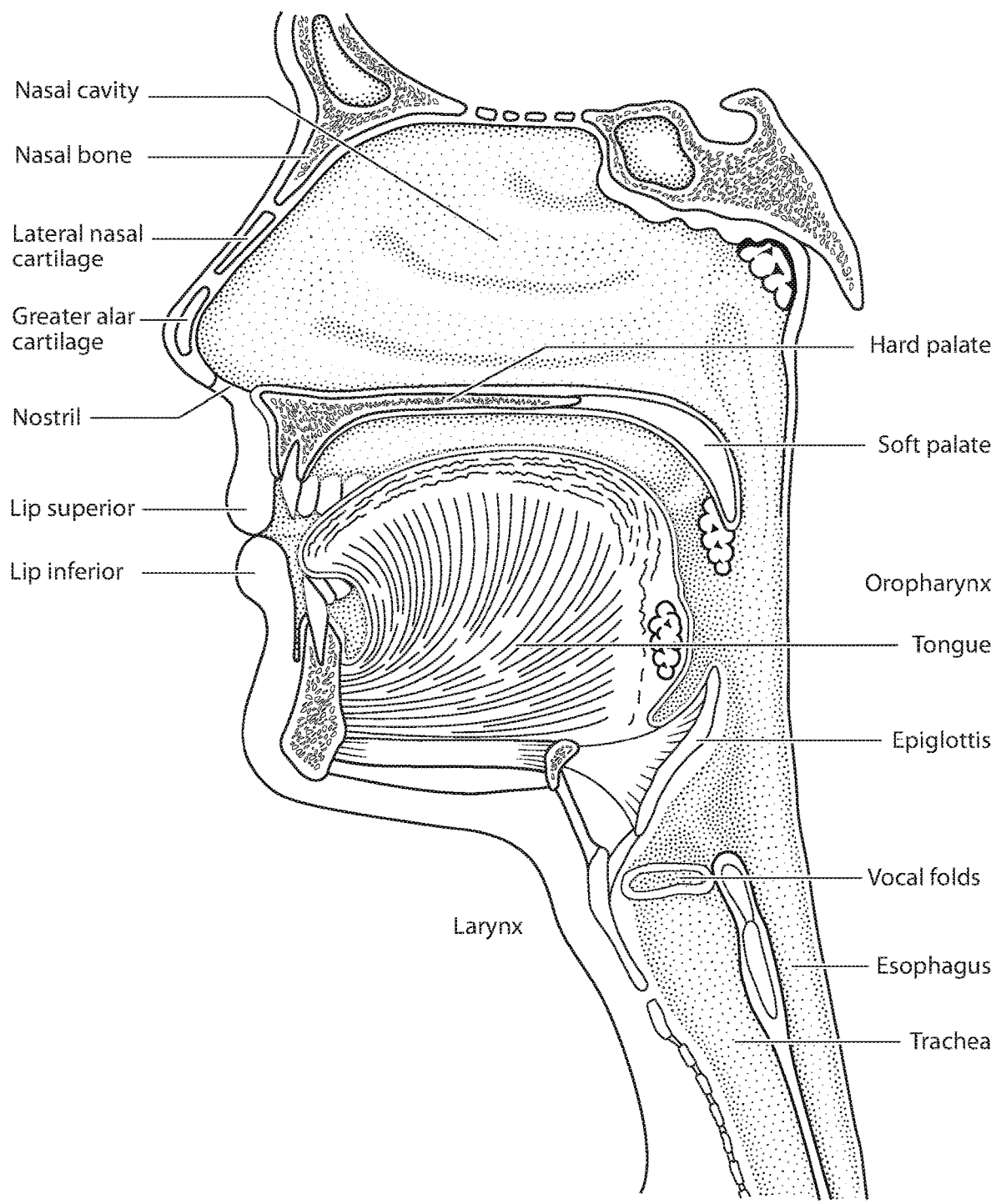
FIG. 2B shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.
Figure 2C:
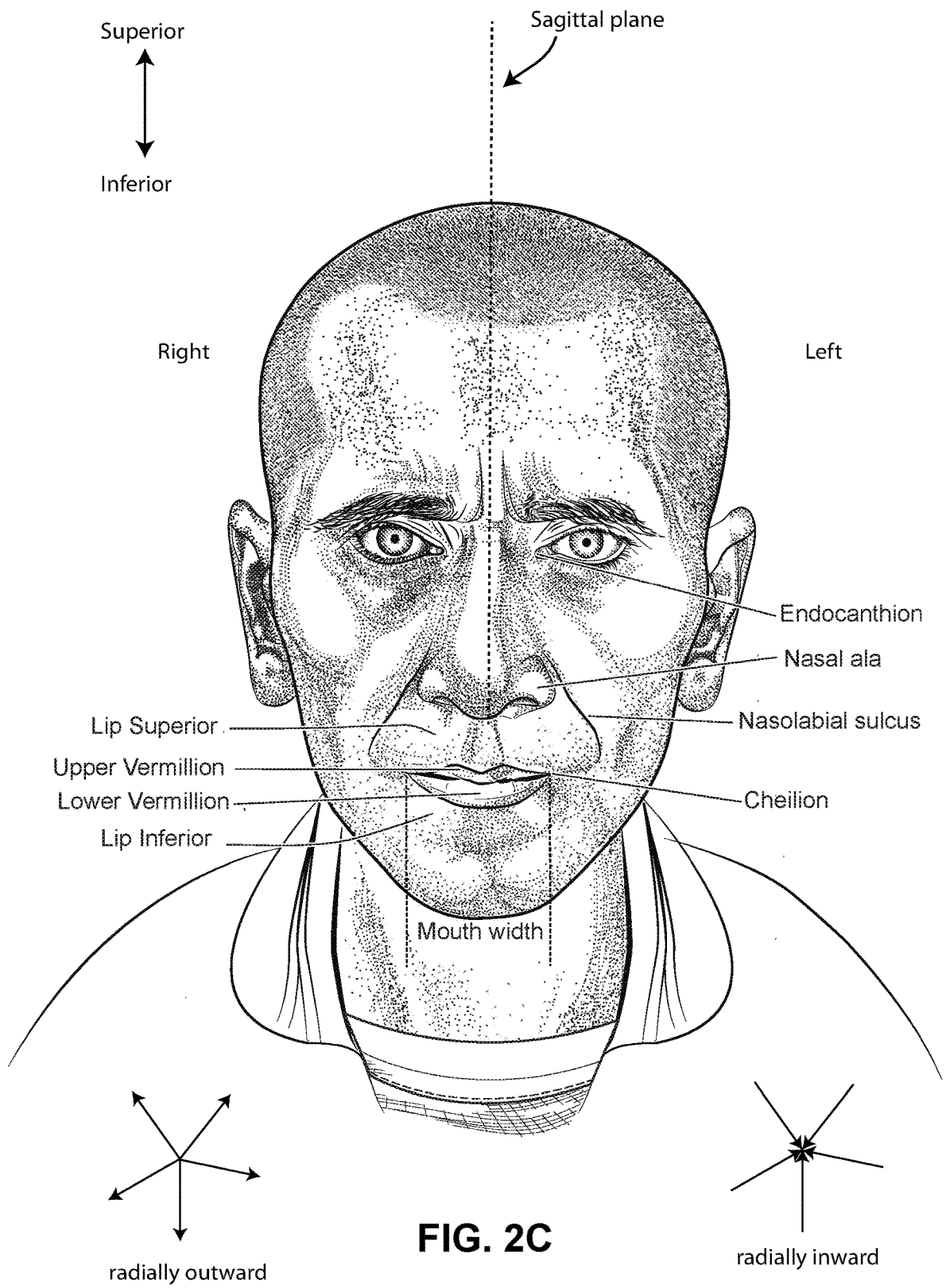
FIG. 2C is a front view of a face with several features of surface anatomy identified including the lip superior, upper vermilion, lower vermilion, lip inferior, mouth width, endocanthion, a nasal ala, nasolabial sulcus and cheilion. Also indicated are the directions superior, inferior, radially inward and radially outward.
Figure 2D:
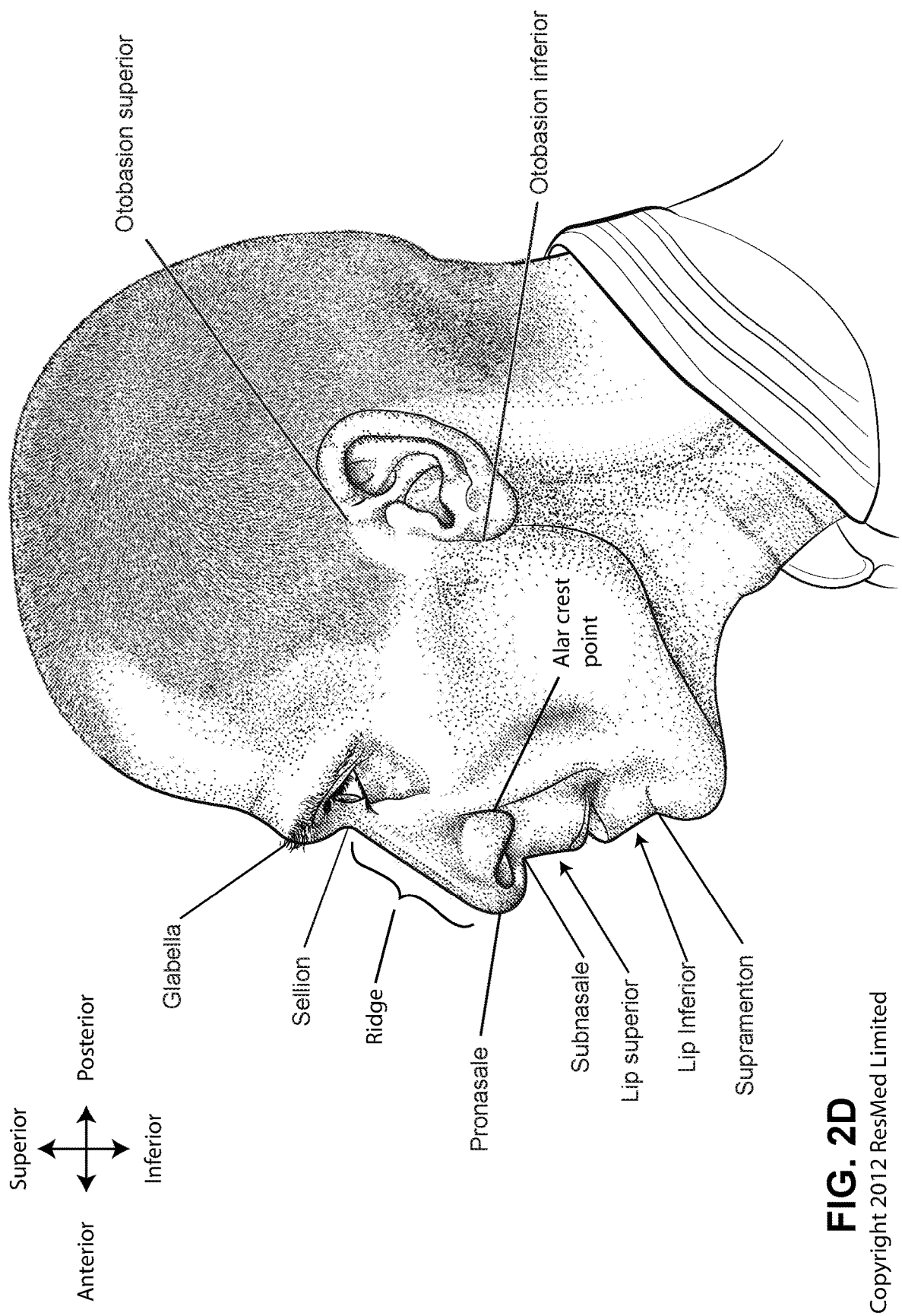
FIG. 2D is a side view of a head with several features of surface anatomy identified including *glabella*, sellion, pronasale, subnasale, lip superior, lip inferior, supramenton, nasal ridge, alar crest point, otobasion superior and otobasion inferior. Also indicated are the directions superior & inferior, and anterior & posterior.
Figure 2E:
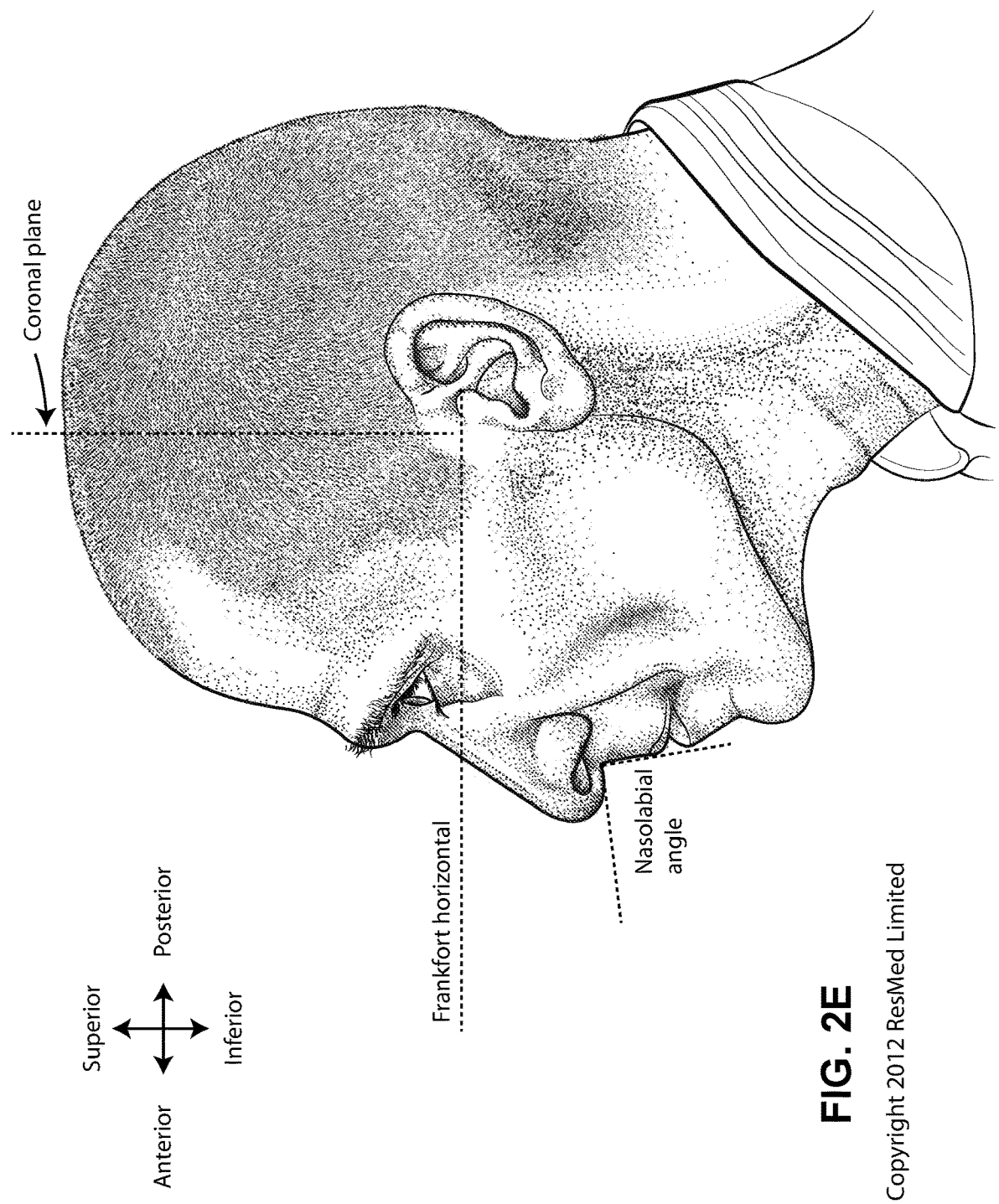

FIG. 2E is a further side view of a head. The approximate locations of the Frankfort horizontal and nasolabial angle are indicated. The coronal plane is also indicated.

Figure 2F:
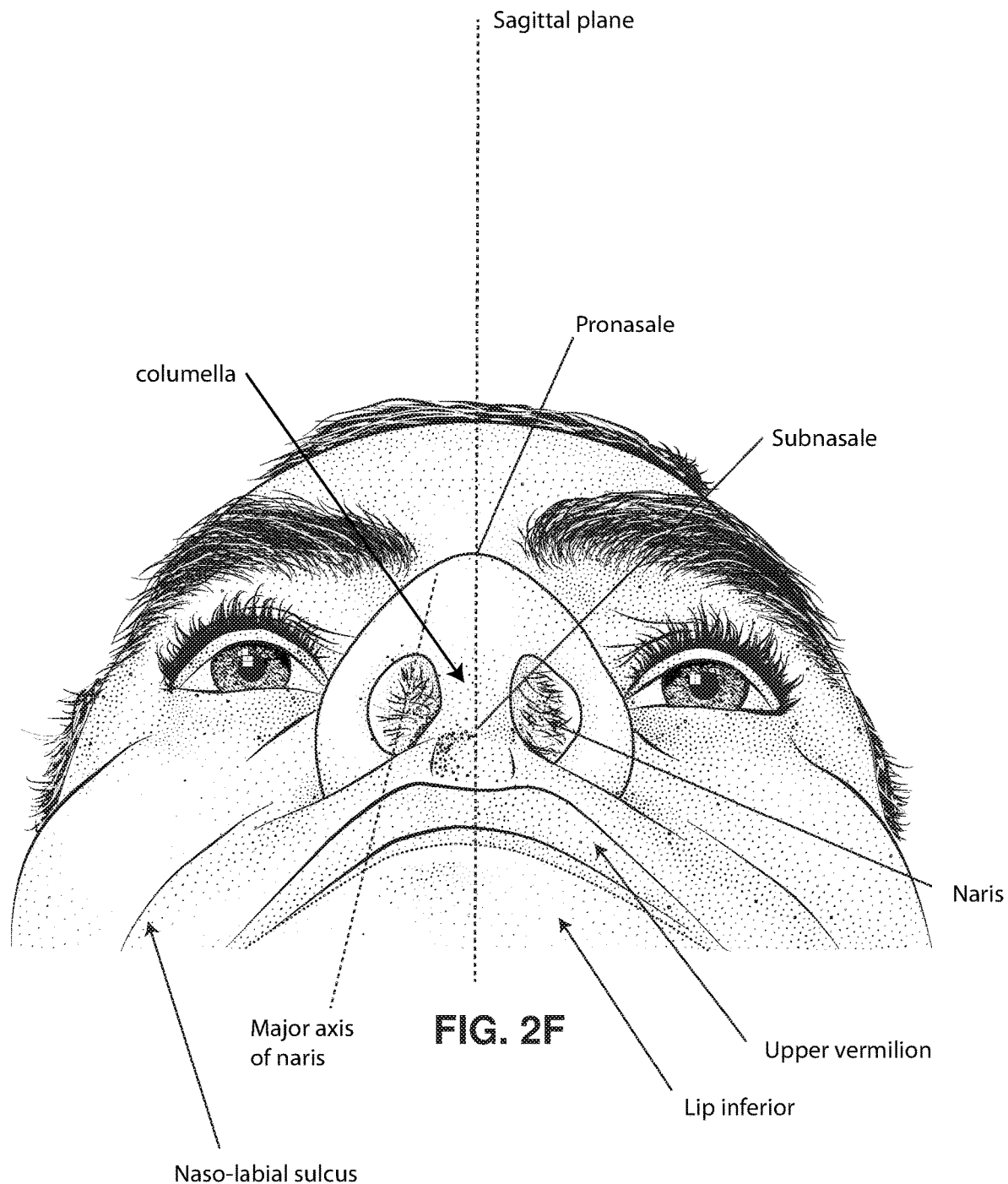

FIG. 2F shows a base view of a nose with several features identified including naso-labial sulcus, lip inferior, upper Vermilion, naris, subnasale, columella, pronasale, the major axis of a naris and the midsagittal plane.

FIG. 2G shows a side view of the superficial features of a nose.

FIG. 2H shows subcutaneal structures of the nose, including lateral cartilage, septum cartilage, greater alar cartilage, lesser alar cartilage, sesamoid cartilage, nasal bone, epidermis, adipose tissue, frontal process of the maxilla and fibrofatty tissue.

FIG. 2I shows a medial dissection of a nose, approximately several millimeters from the midsagittal plane, amongst other things showing the septum cartilage and medial crus of greater alar cartilage.

Figures 2J, 2K:
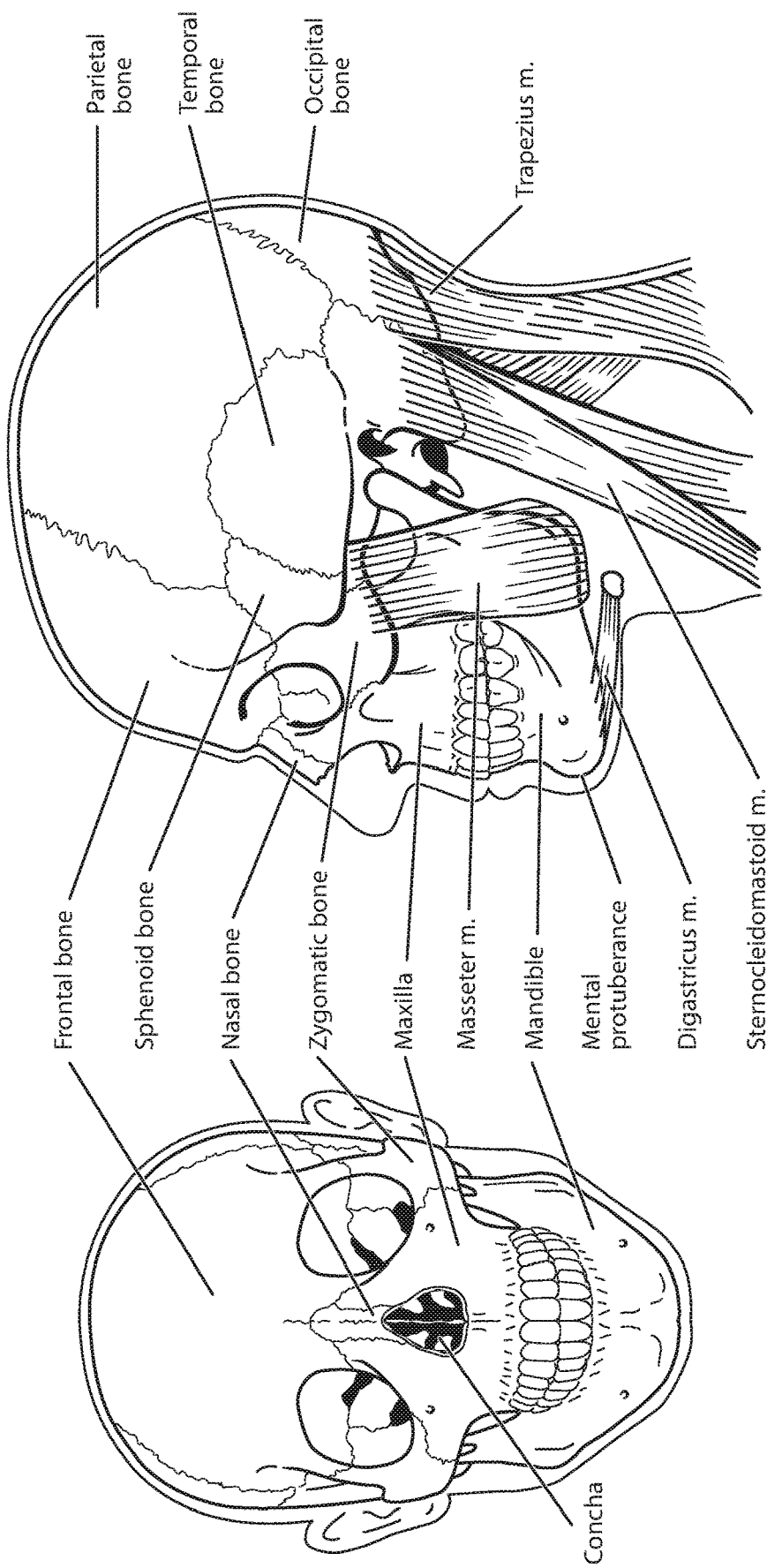

FIG. 2J shows a front view of the bones of a skull including the frontal, nasal and zygomatic bones. Nasal concha are indicated, as are the maxilla, and mandible.

FIG. 2K shows a lateral view of a skull with the outline of the surface of a head, as well as several muscles. The following bones are shown: frontal, sphenoid, nasal, zygomatic, maxilla, mandible, parietal, temporal and occipital. The mental protuberance is indicated. The following muscles are shown: digastricus, masseter, sternocleidomastoid and trapezius.

Figure 2L:
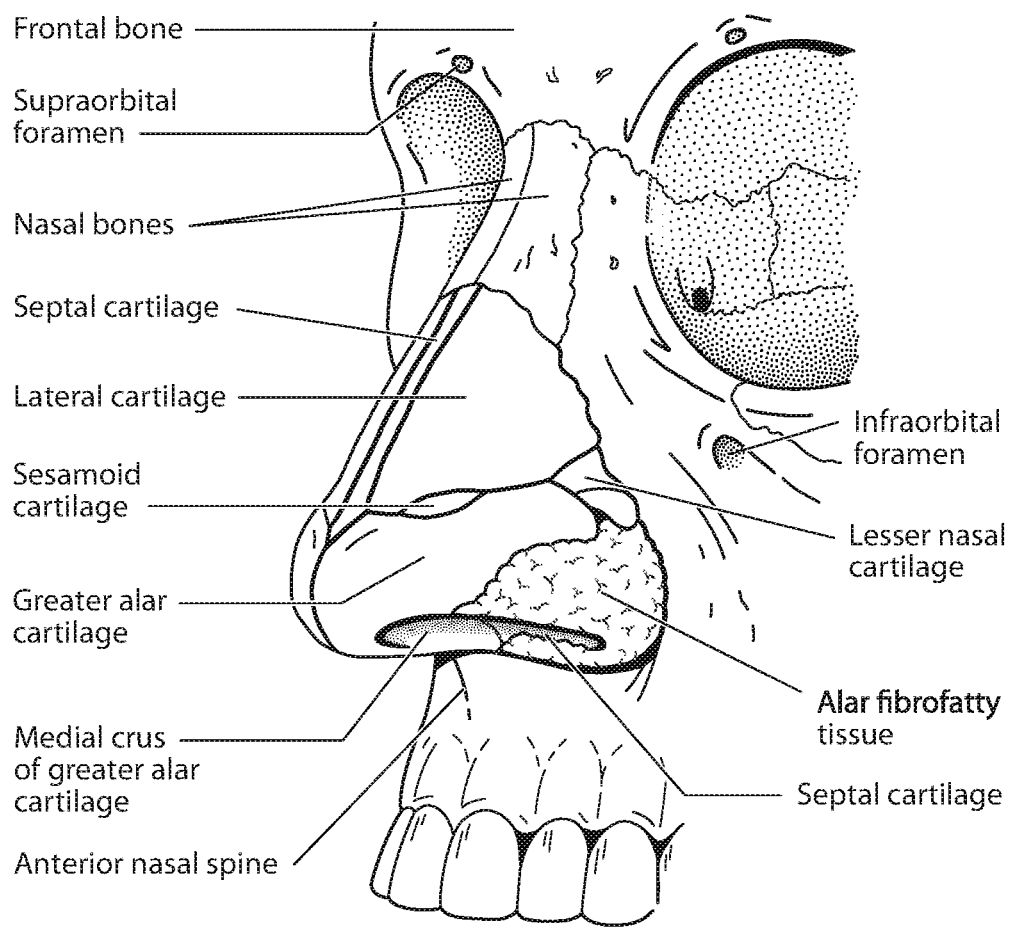

FIG. 2L shows an anterolateral view of a nose.

4.3 Patient Interface

Figure 3A:
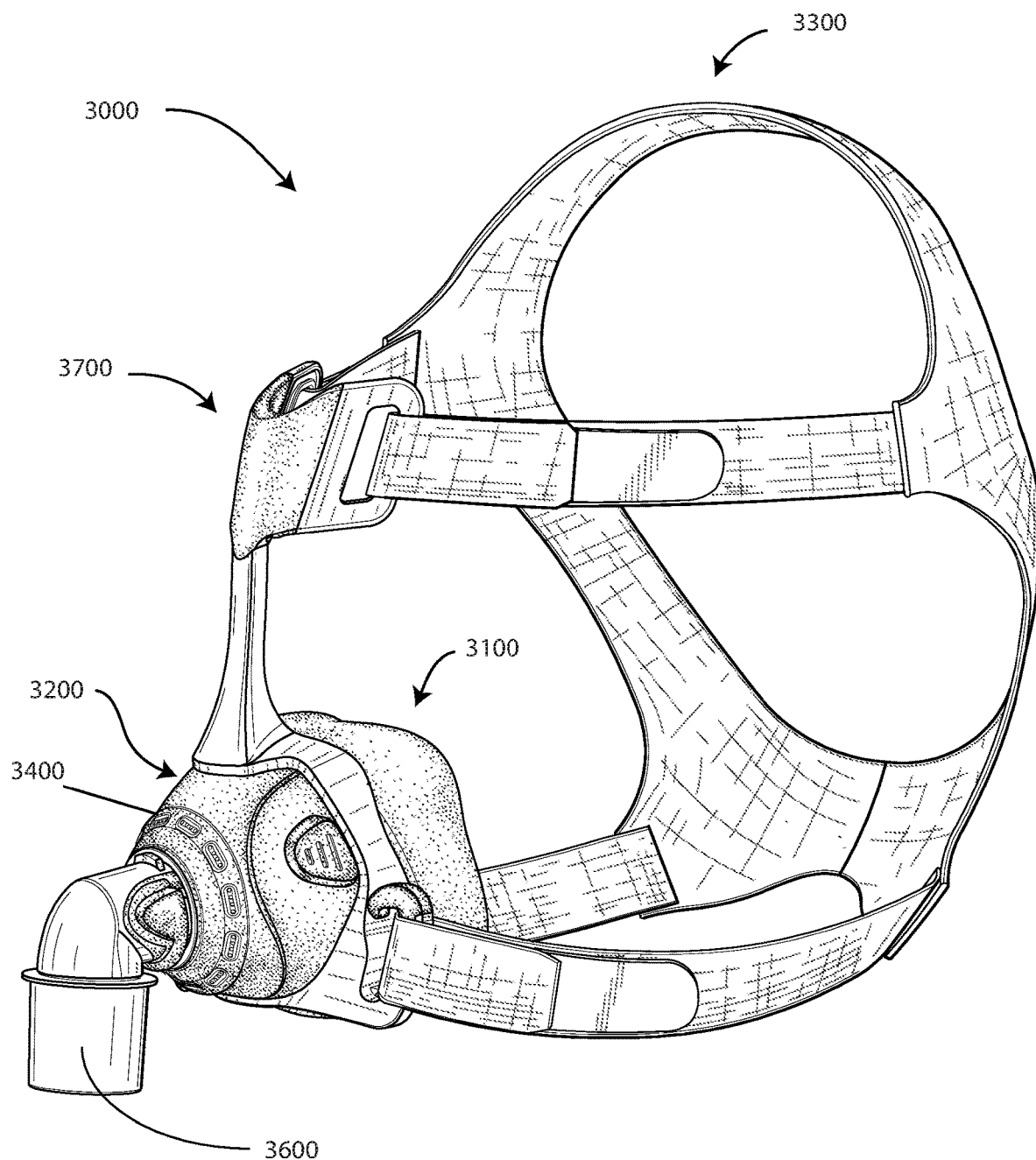

FIG. 3A shows a patient interface in the form of a nasal mask in accordance with one form of the present technology.

Figure 3B:
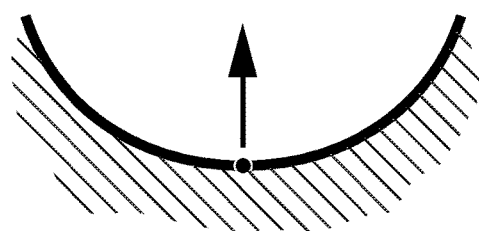

FIG. 3B shows a schematic of a cross-section through a structure at a point. An outward normal at the point is indicated. The curvature at the point has a positive sign, and a relatively large magnitude when compared to the magnitude of the curvature shown in FIG. 3C.

Figure 3C:
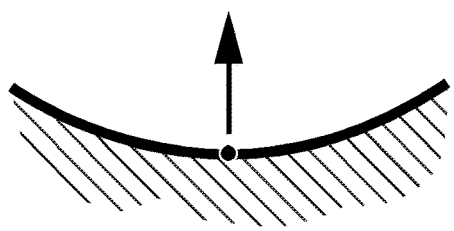

FIG. 3C shows a schematic of a cross-section through a structure at a point. An outward normal at the point is indicated. The curvature at the point has a positive sign, and a relatively small magnitude when compared to the magnitude of the curvature shown in FIG. 3B.

Figure 3D:
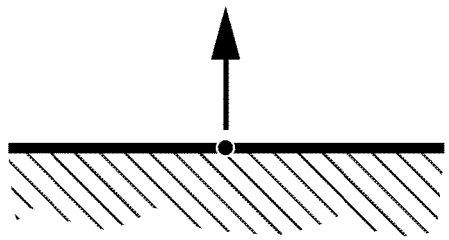

FIG. 3D shows a schematic of a cross-section through a structure at a point. An outward normal at the point is indicated. The curvature at the point has a value of zero.

Figure 3E:
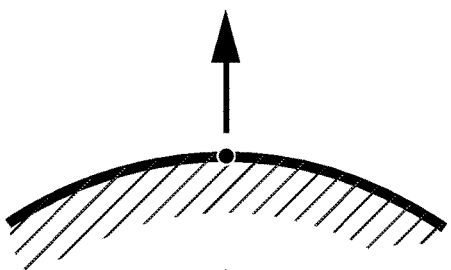

FIG. 3E shows a schematic of a cross-section through a structure at a point. An outward normal at the point is indicated. The curvature at the point has a negative sign, and a relatively small magnitude when compared to the magnitude of the curvature shown in FIG. 3F.

Figure 3F:
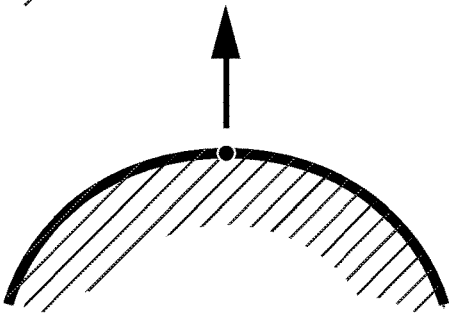

FIG. 3F shows a schematic of a cross-section through a structure at a point. An outward normal at the point is indicated. The curvature at the point has a negative sign, and a relatively large magnitude when compared to the magnitude of the curvature shown in FIG. 3E.

Figure 3H:
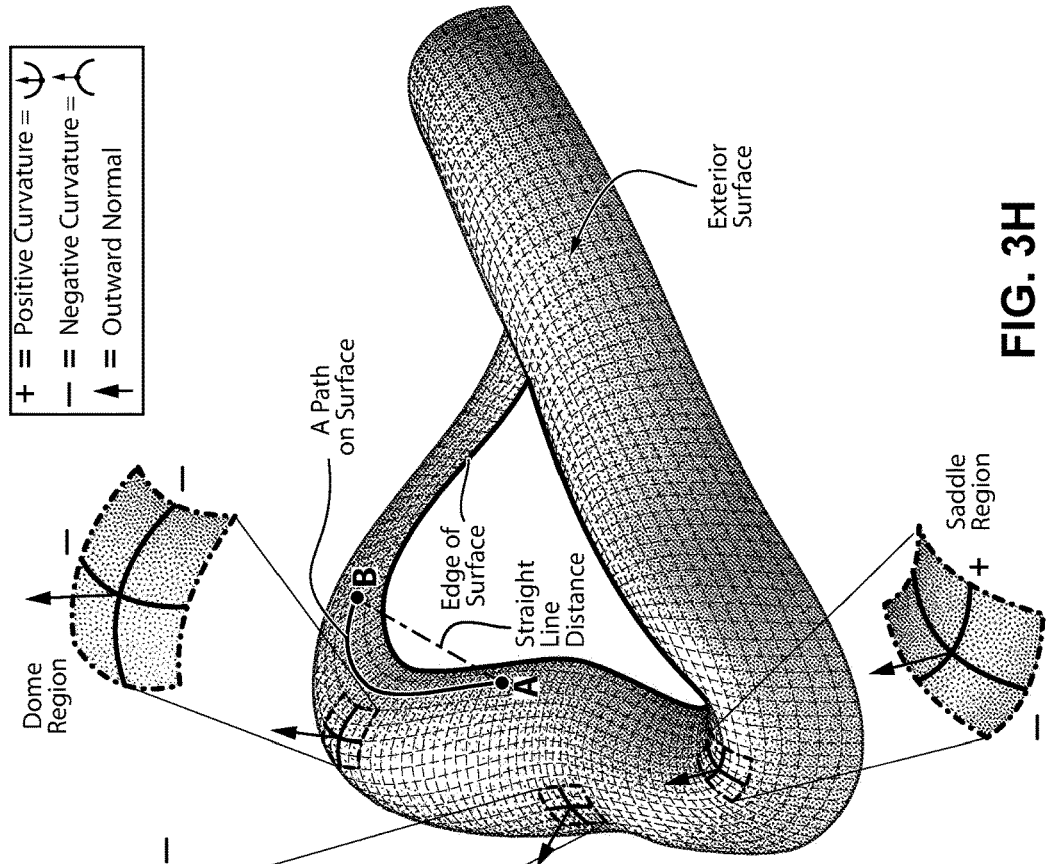
Figure 3G:
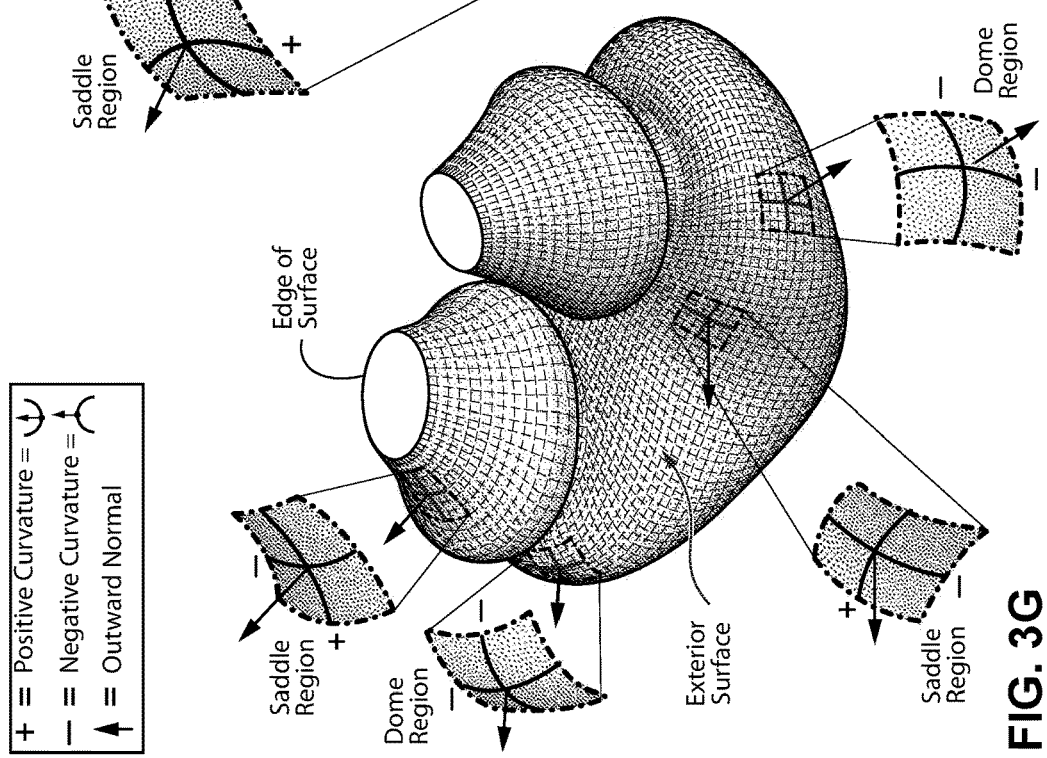

FIG. 3G shows a cushion for a mask that includes two pillows. An exterior surface of the cushion is indicated. An edge of the surface is indicated. Dome and saddle regions are indicated.

FIG. 3H shows a cushion for a mask. An exterior surface of the cushion is indicated. An edge of the surface is indicated. A path on the surface between points A and B is indicated. A straight line distance between A and B is indicated. Two saddle regions and a dome region are indicated.

FIG. 3I shows the surface of a structure, with a one dimensional hole in the surface. The illustrated plane curve forms the boundary of a one dimensional hole.

FIG. 3J shows a cross-section through the structure of FIG. 3I. The illustrated surface bounds a two dimensional hole in the structure of FIG. 3I.

FIG. 3K shows a perspective view of the structure of FIG. 3I, including the two dimensional hole and the one dimensional hole. Also shown is the surface that bounds a two dimensional hole in the structure of FIG. 3I.

FIG. 3L shows a mask having an inflatable bladder as a cushion.

FIG. 3M shows a cross-section through the mask of FIG. 3L, and shows the interior surface of the bladder. The interior surface bounds the two dimensional hole in the mask.

FIG. 3N shows a further cross-section through the mask of FIG. 3L. The interior surface is also indicated.

FIG. 3O illustrates a left-hand rule.

FIG. 3P illustrates a right-hand rule.

FIG. 3Q shows a left ear, including the left ear helix.

FIG. 3R shows a right ear, including the right ear helix.

FIG. 3S shows a right-hand helix.

FIG. 3T shows a view of a mask, including the sign of the torsion of the space curve defined by the edge of the sealing membrane in different regions of the mask.

Figure 3U:
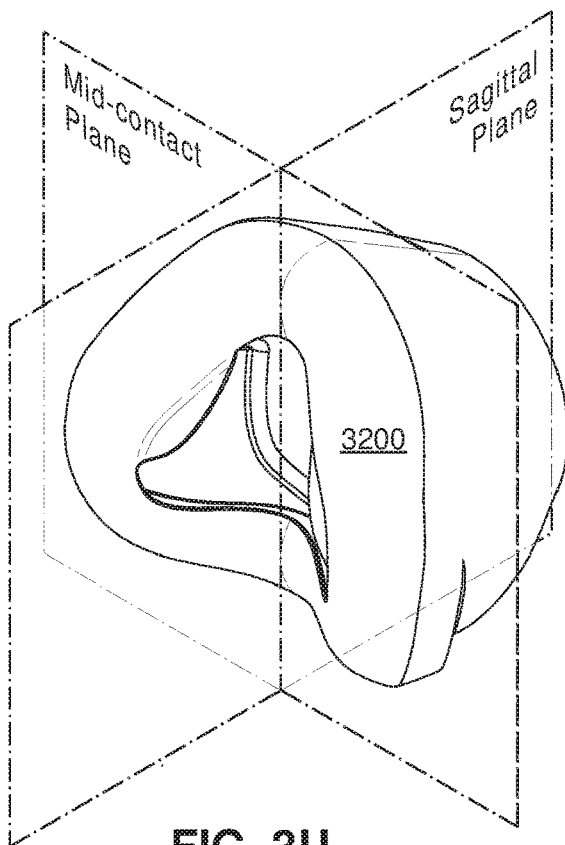

FIG. 3U shows a view of a plenum chamber 3200 showing a sagittal plane and a mid-contact plane.

Figure 3V:
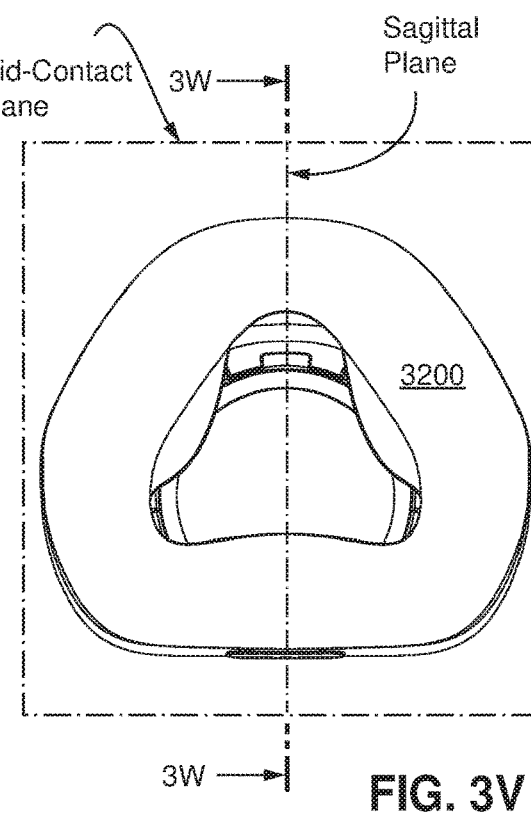

FIG. 3V shows a view of a posterior of the plenum chamber of FIG. 3U. The direction of the view is normal to the mid-contact plane. The sagittal plane in FIG. 3V bisects the plenum chamber into left-hand and right-hand sides.

Figure 3W:
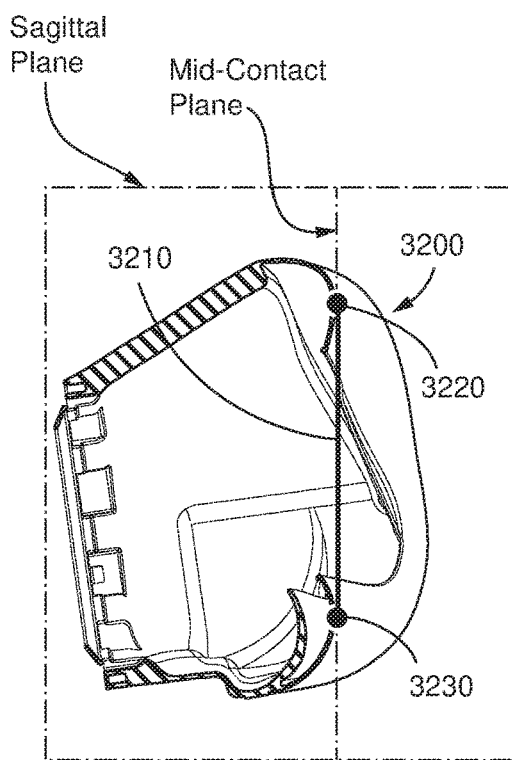

FIG. 3W shows a cross-section through the plenum chamber of FIG. 3V, the cross-section being taken at the sagittal plane shown in FIG. 3V. A 'mid-contact' plane is shown. The mid-contact plane is perpendicular to the sagittal plane. The orientation of the mid-contact plane corresponds to the orientation of a chord 3210 which lies on the sagittal plane and just touches the cushion of the plenum chamber at two points on the sagittal plane: a superior point 3220 and an inferior point 3230. Depending on the geometry of the cushion in this region, the mid-contact plane may be a tangent at both the superior and inferior points.

Figure 3X:
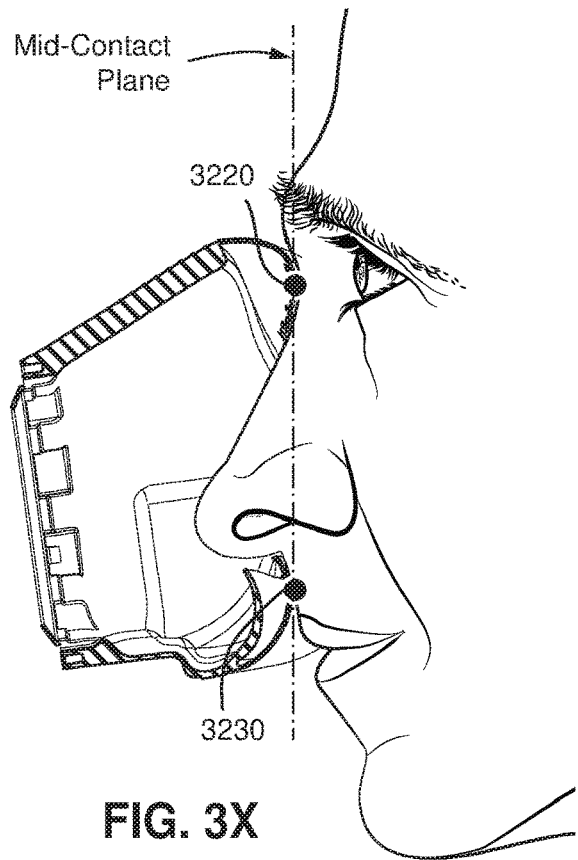

FIG. 3X shows the plenum chamber 3200 of FIG. 3U in position for use on a face. The sagittal plane of the plenum chamber 3200 generally coincides with the midsagittal plane of the face when the plenum chamber is in position for use. The mid-contact plane corresponds generally to the 'plane of the face' when the plenum chamber is in position for use. In FIG. 3X the plenum chamber 3200 is that of a nasal mask, and the superior point 3220 sits approximately on the sellion, while the inferior point 3230 sits on the lip superior.

4.4 RPT Device

Figure 4A:
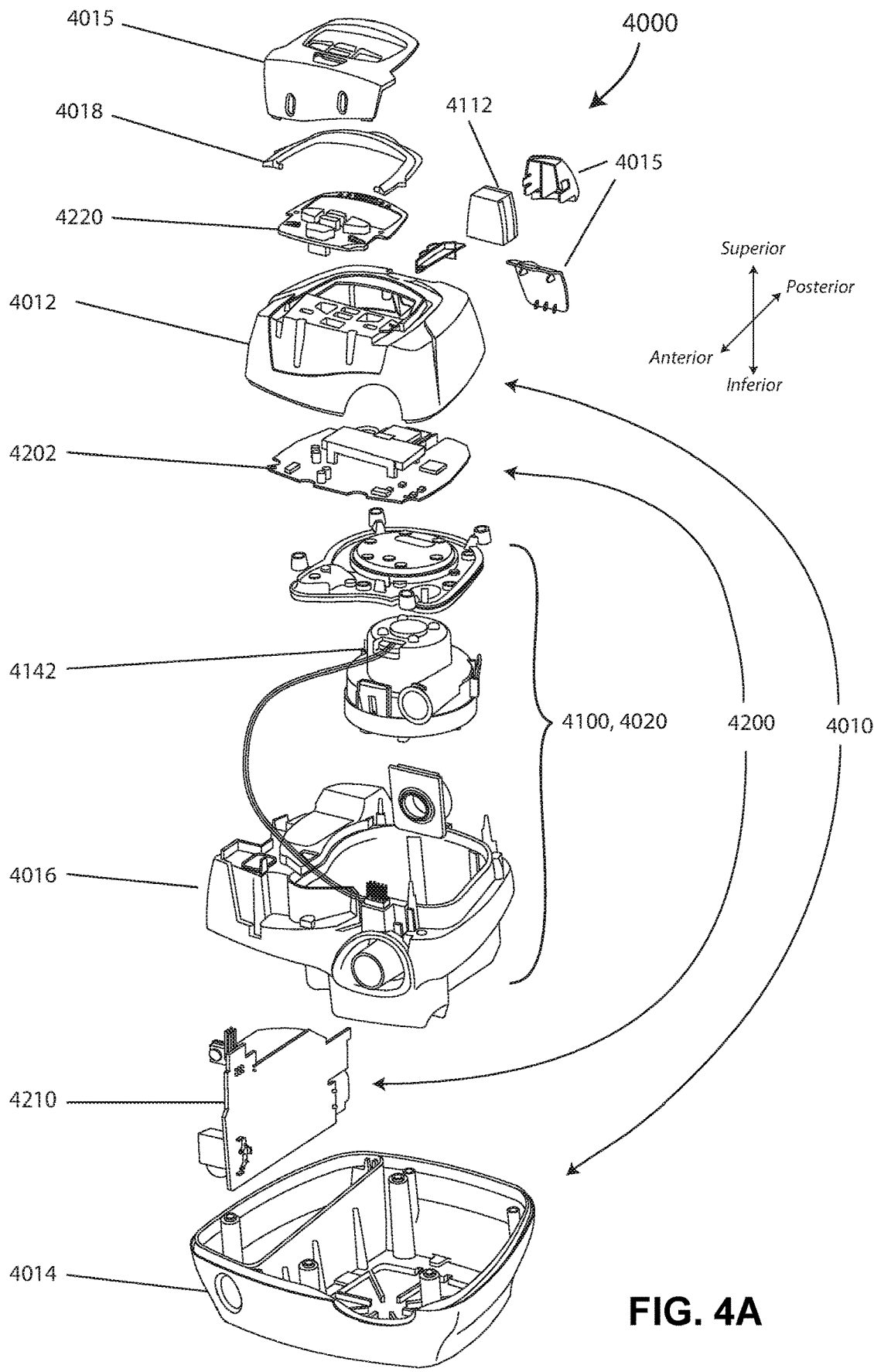

FIG. 4A shows an RPT device in accordance with one form of the present technology.

Figure 4B:
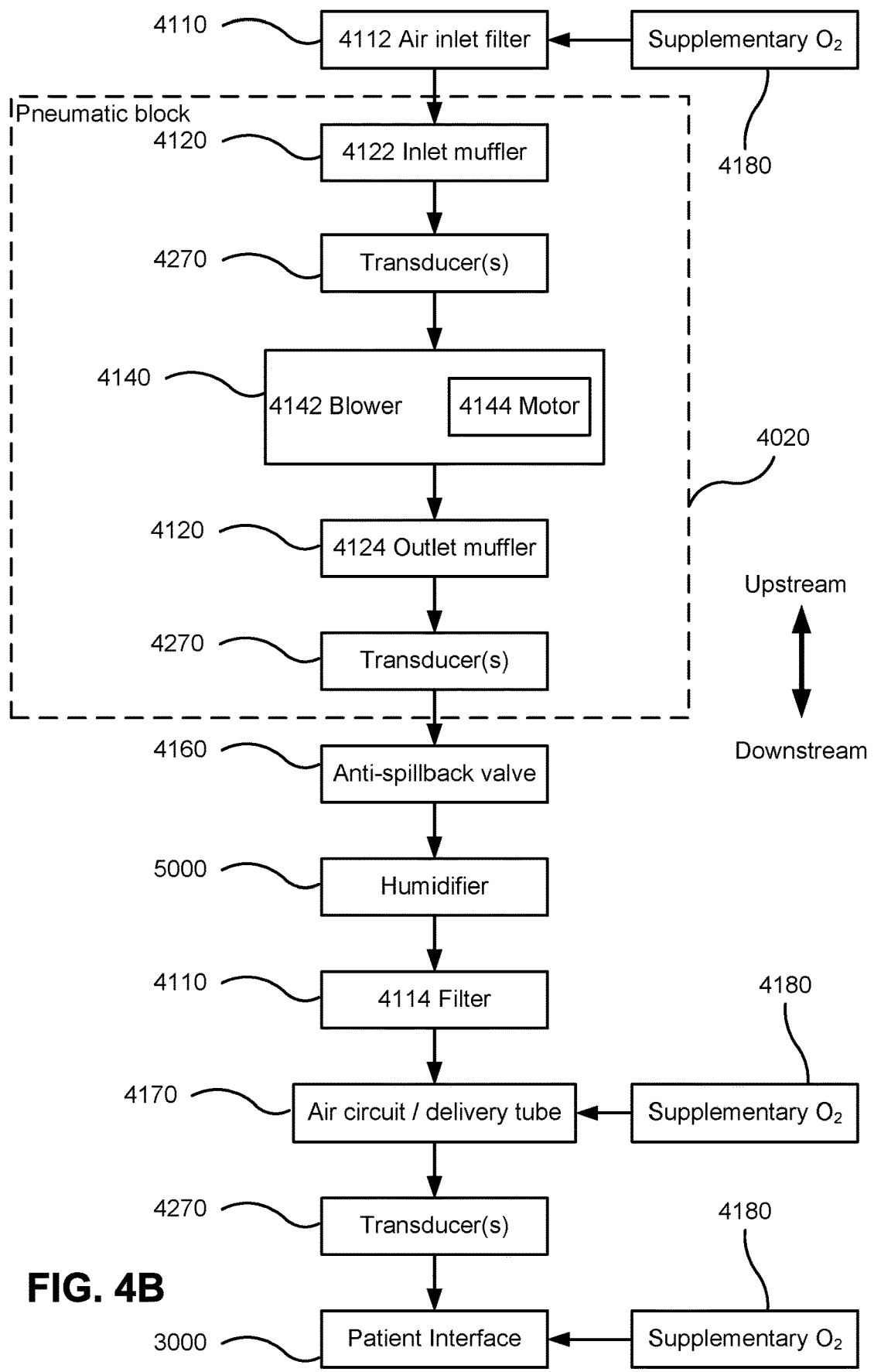

FIG. 4B is a schematic diagram of the pneumatic path of an RPT device in accordance with one form of the present technology. The directions of upstream and downstream are indicated with reference to the blower and the patient interface. The blower is defined to be upstream of the patient interface and the patient interface is defined to be downstream of the blower, regardless of the actual flow direction at any particular moment. Items which are located within the pneumatic path between the blower and the patient interface are downstream of the blower and upstream of the patient interface.

4.5 Breathing Waveforms

Figure 5:
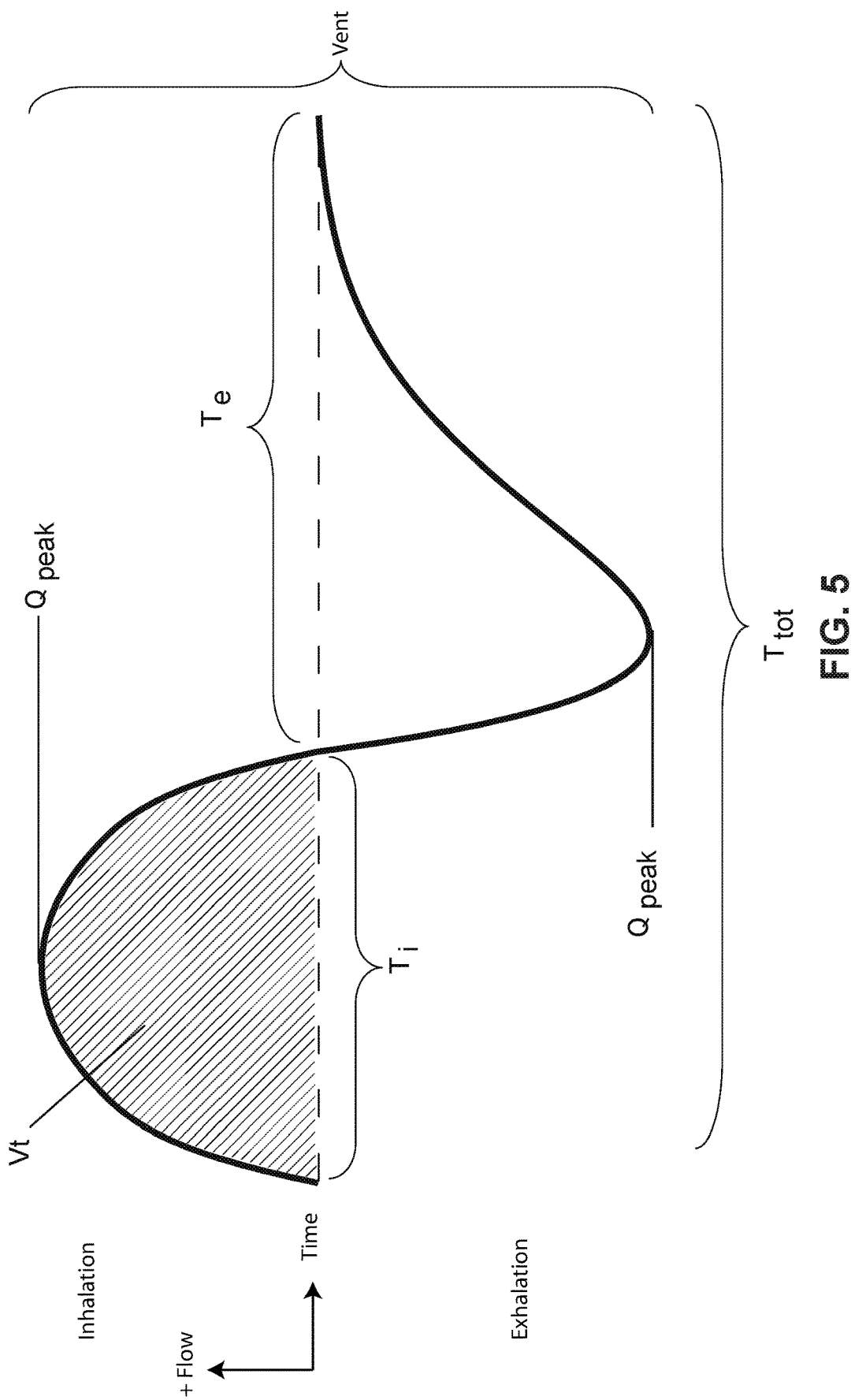

FIG. 5 shows a model typical breath waveform of a person while sleeping.

4.6 Patient Interface of the Present Technology

Figure 6A:
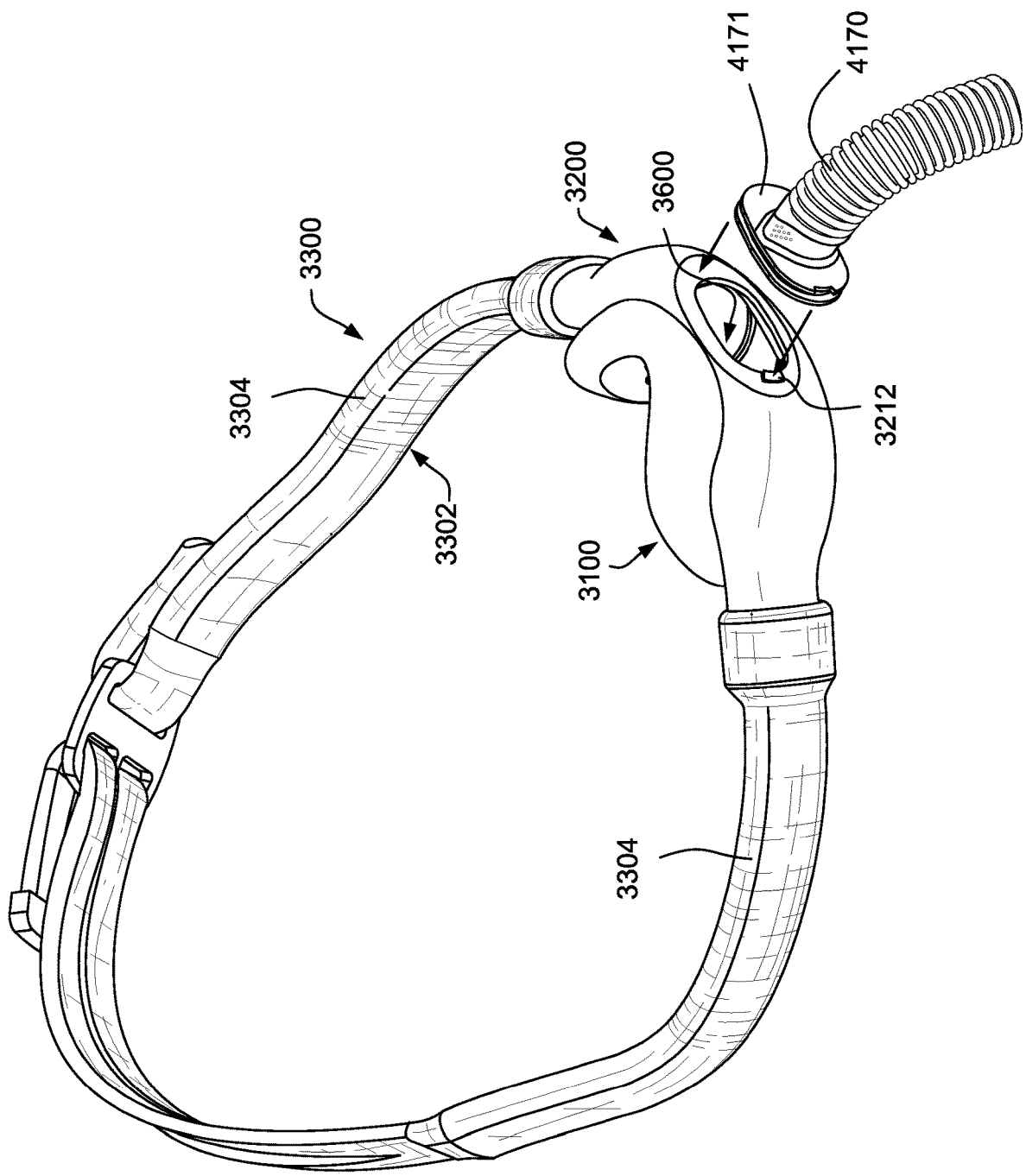

FIG. 6A shows a perspective view of an air circuit disconnected from a patient interface.

Figure 6B:
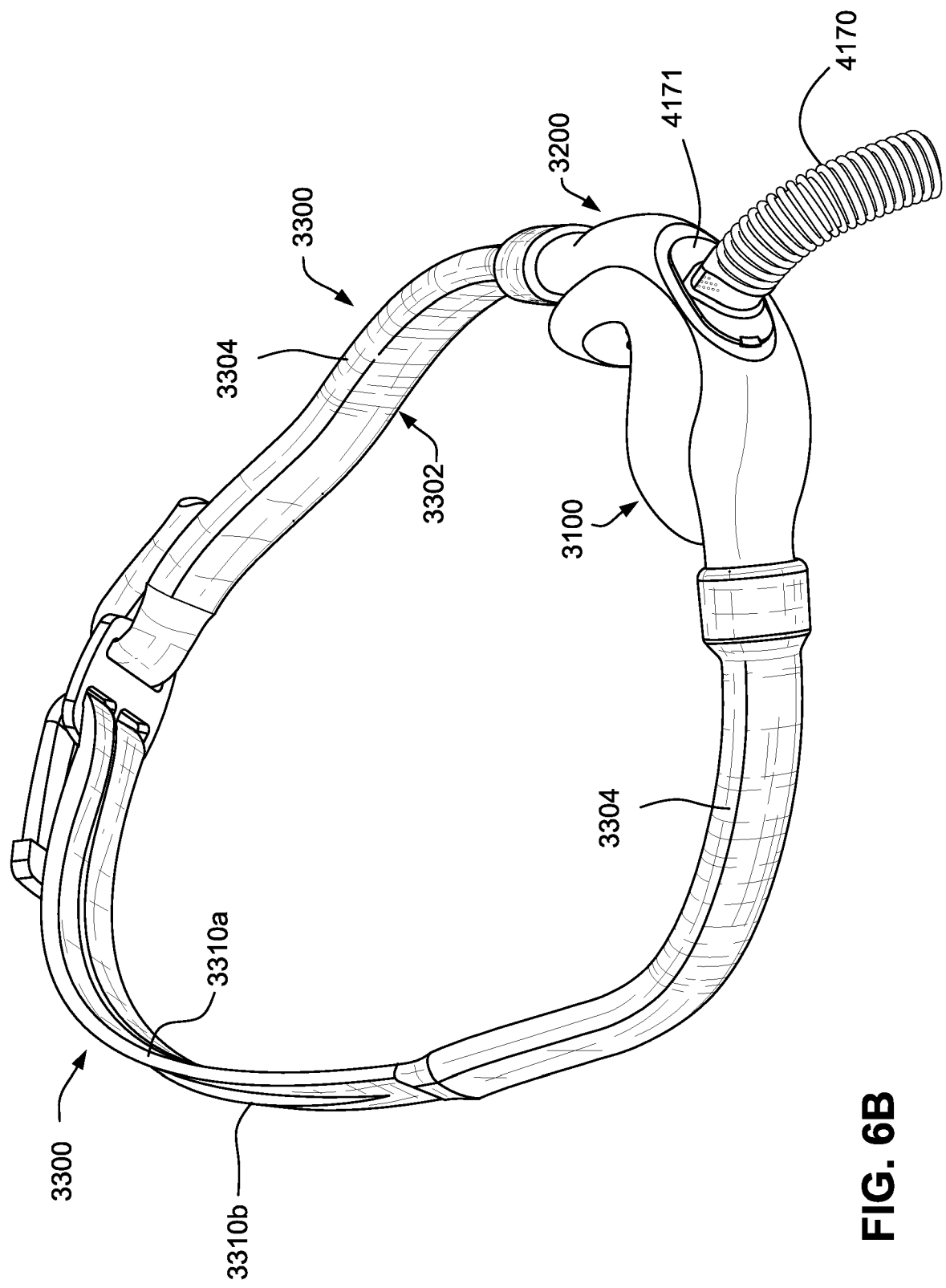

FIG. 6B shows a perspective view of the air circuit of FIG. 6A coupled to the patient interface.

Figure 6C:
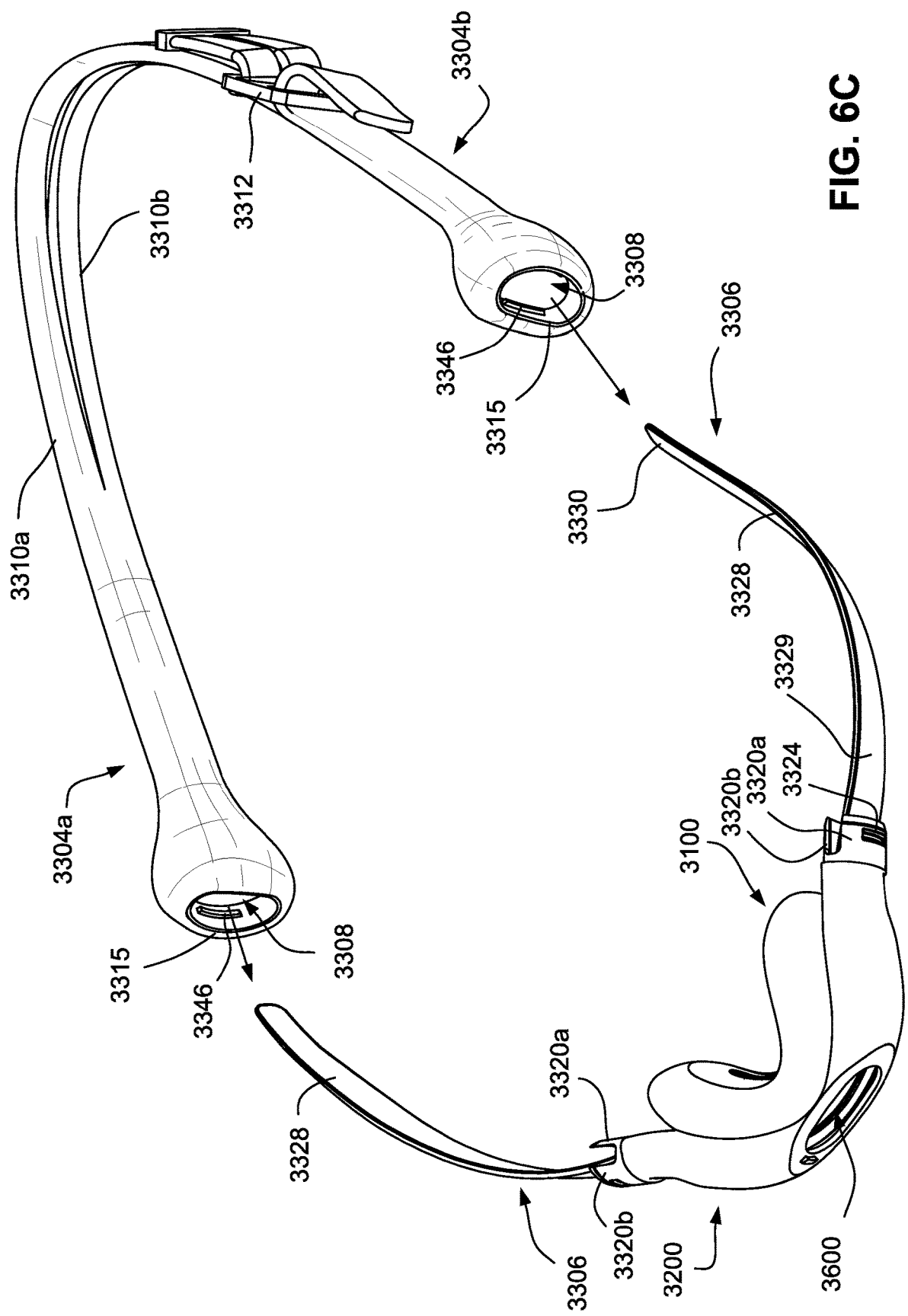

FIG. 6C shows a perspective view of the patient interface of FIG. 6A with a back strap exploded in order to illustrate a pair of arms.

Figure 6D:
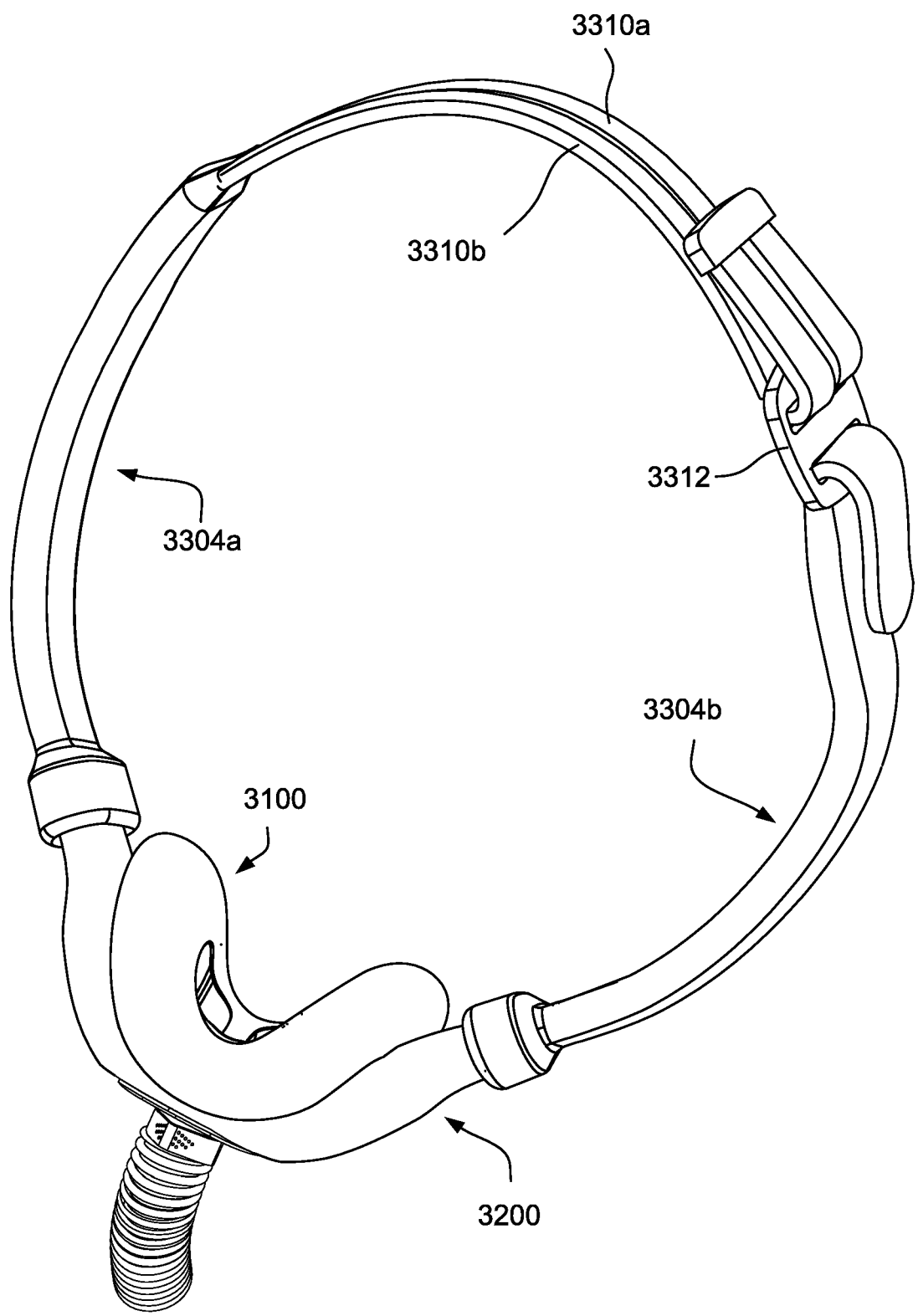

FIG. 6D shows a perspective view of the patient interface of FIG. 6A, with the back strap coupled to the pair of arms.

Figure 6E:
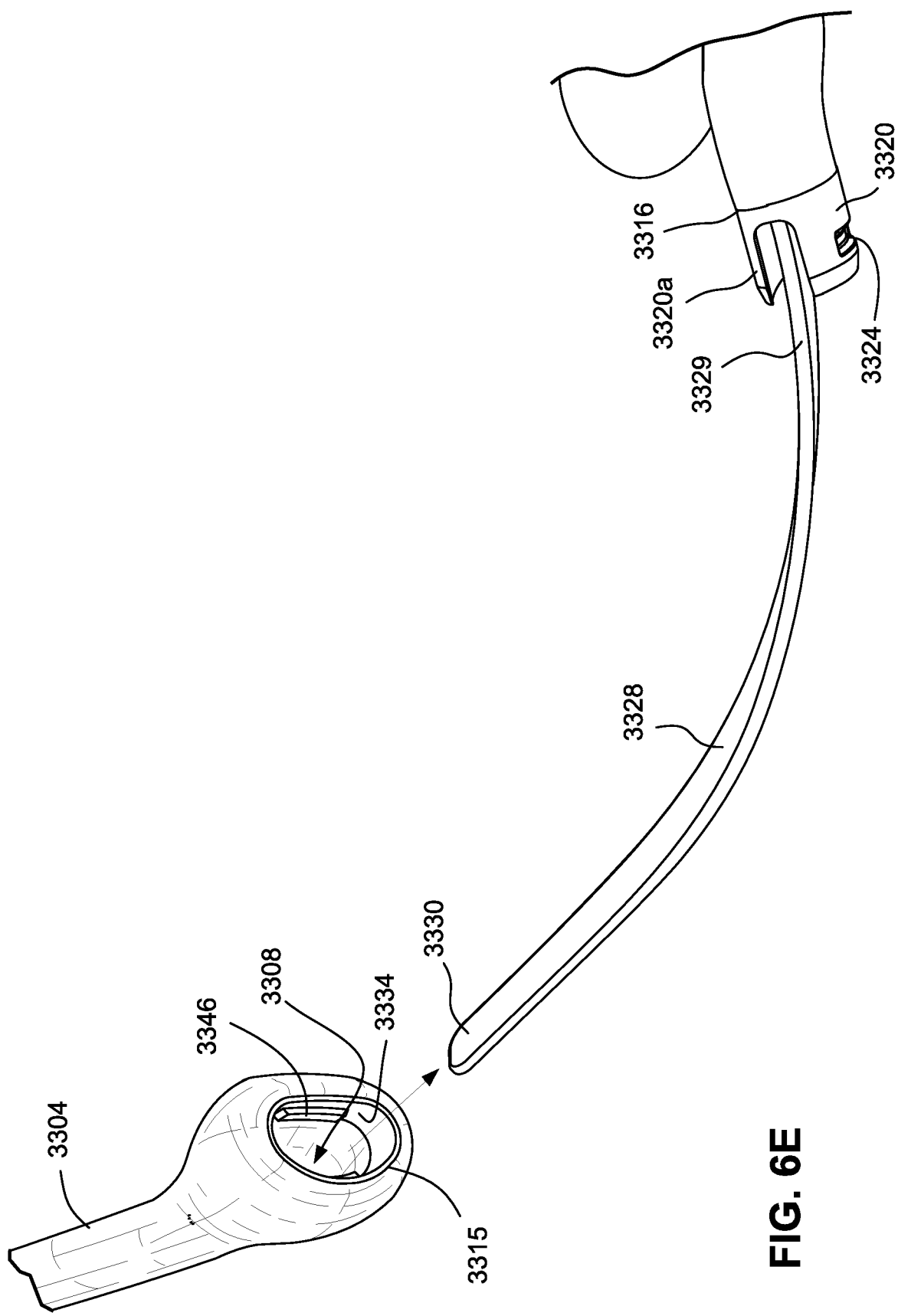

FIG. 6E shows a detail view of the patient interface of FIG. 6A, illustrating an arm of a positioning and stabilising structure, and a sleeve decoupled from the arm.

Figure 6F:
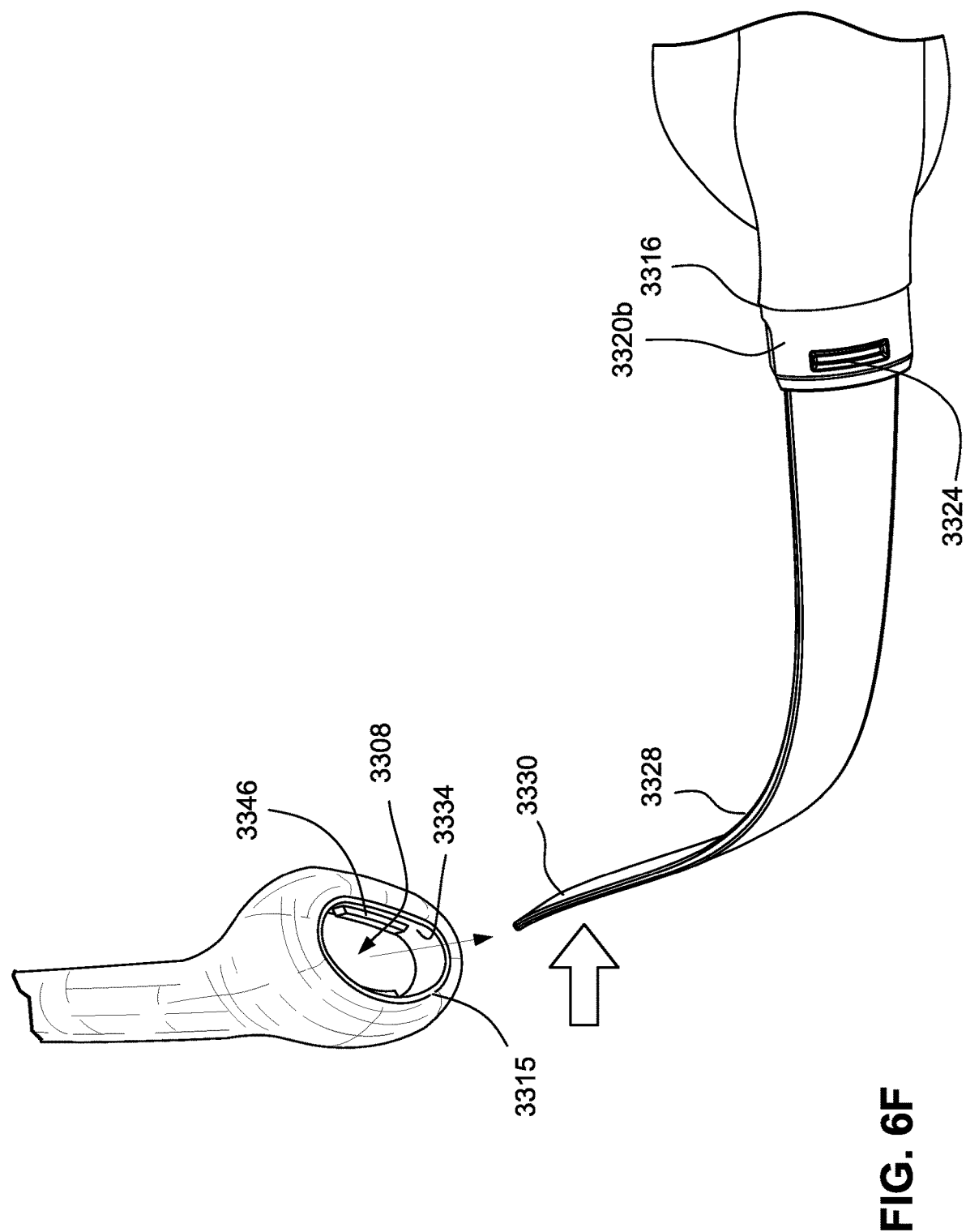

FIG. 6F shows a perspective view of the patient interface of FIG. 6E, illustrating the arm in a second bent position.

Figure 6G:
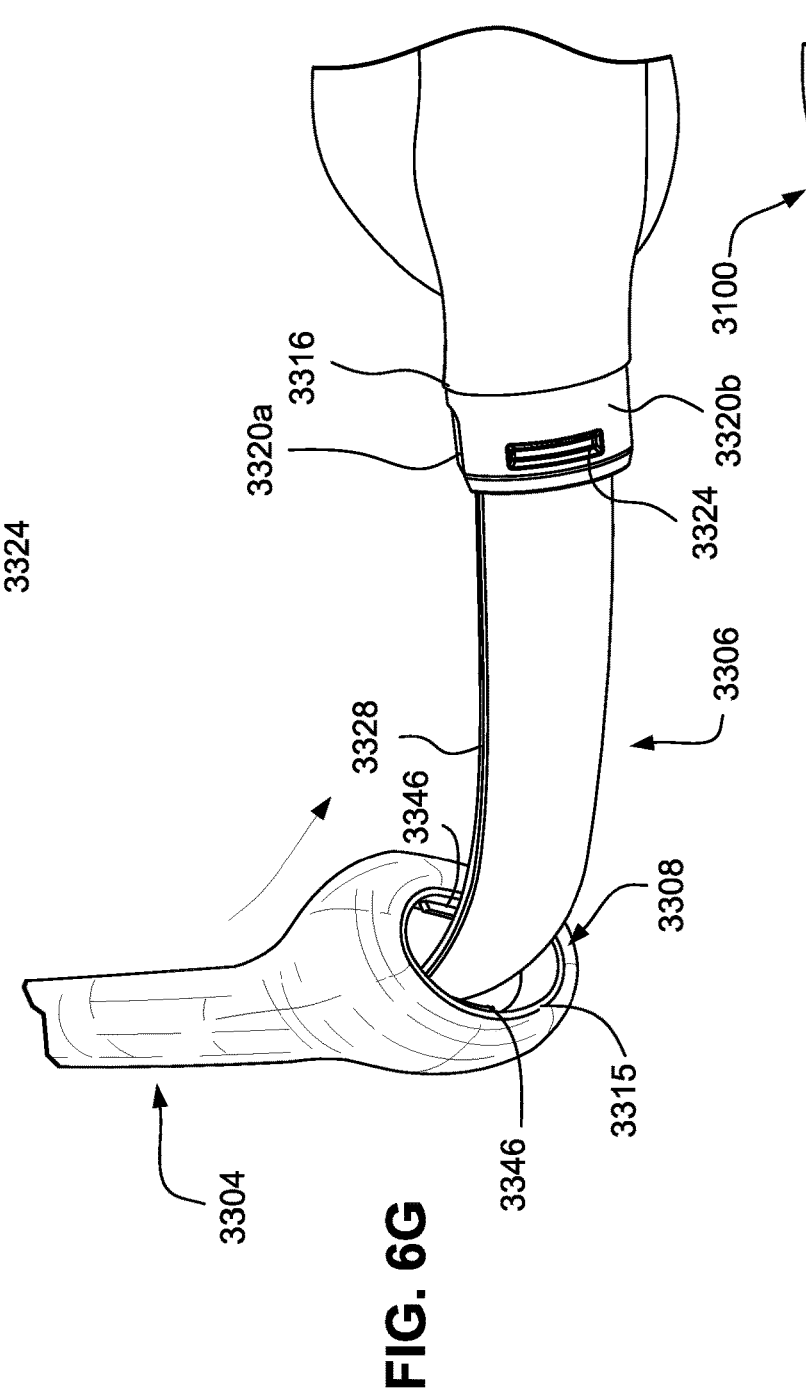

FIG. 6G shows a perspective view of the patient interface of FIG. 6A, illustrating the sleeve starting to be slide along the arm.

Figure 6H:
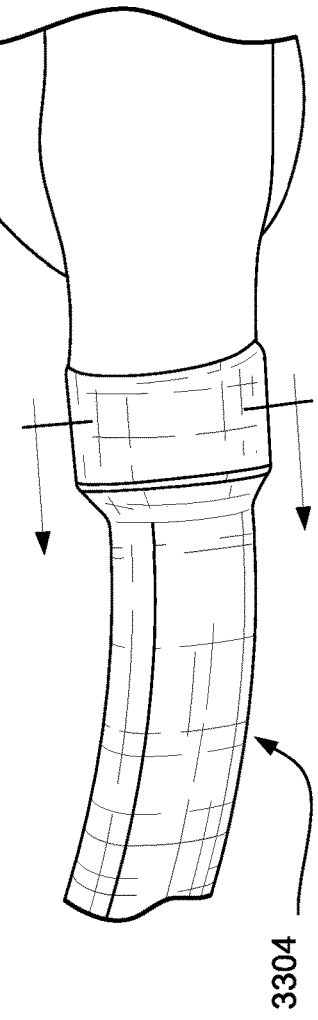

FIG. 6H shows a perspective view of the patient interface of FIG. 6A, illustrating the sleeve fully slid along the arm.

Figure 6I:
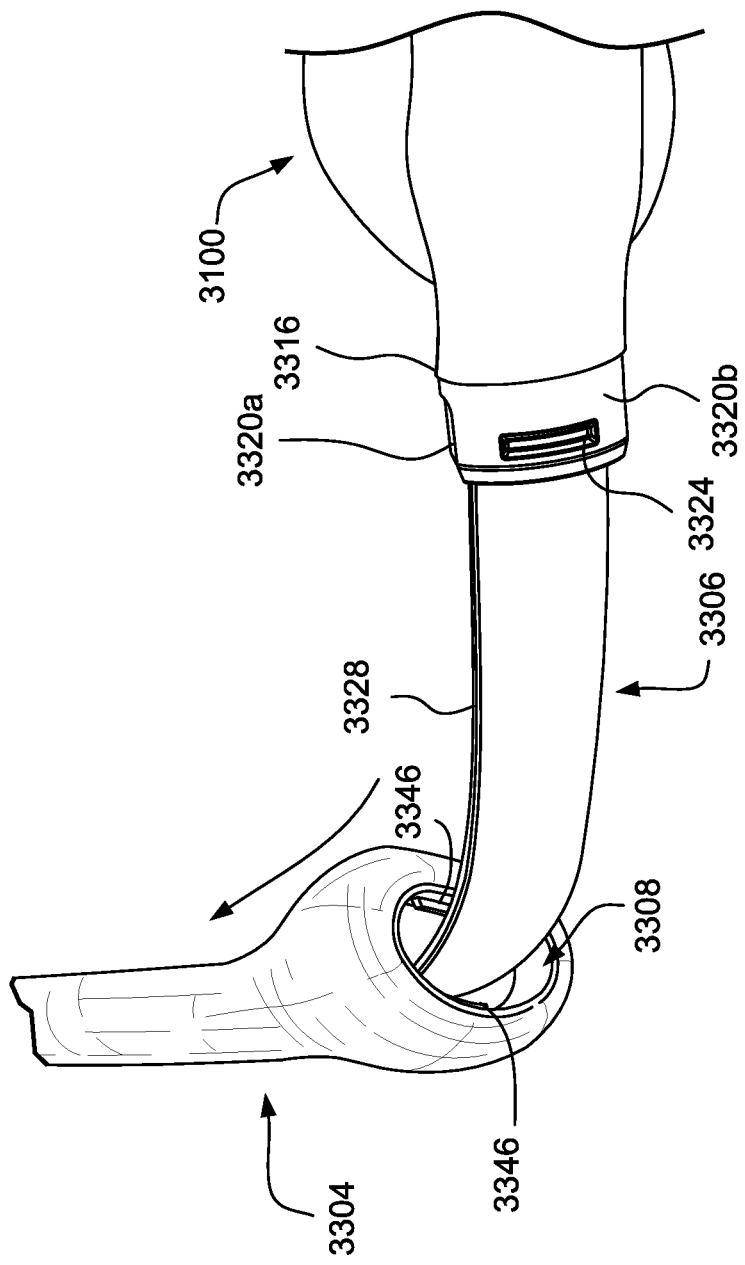

FIG. 6I shows a perspective view of the patient interface of FIG. 6A, illustrating the sleeve being removed from the arm.

Figure 6J:
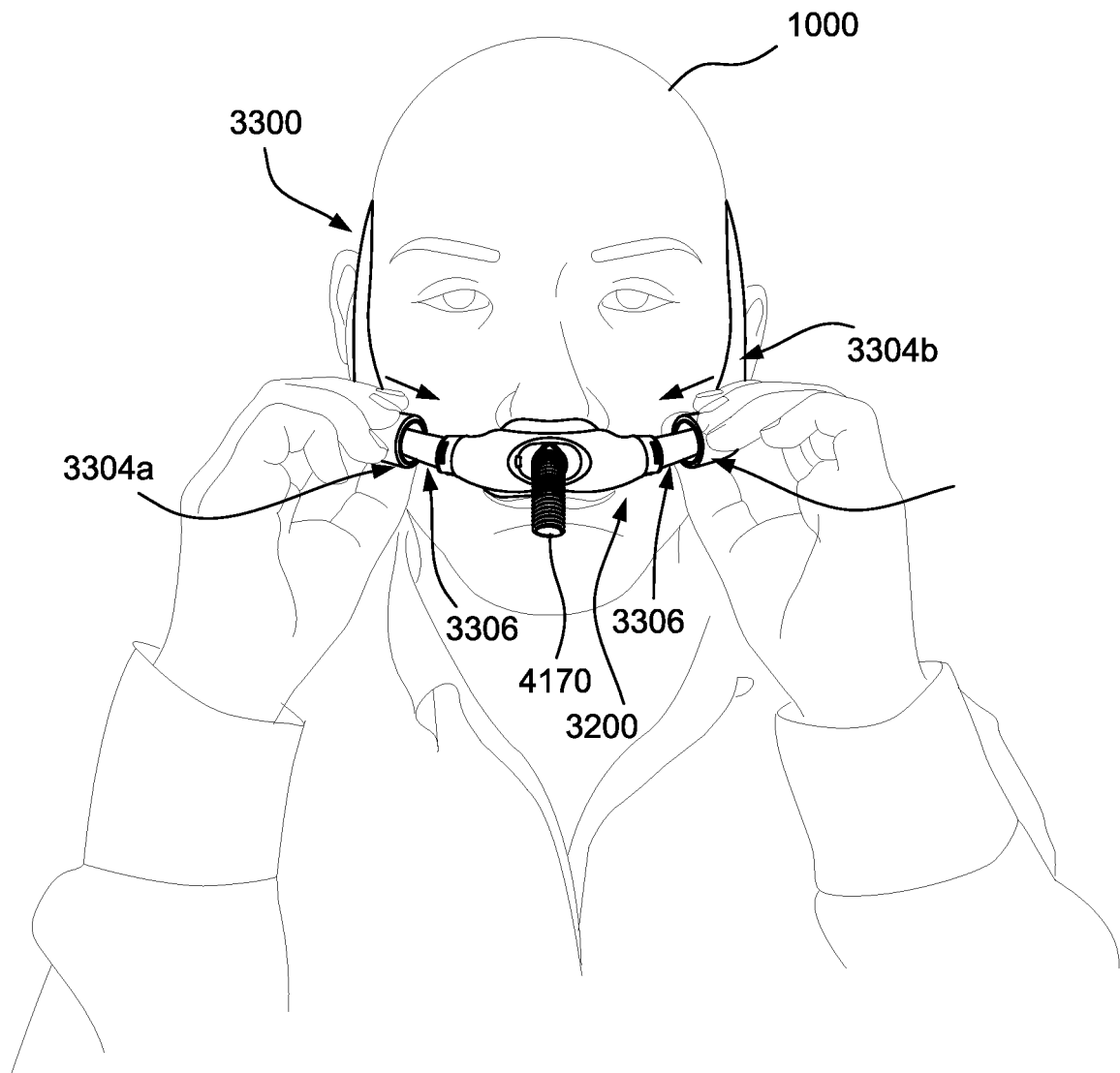

FIG. 6J shows a perspective view of a patient wearing the patient interface of FIG. 6A, illustrating the patient donning the patient interface by sliding the sleeve along the arms.

Figure 6K:
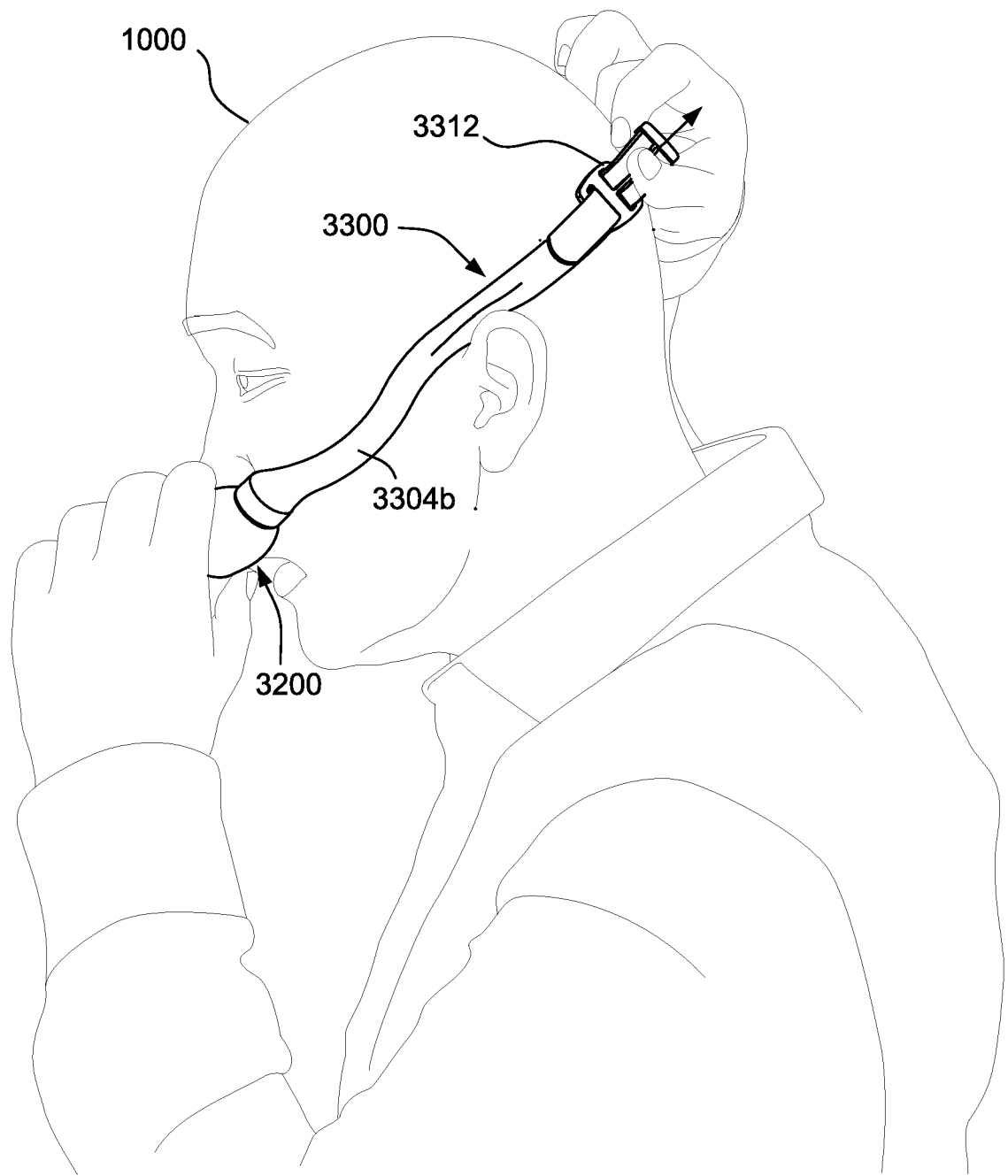

FIG. 6K shows a perspective view of a patient wearing the patient interface of FIG. 6A, illustrating the patient adjusting a length of the sleeve after the sleeve is coupled to a seal-forming structure.

Figure 6L:
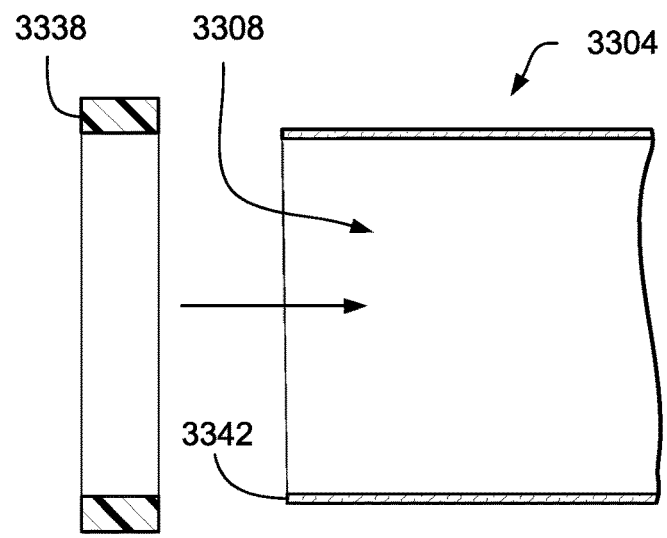

FIG. 6L shows a cross-sectional view of a sleeve of the patient interface of FIG. 6A, the sleeve in a disassembled position and an outer coupling being inserted into the sleeve.

Figure 6M:
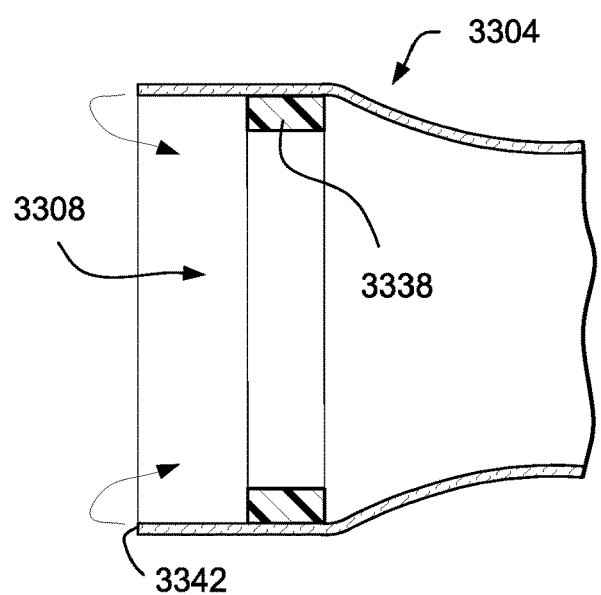

FIG. 6M is a cross-sectional view of the sleeve of FIG. 6L, and illustrating the outer coupling positioned within the sleeve and displaced from an end of the sleeve.

Figure 6N:
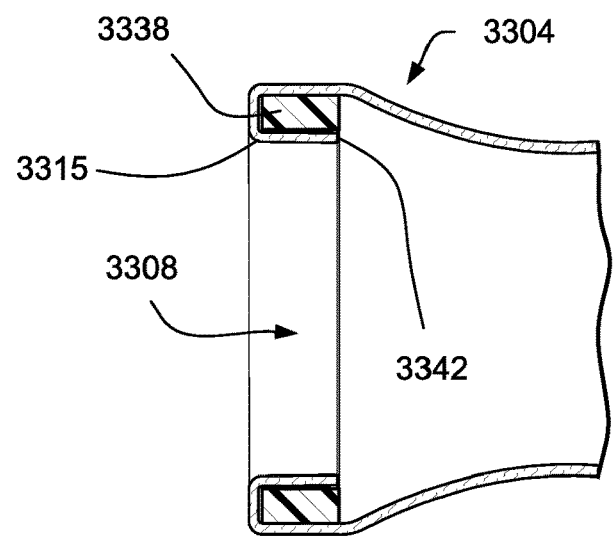

FIG. 6N is a cross-sectional view of the sleeve of FIG. 6M, and illustrating the end of the sleeve being folded into the sleeve and over the outer coupling.

Figure 6O:
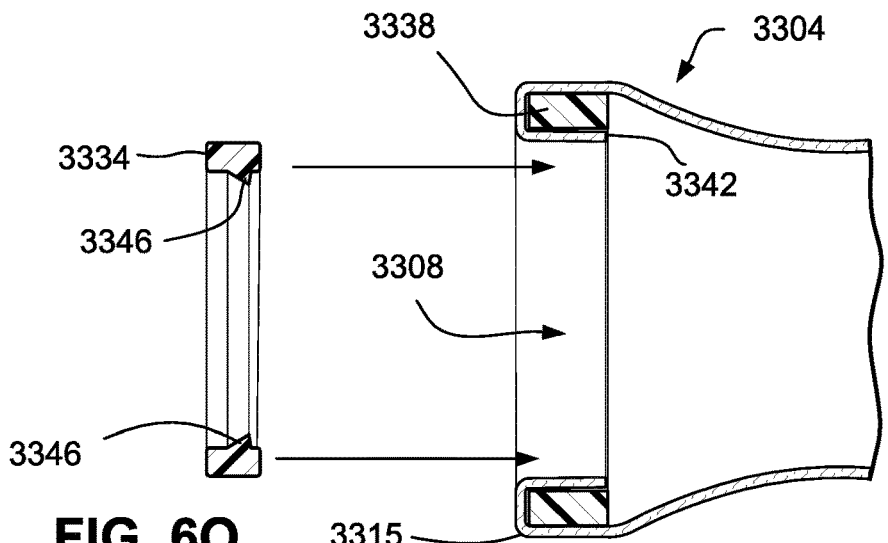

FIG. 6O is a cross-sectional view of the sleeve of FIG. 6M, and illustrating an inner coupling being inserted into the sleeve.

Figure 6P:
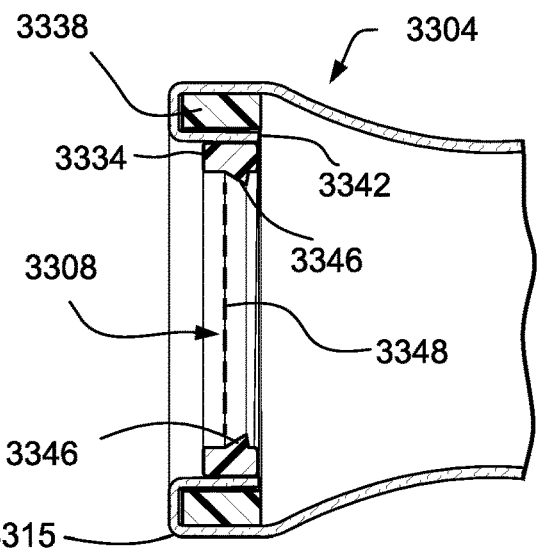

FIG. 6P is a cross-sectional view of the sleeve of FIG. 6M, and illustrating the inner coupling received within the sleeve.

Figure 6Q:
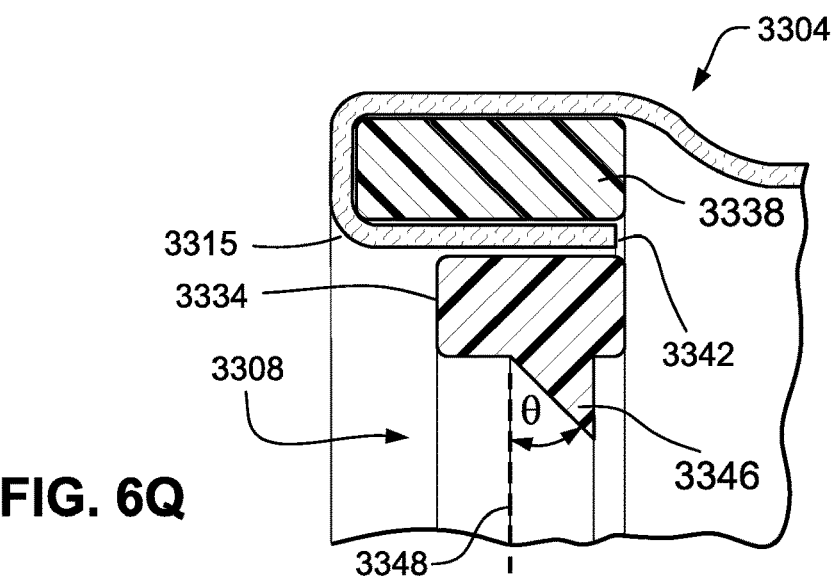

FIG. 6Q is a detail view of the sleeve of FIG. 6P, illustrating the angle of a projection.

Figure 6R:
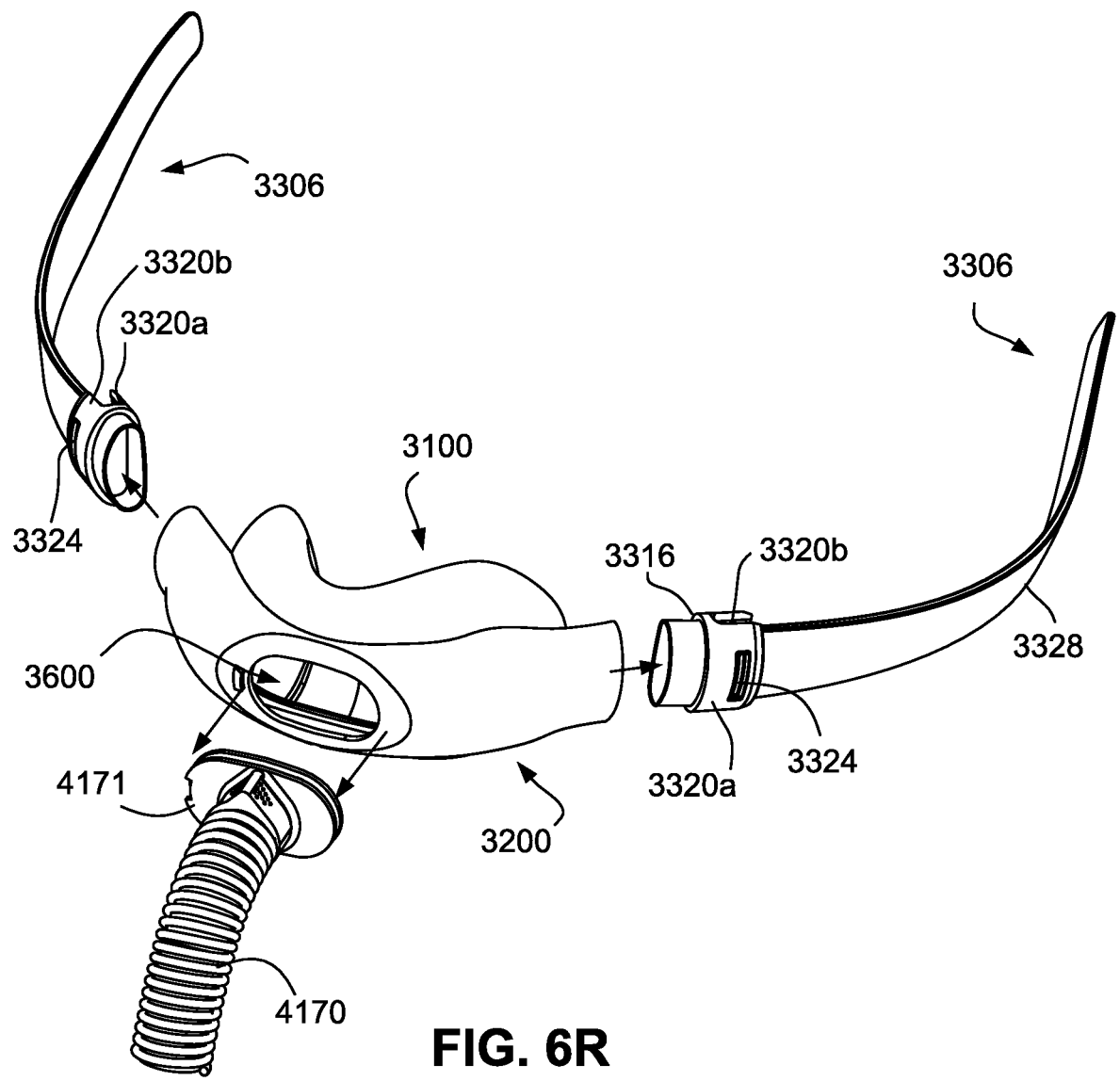

FIG. 6R is a perspective view of the patient interface of FIG. 6A, illustrating the air circuit and the arms being disconnected from the seal-forming structure.

Figure 6S:
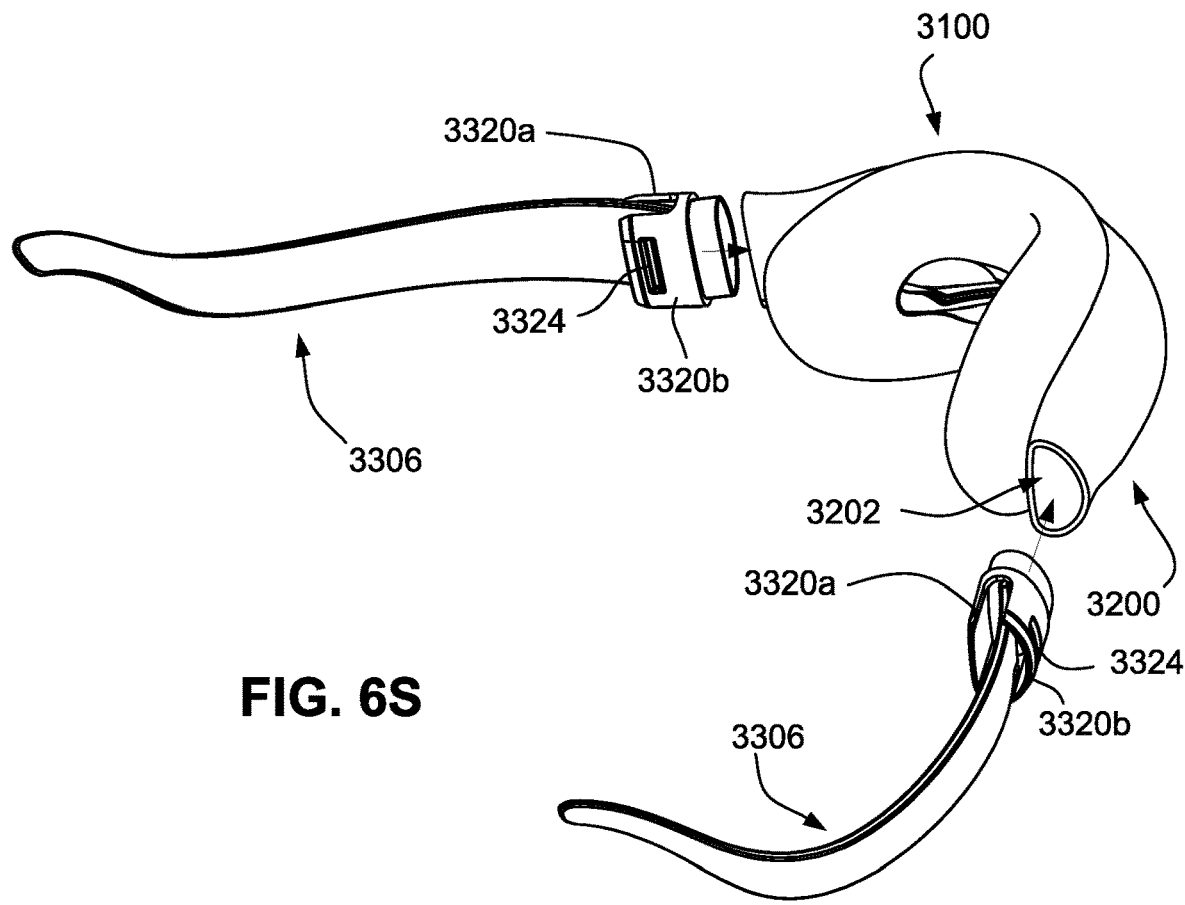

FIG. 6S is a rear perspective view of the seal-forming structure of FIG. 6R.

Figure 6T:
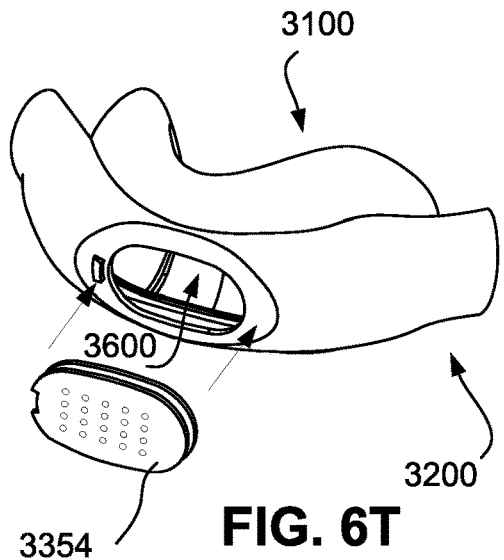

FIG. 6T is a perspective view of the seal-forming structure of FIG. 6R, illustrating a plug being inserted into an opening of the seal-forming structure.

Figure 6U:
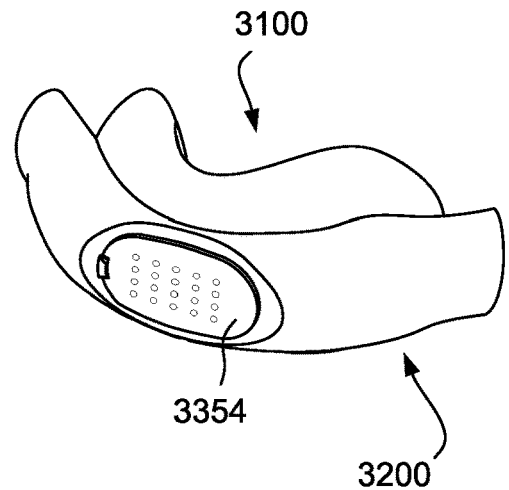

FIG. 6U is a perspective view of the seal-forming structure of FIG. 6T, illustrating the plug being inserted into the opening of the seal-forming structure.

Figure 6V:
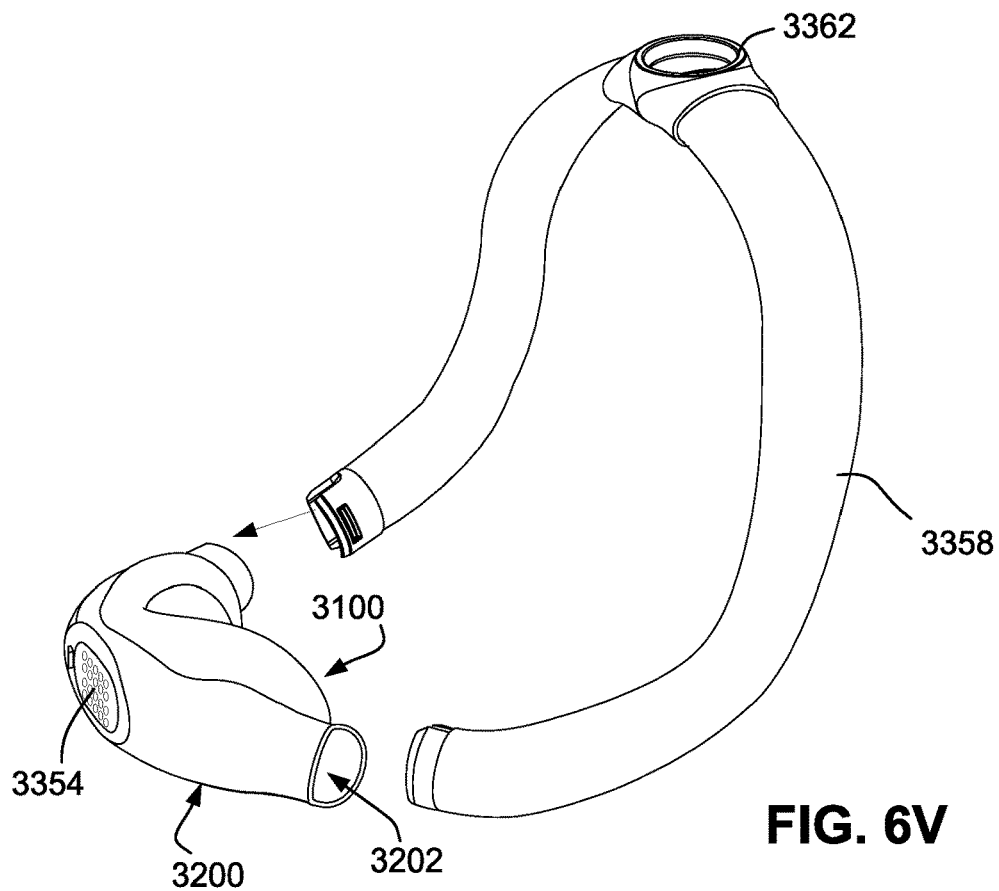

FIG. 6V is a perspective view of conduit headgear being coupled to the seal-forming structure of FIG. 6T.

Figure 6W:
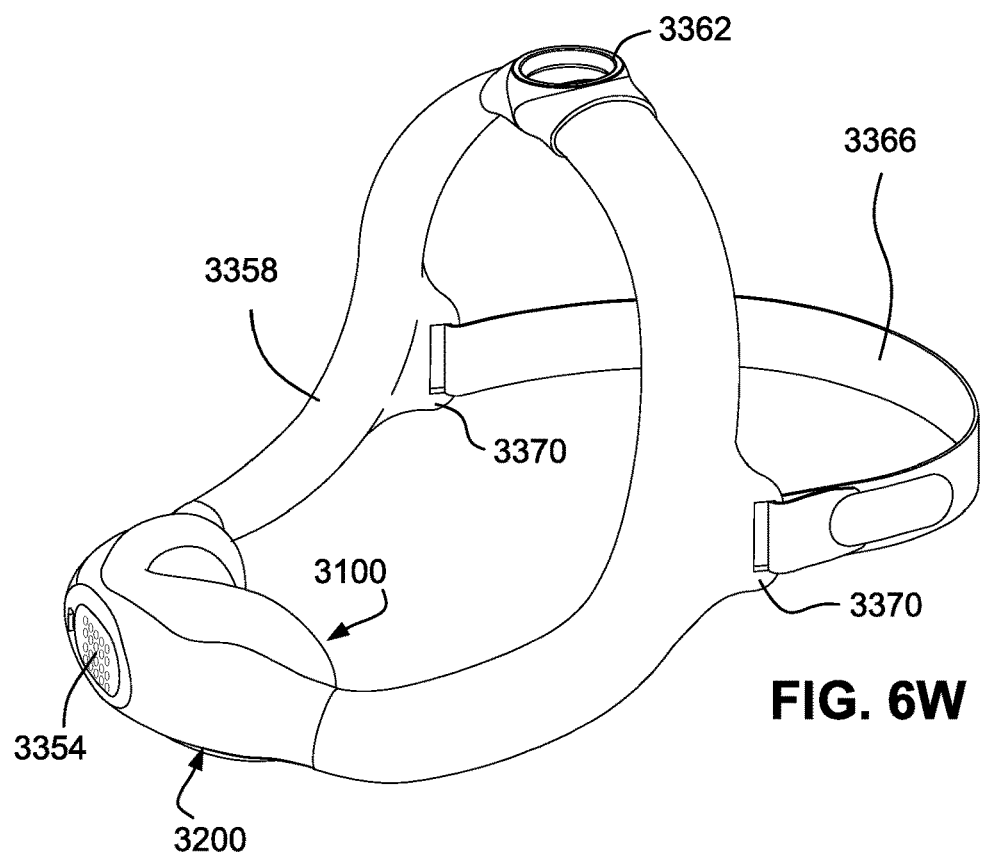

FIG. 6W is a perspective view of the conduit headgear coupled to the seal-forming structure of FIG. 6T.

5 DETAILED DESCRIPTION OF EXAMPLES OF THE TECHNOLOGY

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

The following description is provided in relation to various examples which may share one or more common characteristics and/or features. It is to be understood that one or more features of any one example may be combinable with one or more features of another example or other examples. In addition, any single feature or combination of features in any of the examples may constitute a further example.

5.1 Therapy

In one form, the present technology comprises a method for treating a respiratory disorder comprising applying positive pressure to the entrance of the airways of a patient 1000.

In certain examples of the present technology, a supply of air at positive pressure is provided to the nasal passages of the patient via one or both nares.

In certain examples of the present technology, mouth breathing is limited, restricted or prevented.

5.2 Respiratory Therapy Systems

In one form, the present technology comprises a respiratory therapy system for treating a respiratory disorder. The respiratory therapy system may comprise an RPT device 4000 for supplying a flow of air to the patient 1000 via an air circuit 4170 and a patient interface 3000.

In one form, the present technology comprises a face-contacting system for interacting with a user's face. The system may comprise a facial interface that engages or contacts the user's face. The facial interface may include a patient interface 3000, or any other system that interacts with a user's face.

5.3 Patient Interface

A face-contacting system may include a facial interface that is configured to be positioned against or near a user's face. The facial interface is positioned and arranged to interact with an anatomical feature on the user's face. One example of the facial interface is a non-invasive patient interface 3000.

A non-invasive patient interface 3000 in accordance with one aspect of the present technology comprises the following functional aspects: a seal-forming structure 3100, a plenum chamber 3200, a positioning and stabilising structure 3300, a vent 3400, one form of connection port 3600 for connection to air circuit 4170, and a forehead support 3700. In some forms a functional aspect may be provided by one or more physical components. In some forms, one physical component may provide one or more functional aspects. In use the seal-forming structure 3100 is arranged to surround an entrance to the airways of the patient so as to maintain positive pressure at the entrance(s) to the airways of the patient 1000. The sealed patient interface 3000 is therefore suitable for delivery of positive pressure therapy.

If a patient interface is unable to comfortably deliver a minimum level of positive pressure to the airways, the patient interface may be unsuitable for respiratory pressure therapy.

The patient interface 3000 in accordance with one form of the present technology is constructed and arranged to be able to provide a supply of air at a positive pressure of at least 6 cmH$_2$O with respect to ambient.

The patient interface 3000 in accordance with one form of the present technology is constructed and arranged to be able to provide a supply of air at a positive pressure of at least 10 cmH$_2$O with respect to ambient.

The patient interface 3000 in accordance with one form of the present technology is constructed and arranged to be able to provide a supply of air at a positive pressure of at least 20 cmH$_2$O with respect to ambient.

5.3.1 Seal-Forming Structure

In one form of the present technology, a seal-forming structure 3100 provides a target seal-forming region, and may additionally provide a cushioning function. The seal-forming structure 3100 may also be referred to as a cushion. In other examples of a face-contacting system, the cushion may contact the user's face and may not seal against the user's face. The target seal-forming region is a region on the seal-forming structure 3100 where sealing may occur. The region where sealing actually occurs—the actual sealing surface—may change within a given treatment session, from day to day, and from patient to patient, depending on a range of factors including for example, where the patient interface was placed on the face, tension in the positioning and stabilising structure and the shape of a patient's face.

In one form the target seal-forming region is located on an outside surface of the seal-forming structure 3100.

In certain forms of the present technology, the seal-forming structure 3100 is constructed from a biocompatible material, e.g. silicone rubber.

A seal-forming structure 3100 in accordance with the present technology may be constructed from a soft, flexible, resilient material such as silicone.

In certain forms of the present technology, a system is provided comprising more than one a seal-forming structure 3100, each being configured to correspond to a different size and/or shape range. For example the system may comprise one form of a seal-forming structure 3100 suitable for a large sized head, but not a small sized head and another suitable for a small sized head, but not a large sized head.

5.3.1.1 Sealing Mechanisms

In one form, the seal-forming structure includes a sealing flange utilizing a pressure assisted sealing mechanism. In use, the sealing flange can readily respond to a system positive pressure in the interior of the plenum chamber 3200 acting on its underside to urge it into tight sealing engagement with the face. The pressure assisted mechanism may act in conjunction with elastic tension in the positioning and stabilising structure.

In one form, the seal-forming structure 3100 comprises a sealing flange and a support flange. The sealing flange comprises a relatively thin member with a thickness of less than about 1 mm, for example about 0.25 mm to about 0.45 mm, which extends around the perimeter of the plenum chamber 3200. Support flange may be relatively thicker than the sealing flange. The support flange is disposed between the sealing flange and the marginal edge of the plenum chamber 3200, and extends at least part of the way around the perimeter. The support flange is or includes a spring-like element and functions to support the sealing flange from buckling in use.

In one form, the seal-forming structure may comprise a compression sealing portion or a gasket sealing portion. In use the compression sealing portion, or the gasket sealing portion is constructed and arranged to be in compression, e.g. as a result of elastic tension in the positioning and stabilising structure.

In one form, the seal-forming structure comprises a tension portion. In use, the tension portion is held in tension, e.g. by adjacent regions of the sealing flange.

In one form, the seal-forming structure comprises a region having a tacky or adhesive surface.

In certain forms of the present technology, a seal-forming structure may comprise one or more of a pressure-assisted sealing flange, a compression sealing portion, a gasket sealing portion, a tension portion, and a portion having a tacky or adhesive surface.

5.3.1.2 Nose Bridge or Nose Ridge Region

In one form, the non-invasive patient interface 3000 comprises a seal-forming structure that forms a seal in use on a nose bridge region or on a nose-ridge region of the patient's face.

In one form, the seal-forming structure includes a saddle-shaped region constructed to form a seal in use on a nose bridge region or on a nose-ridge region of the patient's face.

5.3.1.3 Upper Lip Region

In one form, the non-invasive patient interface 3000 comprises a seal-forming structure that forms a seal in use on an upper lip region (that is, the lip superior) of the patient's face.

In one form, the seal-forming structure includes a saddle-shaped region constructed to form a seal in use on an upper lip region of the patient's face.

5.3.1.4 Chin-Region

In one form the non-invasive patient interface 3000 comprises a seal-forming structure that forms a seal in use on a chin-region of the patient's face.

In one form, the seal-forming structure includes a saddle-shaped region constructed to form a seal in use on a chin-region of the patient's face.

5.3.1.5 Forehead Region

In one form, the seal-forming structure that forms a seal in use on a forehead region of the patient's face. In such a form, the plenum chamber may cover the eyes in use.

5.3.1.6 Nasal Pillows

In one form (see e.g., FIG. 3G), the seal-forming structure of the non-invasive patient interface 3000 comprises a pair of nasal puffs, or nasal pillows, each nasal puff or nasal pillow being constructed and arranged to form a seal with a respective naris of the nose of a patient.

Nasal pillows in accordance with an aspect of the present technology include: a frusto-cone, at least a portion of which forms a seal on an underside of the patient's nose, a stalk, a flexible region on the underside of the frusto-cone and connecting the frusto-cone to the stalk. In addition, the structure to which the nasal pillow of the present technology is connected includes a flexible region adjacent the base of the stalk. The flexible regions can act in concert to facilitate a universal joint structure that is accommodating of relative movement both displacement and angular of the frusto-cone and the structure to which the nasal pillow is connected. For example, the frusto-cone may be axially displaced towards the structure to which the stalk is connected.

5.3.1.7 Under the Nose Mask

As shown in FIGS. 6A-6C, the seal-forming structure 3100 of the patient interface 3000 comprises an under the nose mask, which may be similar to the nasal pillows because a seal is formed proximate the patient's nostrils and leaves the patient's mouth exposed to the ambient. The seal-forming structure 3100 in the form of an under the nose mask seals around an outer surface of the patient's nose.

In the illustrated form, the seal-forming structure 3100 may seal around the outside of the nose and may include a single opening for each nostril. In other forms, the seal-forming structure 3100 may include a single opening that receives both nostrils.

5.3.2 Plenum Chamber

The plenum chamber 3200 has a perimeter that is shaped to be complementary to the surface contour of the face of an average person in the region where a seal will form in use. In use, a marginal edge of the plenum chamber 3200 is positioned in close proximity to an adjacent surface of the face. Actual contact with the face is provided by the seal-forming structure 3100. The seal-forming structure 3100 may extend in use about the entire perimeter of the plenum chamber 3200. In some forms, the plenum chamber 3200 and the seal-forming structure 3100 are formed from a single homogeneous piece of material.

In certain forms of the present technology, the plenum chamber 3200 does not cover the eyes of the patient in use. In other words, the eyes are outside the pressurised volume defined by the plenum chamber. Such forms tend to be less obtrusive and/or more comfortable for the wearer, which can improve compliance with therapy.

In certain forms of the present technology, the plenum chamber 3200 is constructed from a transparent material, e.g. a transparent polycarbonate. The use of a transparent material can reduce the obtrusiveness of the patient interface, and help improve compliance with therapy. The use of a transparent material can aid a clinician to observe how the patient interface is located and functioning.

In certain forms of the present technology, the plenum chamber 3200 is constructed from a translucent material. The use of a translucent material can reduce the obtrusiveness of the patient interface, and help improve compliance with therapy.

As shown in FIGS. 6A and 6B, the plenum chamber 3200 includes an opening or connection port 3600. While exposed, the connection port 3600 provides fluid communication between the ambient and the nostrils, even when the seal-forming structure 3100 is sealed to the patient's face. In the illustrated form, the connection port 3600 defines an elliptical shape, and is disposed in a center of the plenum chamber 3200. In other forms, the connection port 3600 may have a different size or may define a different shape.

The connection port 3600 defines an opening for receiving a flow of pressurized fluid. Specifically, the air circuit 4170 is connectable to the connection port 3600 in order to provide a fluid path from a RPT device 4000 to the patient's airways. In the illustrated form, a projection 3212 is coupled to the plenum chamber 3200, and extends into the connection port 3600 (see e.g., FIG. 6A). The projection 3212 may connect to the air circuit 4170 and retain the air circuit 4170 with respect to the plenum chamber 3200. For example, the air circuit may include a ring 4171 formed from a rigid or semi-rigid material (e.g., plastic). When the air circuit 4170 is completely connected to the plenum chamber 3200 (see e.g., FIG. 6B), the projection 3212 engages the ring 4171 in a snap-fit arrangement (e.g., engagement of the projection 3212 creates a substantially airtight seal, which can be broken by providing a pulling force).

As shown in FIG. 6B, once the air circuit 4170 is coupled to the plenum chamber 3200, substantially no air is able to escape through the interface between the plenum chamber 3200 and the ring 4171. Air may be supplied directly into the plenum chamber 3200 from the air circuit 4170, in order to allow the patient to inhale pressurized air through their nose (or mouth if an alternate mask is used).

5.3.3 Positioning and Stabilising Structure

The positioning and stabilising structure 3300 may be generally referred to as a structure that maintains the position of the facial interface in a desired position on the user's face.

In some forms, a single positioning and stabilising structure 3300 may be usable with multiple types of facial interfaces. Other forms of positioning and stabilising structures may be usable only with a single type of facial interface.

The seal-forming structure 3100 of the patient interface 3000 of the present technology may be held in sealing position in use by the positioning and stabilising structure 3300.

In one form the positioning and stabilising structure 3300 provides a retention force at least sufficient to overcome the effect of the positive pressure in the plenum chamber 3200 to lift off the face.

In one form the positioning and stabilising structure 3300 provides a retention force to overcome the effect of the gravitational force on the patient interface 3000.

In one form the positioning and stabilising structure 3300 provides a retention force as a safety margin to overcome the potential effect of disrupting forces on the patient interface 3000, such as from tube drag, or accidental interference with the patient interface.

In one form of the present technology, a positioning and stabilising structure 3300 is provided that is configured in a manner consistent with being worn by a patient while sleeping. In one example the positioning and stabilising structure 3300 has a low profile, or cross-sectional thickness, to reduce the perceived or actual bulk of the apparatus. In one example, the positioning and stabilising structure 3300 comprises at least one strap having a rectangular cross-section. In one example the positioning and stabilising structure 3300 comprises at least one flat strap.

In one form of the present technology, a positioning and stabilising structure 3300 is provided that is configured so as not to be too large and bulky to prevent the patient from lying in a supine sleeping position with a back region of the patient's head on a pillow.

In one form of the present technology, a positioning and stabilising structure 3300 is provided that is configured so as not to be too large and bulky to prevent the patient from lying in a side sleeping position with a side region of the patient's head on a pillow.

In one form of the present technology, a positioning and stabilising structure 3300 is provided with a decoupling portion located between an anterior portion of the positioning and stabilising structure 3300, and a posterior portion of the positioning and stabilising structure 3300. The decoupling portion does not resist compression and may be, e.g. a flexible or floppy strap. The decoupling portion is constructed and arranged so that when the patient lies with their head on a pillow, the presence of the decoupling portion prevents a force on the posterior portion from being transmitted along the positioning and stabilising structure 3300 and disrupting the seal.

In one form of the present technology, a positioning and stabilising structure 3300 comprises a strap constructed from a laminate of a fabric patient-contacting layer, a foam inner layer and a fabric outer layer. In one form, the foam is porous to allow moisture, (e.g., sweat), to pass through the strap. In one form, the fabric outer layer comprises loop material to engage with a hook material portion.

In certain forms of the present technology, a positioning and stabilising structure 3300 comprises a strap that is extensible, e.g. resiliently extensible. For example the strap may be configured in use to be in tension, and to direct a force to draw a seal-forming structure 3100 into sealing contact with a portion of a patient's face. In an example the strap may be configured as a tie.

The strap of the positioning and stabilising structure 3300 may be at least partially constructed from an adaptive material (e.g., a moisture activated material, a heat activated material, an auxetic material, and/or a combination of different materials) as described in PCT/SG2020/050792, which is incorporated herein by reference in its entirety. The strap may expand to provide additional comfort to patients under various usage conditions.

In one form of the present technology, the positioning and stabilising structure comprises a first tie, the first tie being constructed and arranged so that in use at least a portion of an inferior edge thereof passes superior to an otobasion superior of the patient's head and overlays a portion of a parietal bone without overlaying the occipital bone.

In one form of the present technology suitable for a nasal-only mask or for a full-face mask, the positioning and stabilising structure includes a second tie, the second tie being constructed and arranged so that in use at least a portion of a superior edge thereof passes inferior to an otobasion inferior of the patient's head and overlays or lies inferior to the occipital bone of the patient's head.

In one form of the present technology suitable for a nasal-only mask or for a full-face mask, the positioning and stabilising structure includes a third tie that is constructed and arranged to interconnect the first tie and the second tie to reduce a tendency of the first tie and the second tie to move apart from one another.

In certain forms of the present technology, a positioning and stabilising structure 3300 comprises a strap that is bendable and e.g. non-rigid. An advantage of this aspect is that the strap is more comfortable for a patient to lie upon while the patient is sleeping.

In certain forms of the present technology, a positioning and stabilising structure 3300 comprises a strap constructed to be breathable to allow moisture vapour to be transmitted through the strap, In certain forms of the present technology, a system is provided comprising more than one positioning and stabilising structure 3300, each being configured to provide a retaining force to correspond to a different size and/or shape range. For example, the system may comprise one form of a positioning and stabilising structure 3300 suitable for a large sized head, but not a small sized head, and another suitable for a small sized head, but not a large sized head.

As shown in FIGS. 6A-6Q, the positioning and stabilising structure 3300 may include a headgear assembly 3302 that includes a sleeve 3304 and a pair of arms 3306 (e.g., a left arm and a right arm). Each of the arms 3306 may be a rigidized arm 3306. Together, the sleeve 3304 and the arms 3306 are coupled to the seal-forming structure 3100 and the plenum chamber 3200 in order to retain them against the patient's face in a therapeutically effective position (e.g., where substantially no pressurized air leaks between the patient's face and the seal-forming structure 3100).

In the illustrated form, the sleeve 3304 is constructed from a flexible material. This permits the sleeve 3304 to bend and flex, and conform to different contours of a patient's head.

In certain forms, the sleeve 3304 may be constructed from an elastic material or have elastic properties. In other words, the sleeve 3304 may be capable of stretching when a tensile force is applied, and returning to its original position when the tensile force is released. The sleeve 3304 may be constructed from a textile that includes one or more elastomeric properties, or an elastomeric material may be included in the sleeve 3304 with the textile. For example, the sleeve 3304 may be at least partially constructed from elastane, a thermoplastic elastomer (TPE), silicone, or a similar material. The sleeve 3304 may be woven, knitted, braided, molded, extruded, or otherwise formed. The sleeve 3304 may include a generally flat, rectangular shape, and may be formed with a cavity 3308 that extends through the sleeve 3304, and is capable of receiving another object.

The textile may provide comfort to the user while the sleeve 3304 rests against their face (e.g., it is non-abrasive). The elastomeric material may allow the sleeve 3304 to stretch in order to better fit around the patient's head (e.g., not be too tight). A portion of the sleeve 3304 may also be bifurcated so that a portion of the sleeve 3304 includes two separate sections. For example, the sleeve 3304 may include a first rear section 3310a and a second rear section 3310b. When the sleeve 3304 is worn by the patient, the first and second rear sections 3310a, 3310b contact a posterior portion of the patient's head. The first rear section 3310a may be partially spaced from the second rear section 3310b, and may help to distribute a force from the sleeve 3304 on the patient's head.

In certain forms, the sleeve 3304 may be formed as multiple pieces (e.g., a first portion 3304a and a second portion 3304b), and coupled together by a fastener 3312 (e.g., a buckle). The fastener 3312 changes a usable length of the sleeve 3304 (e.g., a length of the sleeve 3304 that is exposed to the patient's head) in order to adjust the fit relative to the patient's head. The usable length of the sleeve 3304 plus a length of the seal-forming structure 3100 is approximately equal to a circumference of the patient's head. The patient may increase or decrease the usable length (e.g., by moving the portion(s) 3304a, 3304b relative to one another through the fastener 3312) so that the sleeve 3304 is snug, but not tight against their head. In other forms, the sleeve 3304 may be formed as a single body, and the patient may be unable to adjust the usable length of the sleeve 3304.

Instead, the patient may select between different sized sleeves 3304 (e.g., sleeves 3304 with different pre-selected usable lengths).

The sleeve 3304 may be at least partially rigidized (e.g., using rigidized thread, or other rigid or semi-rigid material). The rigid or semi-rigid material in the sleeve 3304 may control where the sleeve 3304 is able to stretch (e.g., disposed on at least one side of the elastic or elastomeric material to allow stretching in a single direction). This may prevent the sleeve 3304 from stretching too far and breaking (e.g., because the elastic or elastomeric material fails). The rigid or semi-rigid material may also control the flexion of the sleeve 3304, and assist in maintaining a shape of the sleeve 3304. For example, the rigid or semi-rigid material may assist in maintaining the generally rectangular shape of the sleeve 3304. The rigid or semi-rigid material may also provide stiffness to the sleeve 3304, and provide resistance to bending.

In other forms, the sleeve 3304 may be at least partially rigidized with a stiffening portion that may be mouldable or capable of being formed into a shape so as to provide a better fit with the patient's face for improved comfort. For example, the material of the stiffening portions may include thermoplastic or thermosoftening plastic which have activation agent dependent material properties e.g. its material properties such as stiffness is altered when its temperature is within a predetermined range. In other forms, the stiffening portions have an altered stiffness upon application of a treatment. Stiffening portions may alter its material properties, for example stiffness, upon other activation agents (other than temperature). An activation agent may include, but is not limited to, an electrical current, a chemical, a pressure, and/or a force. An example of a stiffening portion is described in PCT/SG2020/050792, which is incorporated herein by reference in its entirety.

As shown in FIG. 6C, each end of the sleeve 3304 includes an opening 3315 to the cavity 3308. Where the sleeve 3304 includes two separate portions 3304a, 3304b, the sleeve 3304 also includes two distinct cavities 3308 with two distinct openings 3315 (e.g., the cavity 3308 in the first portion 3304a does not connect with the cavity 3308 in the second portion 3304b). Conversely, the sleeve 3304 may include a single cavity 3308 if it is formed as a single body.

The opening 3315 to the cavity 3308 includes a generally round (e.g., circular, elliptical, etc.) shape, as opposed to the generally rectangular shape of the remainder of the sleeve 3304. The opening 3315 to the cavity 3308 may also be wider than the remainder of the cavity 3308 (e.g., an inner diameter of the opening is wider than the remainder of the sleeve). This may assist the cavity 3308 in receiving objects, because the wide opening 3315 allows objects to be more easily inserted. In the illustrated example, the opening 3315 is rigidly maintained with the round shape so that the cavity is always accessible (e.g., the sleeve 3304 does not collapse on itself, thereby closing off the cavity 3308).

As shown in FIG. 6C, a rigidized arm 3306 extends from either side of the seal-forming structure 3100. In the illustrated example, both rigidized arms 3306 are substantially identical to each other (e.g., have the same length), and the following features will be described with respect to a single rigidized arm 3306, although they are included on both.

As shown in FIGS. 6E and 6F, the rigidized arm 3306 includes a plug 3316 situated at one end. The plug 3316 is formed from a rigid or semi-rigid material, and is positioned adjacent to the seal-forming structure 3100. In some forms, the plug 3316 and the seal-forming structure 3100 may be formed as a unitary piece. In other forms, the plug 3316 may be coupled to the seal-forming structure 3100 (e.g., using one or more of a fastener, an adhesive, a magnet, a press-fit, a snap-fit, etc.).

In certain forms, the plenum chamber 3200 includes an orifice 3202 on a lateral surface (see e.g., FIG. 6S). The orifice 3202 may extend toward a center of the plenum chamber 3200, so that the orifice 3202 may provide fluid communication into and/or out of the plenum chamber 3200. The plug 3316 is inserted into the orifice 3202, and limits the ingress and egress of fluid (e.g., pressurized gas) through the orifice 3202. The plug 3316 may be secured using a press-fit, such that the frictional engagement between the orifice 3202 and the plug 3316 limits any fluid from entering or exiting the orifice 3202. An adhesive (e.g., glue) may be used in addition to a press-fit in order retain the plug 3316 within the orifice 3202. The plug 3316 may be permanently secured in the orifice 3202 (e.g., during assembly of the patient interface 3000) so that the fluid is limited from flowing through the orifice 3202 after assembly is complete.

A clipping body 3320 is coupled to the plug 3316, and is positioned outside of the orifice 3202 while the plug 3316 is received within the orifice 3202. The clipping body 3320 is formed from a rigid material (e.g., hard plastic), and is configured to retain its shape. In the illustrated example, the clipping body 3320 forms at least a partially round shape (e.g., circular, elliptical, etc.). The shape of the clipping body 3320 may form substantially the same shape as the opening to the cavity 3308. This may allow the clipping body 3320 to be received within the cavity 3308.

In one form, the clipping body 3320 includes a first clipping body portion 3320a and a second clipping body portion 3320b. The clipping body portions 3320a, 3320b may mirror each other, and may each define a portion of the partially round shape. At least one discontinuity (e.g., a gap) exists between the clipping body portions 3320a, 3320b, so that the clipping bodies do not form the entire partially round shape. In the illustrated example, a pair of discontinuities exist between the clipping body portions 3320a, 3320b, so that each respective clipping body portion 3320a, 3320b is independent from the other. In other examples, the clipping body 3320 may include a greater or fewer number of clipping body portions, dependent on the number of discontinuities.

In one form, the clipping body 3320 includes apertures 3324 positioned through a surface of the clipping body 3320. The apertures 3324 may be rectangular in shape, or may have any other suitable shape (e.g., round, triangular, pentagonal, etc.). In the illustrated form, each clipping body portion 3320a, 3320b includes an aperture 3324. The apertures 3324 are positioned approximately 180° apart (e.g., a straight line passes through a center of both apertures 3324; see FIGS. 6E and 6S). In other words, the apertures 3324 of the clipping body 3320 are on opposite sides of the clipping body 3320.

In one form, the clipping body 3320 is rigidly coupled to the plug 3316, and is not rotatable relative to the plug 3316. The orientation of the apertures 3324 with respect to one another, and to the plug 3316, remains constant. The clipping body 3320 may be capable of flexing (i.e., bending) relative to the plug 3316. The clipping body 3320 may be limited in the amount it is capable of flexing so that it does not break (e.g., snap off).

Each rigidized arm 3306 may comprise an arm portion 3328. An arm portion 3328 includes a fixed end 3329 coupled to the plug 3316, and a free end 3330 distal to the plug 3316. The fixed end 3329 may be permanently coupled to the plug 3316, so that the arm portion 3328 and the plug 3316 cannot be separated. The arm portion 3328 extends between the clipping body portions 3320a, 3320b so that the clipping body portions 3320a, 3320b curve around the arm portion 3328. The arm portion 3328 also has a relatively flat and elongated configuration, so that the arm portion 3328 is spaced apart from the clipping body portions 3320a, 3320b. The arm portion 3328 also includes rounded edges (e.g., proximate to the free end 3330), and includes substantially no sharp edges or corners. The arm portion 3328 also includes a substantially smooth surface.

As shown in FIGS. 6E and 6F, the arm portion 3328 may be constructed from a semi-rigid material, which may be capable of some movement. In other words, a patient may be capable of bending the arm portion 3328 into a preferred position, and the arm portion 3328 is capable of maintaining the position after the patient removes the bending force. Specifically, the patient may be able to impart a curvature onto the arm portion 3328 (e.g., concave to the patient's head, convex to the patient's head, or both). The patient may be able to repeatedly adjust the arm portion 3328 until a position preferred by the patient is achieved.

As shown in FIG. 6E, the arm portion 3328 is substantially straight (e.g., parallel to the sagittal plane of a patient), and includes little to no curvature relative to the patient. A patient may grasp and bend the arm portion 3328. In the illustrated example, the patient grasps the arm portion 3328 proximate the free end 3330, although the patient may grasp the arm portion 3328 anywhere. A larger length of the arm portion 3328 may be curved (i.e., concave and/or convex) if a single bend is made proximate the center of the arm portion 3328, and proximate either of the ends 3329, 3330. The patient may grasp the arm portion 3328 at multiple positions and create multiple bends along the length of the arm portion 3328. Each bend may have the same or different radius of curvature relative to any other bend along the length of the arm portion 3328.

As shown in FIG. 6F, the free end 3330 of the arm portion 3328 is bent into a concave orientation with respect to the seal-forming structure 3100. In this example, the remained of the arm portion 3328 remains relatively straight (e.g., neither concave nor convex). The patient may further bend the arm portion 3328 along the remaining length, or may leave sections of the arm portion 3328 straight. Once the patient finishes bending the arm portion 3328, the curvature of the arm portion 3328 is maintained until the patient attempts to re-bend the arm portion 3328. In other words, the rigid or semi-rigid material of the arm portion 3328 maintains the applied curvature, and does not return the arm portion 3328 to a neutral (e.g., straight) position when the bending force is removed.

As shown in FIGS. 6F and 6G, once the curvature of the arm portion 3328 is set (e.g., in a patient desired position), the sleeve 3304 may be slid along the length of the arm portion 3328 in order to at least partially cover the arm portion 3328. The flexible material of the sleeve 3304 allows the sleeve 3304 to conform to any curvature that the arm portion 3328 has. For example, the sleeve 3304 is bendable in all directions so that the sleeve 3304 may substantially match the shape of the arm portion 3328. The rigid or semi-rigid structure of the arm portion 3328 keeps the sleeve 3304 in that shape. In other examples, the arm portion 3328 may be bent after the sleeve 3304 has been at least partially slid along.

As shown in FIG. 6G, the arm portion 3328 may be inserted into the cavity 3308 of the sleeve 3304. Said another way, the sleeve 3304 may be slipped over the arm portion 3328 via the cavity 3308. The free end 3330 of the arm portion 3328 is first inserted into the sleeve 3304 via the cavity 3308. The arm portion 3328 is pushed further inside of the sleeve 3304 (i.e., further into the cavity 3308) until substantially all of the arm portion 3328 is within the sleeve 3304. The rounded edges and sides of the arm portions 3328 helps to limit or prevent snagging or tearing of the sleeve 3304 as the arm portion 3328 is being inserted. Said another way, the arm portion 3328 does not include sharp edges that could dig into and potentially tear a hole in the sleeve 3304. The smooth surface of the arm portions 3328 also assists in limiting snagging or tearing of the sleeve 3304 while the arm portion 3328 is being inserted (i.e., because rough surfaces are limited from catching on the sleeve 3304).

In other forms, the rigidized arm 3306 may include a substantially small or no arm portion 3328. The sleeve 3304 may still connect to the clipping body 3320 as described. In some forms, the sleeve 3304 may include greater stiffness to compensate for the reduced length of the arm portion 3328.

As shown in FIG. 6G, the sleeve 3304 may be moved (or translated) in a direction towards the plug 3316. Consequently, the sleeve 3304 is slipped over the arm portion 3328 to a greater extent. As shown in FIG. 6H, the arm portion 3328 is fully inserted into the cavity 3308 of the sleeve 3304. Said another way, the opening 3315 of the cavity 3308 is positioned proximate to the fixed end 3329 of the arm portion 3328. The cavity 3308 may extend beyond the length of the arm portion 3328 (e.g., a length of the cavity 3308 may be longer than a length of the arm portion 3328), but the arm portion cannot extend any further into the cavity 3308, because the plug 3316 limits further translation of the sleeve 3304. The plug 3316 is wider than the opening 3315, and prevents further ingress of the arm portion 3328 into the cavity 3308. The sleeve 3304 receives the clipping body portions 3320a, 3320b within the cavity 3308, and engages the clipping body portions 3320a, 3320b in order to mechanically couple the sleeve 3304 to the rigidized arm 3306. The engagement between the sleeve 3304 and the rigidized arm 3306 facilitates easy removal of the sleeve 3304 from the arm portion 3328 because the mechanical connection can be easy broken (see e.g., FIG. 6I). The sleeve 3304 is removed in the reverse of how it was positioned on the arm portion 3328. As shown in FIG. 6I, the sleeve 3304 may be moved in a direction away from the plug 3316. Consequently, the sleeve 3304 is slipped over the arm portion 3328 to a lesser extent.

As shown in FIG. 6J, the first portion 3304a and the second portion 3304b of the sleeve 3304 may be slipped over the arm portions 3328 at substantially the same time, while the plenum chamber 3200 and seal-forming structure 3100 are positioned against the patient's oro-nasal region (e.g., the patient's nose and/or mouth). Each portion 3304a, 3304b may be slipped over the respective arm portions 3328 as described above, so that openings 3315 of the common cavity 3308 (or individual cavities 3308) are positioned proximate to the respective plugs 3316. As the portions 3304a, 3304b are slipped on, the positioning and stabilising structure 3300 becomes tighter against the patient's head. In other words, the portions 3304a, 3304b are pulled toward an anterior of the patient's head so that the sleeve 3304 is against a posterior of a patient's head (e.g., the sleeve 3304 is taut).

As shown in FIG. 6K, after the sleeve portions 3304a, 3304b have been connected to the respective plug 3316, the patient may adjust the usable length of the sleeve 3304. The patient may use the fastener 3312 in order to increase or decrease the usable length of the sleeve 3304, so that the sleeve 3304 is comfortable against the patient's head. Said another way, the patient can adjust the usable length so that the seal-forming structure 3100 is snug against the patient's face but is not too tight (e.g., not digging into the patient's face, not creating red marks on their skin, etc.). Before adjusting the length of the sleeve 3304, the patient may position the sleeve 3304 along the posterior of their head. For example, the patient may move the sleeve 3304 in the superior or inferior direction in order to provide an appropriate force to the seal-forming structure 3100, and/or to maximize comfort for the patient. If the sleeve 3304 is bifurcated, the patient may also change the position of each bifurcated section relative to the other in order to adjust force and/or comfort. The patient may also adjust the usable length prior to donning the positioning and stabilising structure 3300 (e.g., because the usable length was too small to don).

The patient may hold the seal-forming structure 3100 and/or the plenum chamber 3200 in place adjacent their oro-nasal region while adjusting the usable length of the sleeve 3304. This helps to ensure a proper seal between the seal-forming structure 3100 and the patient's skin (e.g., in the proper location, substantially no leaks, etc.). By holding the seal-forming structure 3100 in a desired location, the sleeve 3304 can be tightened to the appropriate usable length. For example, the usable length will be different depending on where the patient positions the sleeve 3304. Positioning the sleeve 3304 more superior on the patient's head equates to a longer usable length to achieve the same sealing force (e.g., because the position of the seal-forming structure 3100 is always positioned proximate the patient's nose and/or mouth).

As shown in FIGS. 6L-6Q, the sleeve 3304 is assembled by positioning a first (or inner) coupling 3334 and a second (or outer) coupling 3338 within both ends of the cavity 3308 (or cavities 3308). The couplings 3334, 3338 are positioned proximate an end of the sleeve 3304, and may form the opening 3315 in the sleeve 3304. In other words, the outer coupling 3338 includes a generally circular shape. The inner coupling 3334 may also include the same generally circular shape.

As shown in FIG. 6L, when the sleeve 3304 is initially assembled, neither coupling 3334, 3338 is present within the cavity 3308. The sleeve 3304 is generally flat, and the opening 3315 and the cavity 3308 are generally closed off. Said another way, sides of the sleeve 3304 are proximate to one another so that an internal volume within the cavity 3308 is low. The sleeve 3304 may have a generally rectangular shape, but is flexible and may be capable of changing shapes (e.g., to a circular cross-section). The outer coupling 3338 is selected and moved to a position proximate to the sleeve 3304. The outer coupling 3338 has a generally circular cross-section with a hollow center. In the illustrated example, the outer coupling 3338 also has a larger diameter than the sleeve 3304.

As shown in Fig. M, the outer coupling 3338 is positioned within the cavity 3308 of the sleeve 3304. The flexible material of the sleeve 3304 is capable of expanding in order to receive the outer coupling 3338. In other words, the outer coupling 3338 stretches the sleeve 3304 as it is inserted into the cavity 3308, so that the end on the sleeve 3304 is wider than a center of the sleeve 3304. The opening 3315 of the cavity 3308 may have a different shape than the rest of the cavity 3308. The outer coupling 3338 retains the sleeve 3304 in the wider, generally circular position, while the rest of the sleeve 3304 (and therefore, the rest of the cavity 3308) remains in the generally flat, rectangular orientation. The outer coupling 3338 may be made from a rigid or semi-rigid material (e.g., a hard plastic) so that it retains its shape under pressure. Said another way, a biasing or elastic force that attempts to return the sleeve 3304 to its original position is unable to change the shape of the outer coupling 3338.

As shown in FIG. 6M, the outer coupling 3338 is slid into the cavity 3308, and spaced apart from the initial opening 3315 of the sleeve 3304. In other words, an edge (e.g., a free end 3342) of the sleeve 3304 is not aligned with an edge of the outer coupling 3338. A portion of the sleeve 3304 extends beyond the outer coupling 3338 on either side (e.g., left and right as viewed in FIG. 6M). The outer coupling 3338 may be fastened to the sleeve 3304 at an appropriate location within the cavity 3308. For example, the outer coupling 3338 may be fixed by using an adhesive (e.g., glue), using a mechanical fastener, using a magnetic fastener, sewing, or by any similar means. Once the outer coupling 3338 is positioned at the desired location, the free end 3342 of the sleeve 3304 is folded inwardly on itself. In other words, the free end 3342 of the sleeve 3304 is folded so that it is positioned within the cavity 3308. The free end 3342 is folded so that it rests on the surface of the outer coupling 3338. The outer coupling 3338 is therefore at least partially sandwiched between folds of the sleeve 3304. The further away from the free end 3342 that the outer coupling 3338 is disposed, the greater the length of the sleeve 3304 that may be folded over the outer coupling 3338. This length may only partially cover the outer coupling 3338, or it may completely cover the outer coupling 3338 so that it is completely enclosed by the sleeve 3304. Once the free end 3342 is folded, the outer end of the outer coupling 3338 (e.g., the left end as viewed in FIG. 6N) is substantially aligned with the opening 3315 of the cavity 3308. Thus, the shape of the outer coupling 3338 forms the shape of the opening 3315 to the cavity 3308 once the free end 3342 is folded over.

Once the free end 3342 of the sleeve 3304 is folded over the outer coupling 3338, the free end 3342 may be secured to the outer coupling 3338 and/or to the sleeve 3304. For example, the outer coupling 3338 may be fixed by using an adhesive (e.g., glue), using a mechanical fastener, using a magnetic fastener, sewing, or by any similar means. The free end 3342 is fixed so that it does not unfold and move away from the outer coupling 3338. In some forms, the same means is used to couple both the outer coupling 3338 within the cavity 3308, and the free end 3342 to the outer coupling 3338 and/or to the sleeve 3304 (e.g., only a single means is used). In some forms, the outer coupling 3338 may not be directly coupled to the sleeve 3304. Instead, the free end 3342 may be folded completely over the outer coupling 3338, and coupled to the sleeve 3304, thereby forming a pocket around the outer coupling 3338. The outer coupling 3338 may be movable (e.g., if it was not secured to the sleeve 3304 itself), but only within the confines of the pocket.

As shown in FIG. 6O, the inner coupling 3334 is selected and moved to a position proximate to the sleeve 3304. The inner coupling 3334 has a generally circular cross-section with a hollow center. The outer diameter of the inner coupling 3334 is less than the inner diameter of the outer coupling 3338. The inner coupling 3334 is positioned at the opening 3315 of the cavity 3308 (i.e., the edge of the outer coupling 3338), and is narrower than the opening 3315 so that it may slide into the opening 3315.

The inner coupling 3334 includes at least one projection 3346 that extends toward a center of the inner coupling 3334. In the illustrated example, the inner coupling 3334 includes a pair of projections 3346. The projections 3346 may extend away from the surface of the inner coupling 3334 at an angle θ (see e.g., FIG. 6Q). The angle θ may be an angle measured from an axis 3348 that is parallel to a radial axis of the inner coupling 3334. In some forms, the angle θ is between 10° and 90°. In some forms, the angle θ is between 20° and 80°. In some forms, the angle θ is between 30° and 70°. In some forms, the angle θ is between 35° and 65°. In some forms, the angle θ is between 40° and 60°. In some forms, the angle θ is approximately 55°. In some forms, both projections 3346 extend at the same angle (e.g., are mirrors of one another).

The projection 3346 may extend to a point or may be rounded. The projections 3346 are spaced apart from one another so that they are not in contact with the other projections 3346. The projections 3346 also do not extend out of the inner coupling 3334. Said another way, the projections 3346 are maintained entirely within the volume of the inner coupling 3334.

As shown in FIG. 6P, the inner coupling 3334 is slid into the cavity 3308. The inner coupling 3334 rests on the free end 3342 of the sleeve 3304 within the cavity 3308. As seen in cross-section, the sleeve 3304 includes different layers of materials within the cavity 3308. For example, starting from the outside, the sleeve 3304 forms the outermost surface of the positioning and stabilising structure 3300, the outer coupling 3338 is positioned directly inside of the sleeve 3304, the free end 3342 of the sleeve 3304 is folded over the outer coupling 3338, and the inner coupling 3334 is positioned directly inside of the free end 3342. Thus, there are four layers, where no adjacent (or adjoining) layers are the same (e.g., the positioning and stabilising structure 3300 alternates between flexible and rigid/semi-rigid).

The inner coupling 3334 may be secured within the cavity once the inner coupling 3334 is positioned within in the desired location. For example, the inner coupling 3334 may be fixed by using an adhesive (e.g., glue), using a mechanical fastener, using a magnetic fastener, sewing, or by any similar means. This location may be substantially aligned with the outer coupling 3338. For example, the inner and outer couplings 3334, 3338 may be concentric, and the edges of the inner and outer couplings 3334, 3338 may be aligned. In other words, the inner and outer couplings 3334, 3338 may both be positioned at the opening 3315. The space between the projections 3346 leaves a space through the opening 3315 and into the cavity 3308.

Returning to FIGS. 6G-6I, the arm portion 3328 is narrower than the width between the projections 3346. The projections 3346 do not create resistance as the sleeve 3304 slides along the arm portion 3328. Said another way, although the projections 3346 may touch the arm portion 3328, the projections 3346 do not make sliding the sleeve 3304 along the arm portion 3328 more difficult. The wider opening created by the outer coupling 3338 provides a large target area for a patient to insert the arm portion 3328. The shape of the sleeve 3304 (e.g., generally rectangular) does not generally change when the arm portion 3328 is inserted.

As shown in FIG. 6H, the opening 3315 of the sleeve 3304 is slid up to the plug 3316. The clipping body portions 3320a, 3320b are received within the inner coupling 3334 when the arm portion 3328 is fully received within the cavity 3308. The patient aligns the projections 3346 of the inner coupling 3334 with the clipping body portions 3320a, 3320b, so that the projections 3346 can be received within the clipping body portions 3320a, 3320b. The angle θ of the projection 3346 helps to maintain the engagement between the respective projection 3346 and the clipping body 3320. Once the projections 3346 enter the respective clipping body portions 3320a, 3320b, the sleeve 3304 is retained relative to the plug 3316 (e.g., is not movable away from the plug 3316).

With the sleeve 3304 secured in place, the positioning and stabilising structure 3300 is secured to the patient's head. As shown in FIGS. 6J and 6K, the arm portions 3328 extend away from the oro-nasal region, and along the patient's cheek, toward a posterior of the patient's head. The arm portions 3328 also extend in a superior direction along the patient's head (see e.g., FIG. 6K). In some forms, the arm portions 3328 may not extend beyond the patient's respective ear. In other words, the free end 3330 of the arm portion 3328 does not extend more posterior than the patient's ear. The arm portions 3328 extend so that they do not contact the patient's ear. For example, the arm portions 3328 extend along a line that projects superior to the patient's ear, so that the arm portion 3328 does not intersect the ear (e.g., and cause discomfort for the patient). The sleeve 3304 extends from the oro-nasal region, to the posterior of the patient's head, and back to the oro-nasal region. The sleeve 3304 follows the same line as the arm portion 3328, so that the sleeve 3304 also does not intersect the patient's ear.

In other forms (not shown), the free end 3330 of each arm portion 3328 may extend to a point more anterior than the respective ear, and may contact the patient's face at a location inferior to the otobasion superior and superior to the otobasion inferior. The sleeve 3304 may bifurcate in order to extend around and minimize contact with the patient's ear.

Returning to FIG. 6I, the patient may disengage the projections 3346 from the clipping body portions 3320a, 3320b in order to slide the sleeve 3304 off of the arm portion 3328. In some forms, the patient may apply a suitable force directed away from the plug 3316 in order to remove the sleeve 3304. The applied force may cause the projections to exit the respective clipping body portions 3320a, 3320b, so that the sleeve 3304 is once again freely movable relative to the plug 3316. In other forms, a force alone may be insufficient to remove the projections 3346 from the clipping body portions 3320a, 3320b, without breaking the projections 3346 (and thereby preventing future connections). Instead the patient may have to apply a compressive force to the couplings 3334, 3338 prior to applying a force to the sleeve 3304 away from the plug. Said another way, the patient squeezes the outer coupling 3338 in order to compress the inner coupling 3334 and cause the projections 3346 to leave the clipping body portions 3320a, 3320b. At this point, the inner coupling 3334 is no longer mechanically engaged to the plug 3316, and can move relative to the plug 3316. The rigid or semi-rigid material of the couplings 3334, 3338 may allow for small amounts of flexion in order to allow the projections 3346 to move into and out of the clipping body portions 3320a, 3320b.

As shown in FIG. 6R, the air circuit 4170 may be removed from the plenum chamber 3200 in order to expose a connection port 3600. Similarly, the plugs 3316 may be removed from the plenum chamber 3200. A plug 3316, clipping body 3320, and arm portion 3328 are formed as a single piece (e.g., they are connected to one another and not separable), so each are removed from the plenum chamber 3200 together. In its place, the orifice 3202 remains. Like the connection port 3600, the orifice 3202 provides fluid communication into the plenum chamber 3200. While the plugs 3316 are positioned within the orifices 3202, ingress and egress of fluid (e.g., air) is substantially prevented, but air can freely enter and exit when the plugs 3316 are removed. The plugs 3316 may be connected with a press fit, a snap-fit, or a similar connection in order to allow repeated insertion and removal of the plug 3316 (e.g., as shown in FIGS. 6R and 6S), while limiting fluid flow through the respective orifice 3202 when the respective plug 3316 is inserted. This may assist a patient in cleaning the interior of the plenum chamber 3200 (e.g., after use each night).

Alternatively, the plug 3316 may be integrally formed with the plenum chamber 3200 (or more broadly, a facial interface) in a one-piece construction. This may simplify the manufacturing (e.g., via molding) of the patient interface 3000 (or generally a face mounted interface). The plug 3316 may still prevent or limit the ingress or egress of airflow, although an airflow path may not exist because of the integral formation.

As shown in FIGS. 6T-6W, a cover 3354 may be positioned over the connection port 3600 in order to substantially prevent fluid from entering and exiting the plenum chamber 3200. The cover 3354 connects to the plenum chamber 3200 in the connection port 3600 with a friction fit, a press fit, a snap-fit, a magnetic engagement, or a similar connection so that it can be removed, but also limits fluid flow through the connection port 3600 when it is connected. A fluid conduit 3358 (e.g., conduit headgear) can connect to the seal-forming structure 3100 at the orifice 3202. The fluid conduit 3358 is a hollow tube and includes an inlet 3362 in a center of the hollow tube. When worn by a patient, the fluid conduit 3358 may extend along a similar path as the arm portions 3328 (e.g., along the cheek) toward the superior portion of the patient's head. The air circuit 4170 can connect to the fluid conduit 3358 at the inlet 3362 (i.e., on a superior region of the patient's head), and provide pressurized air through the fluid conduit 3358 to the plenum chamber 3200. In other words, air flows from the inlet 3362, through the hollow tube of the fluid conduit 3358, and to the plenum chamber 3200. In this form (i.e., with the fluid conduit 3358 connected), the fluid conduit 3358 may function as the positioning and stabilising structure 3300, and may provide some assistance in retaining the seal-forming structure 3100 against the patient's face in a therapeutically effective position. Additionally, a rear strap 3366 may be coupled to tabs 3370 of the fluid conduit 3358. The rear strap 3366 may extend around a posterior of the patient's head (e.g., across the patient's head proximate the occipital bone). The patient may then use the patient interface 3000 modularly, and select how the pressurized air is delivered to their airways. A primary factor in determining this may be comfort for the patient (e.g., where the air circuit 4170 extends from the patient interface).

The fluid conduit 3358 may convey pressurized air toward the seal-forming structure 3100. The fluid conduit 3358 is made from and/or lined with an impermeable material (e.g., silicon, a thermoformed and/or laminate structure, etc.). The fluid conduit 3358 couples to the plenum chamber 3200 with a seamless or substantially seamless transition (e.g., within the orifice 3202) in order to prevent or substantially prevent the escape of pressurized air toward the ambient. In one example, the fluid conduit 3358 is dual lumen tubes.

5.3.4 Vent

In one form, the patient interface 3000 includes a vent 3400 constructed and arranged to allow for the washout of exhaled gases, e.g. carbon dioxide.

In certain forms the vent 3400 is configured to allow a continuous vent flow from an interior of the plenum chamber 3200 to ambient whilst the pressure within the plenum chamber is positive with respect to ambient. The vent 3400 is configured such that the vent flow rate has a magnitude sufficient to reduce rebreathing of exhaled $CO_2$ by the patient while maintaining the therapeutic pressure in the plenum chamber in use.

One form of vent 3400 in accordance with the present technology comprises a plurality of holes, for example, about 20 to about 80 holes, or about 40 to about 60 holes, or about 45 to about 55 holes.

The vent 3400 may be located in the plenum chamber 3200. Alternatively, the vent 3400 is located in a decoupling structure, e.g., a swivel.

5.3.5 Decoupling Structure(s)

In one form the patient interface 3000 includes at least one decoupling structure, for example, a swivel or a ball and socket.

5.3.6 Connection Port

Connection port 3600 allows for connection to the air circuit 4170.

5.3.7 Forehead Support

In one form, the patient interface 3000 includes a forehead support 3700.

5.3.8 Anti-Asphyxia Valve

In one form, the patient interface 3000 includes an anti-asphyxia valve.

5.3.9 Ports

In one form of the present technology, a patient interface 3000 includes one or more ports that allow access to the volume within the plenum chamber 3200. In one form this allows a clinician to supply supplementary oxygen. In one form, this allows for the direct measurement of a property of gases within the plenum chamber 3200, such as the pressure.

5.4 RPT Device

An RPT device 4000 in accordance with one aspect of the present technology comprises mechanical, pneumatic, and/or electrical components and is configured to execute one or more algorithms 4300, such as any of the methods, in whole or in part, described herein. The RPT device 4000 may be configured to generate a flow of air for delivery to a patient's airways, such as to treat one or more of the respiratory conditions described elsewhere in the present document.

In one form, the RPT device 4000 is constructed and arranged to be capable of delivering a flow of air in a range of −20 L/min to +150 L/min while maintaining a positive pressure of at least 6 cmH$_2$O, or at least 10cmH$_2$O, or at least 20 cmH$_2$O.

The RPT device may have an external housing 4010, formed in two parts, an upper portion 4012 and a lower portion 4014. Furthermore, the external housing 4010 may include one or more panel(s) 4015. The RPT device 4000 comprises a chassis 4016 that supports one or more internal components of the RPT device 4000. The RPT device 4000 may include a handle 4018.

The pneumatic path of the RPT device 4000 may comprise one or more air path items, e.g., an inlet air filter 4112, an inlet muffler 4122, a pressure generator 4140 capable of supplying air at positive pressure (e.g., a blower 4142), an outlet muffler 4124 and one or more transducers 4270, such as pressure sensors and flow rate sensors.

One or more of the air path items may be located within a removable unitary structure which will be referred to as a pneumatic block 4020. The pneumatic block 4020 may be located within the external housing 4010. In one form a pneumatic block 4020 is supported by, or formed as part of the chassis 4016.

The RPT device 4000 may have an electrical power supply 4210, one or more input devices 4220, a pressure generator 4140, and transducers 4270. Electrical components 4200 may be mounted on a single Printed Circuit Board Assembly (PCBA) 4202. In an alternative form, the RPT device 4000 may include more than one PCBA 4202.

5.4.1 RPT Device Mechanical & Pneumatic Components

An RPT device may comprise one or more of the following components in an integral unit. In an alternative form, one or more of the following components may be located as respective separate units.

5.4.1.1 Air Filter(s)

An RPT device in accordance with one form of the present technology may include an air filter 4110, or a plurality of air filters 4110.

In one form, an inlet air filter 4112 is located at the beginning of the pneumatic path upstream of a pressure generator 4140.

In one form, an outlet air filter 4114, for example an antibacterial filter, is located between an outlet of the pneumatic block 4020 and a patient interface 3000.

5.4.1.2 Muffler(s)

An RPT device in accordance with one form of the present technology may include a muffler 4120, or a plurality of mufflers 4120.

In one form of the present technology, an inlet muffler 4122 is located in the pneumatic path upstream of a pressure generator 4140.

In one form of the present technology, an outlet muffler 4124 is located in the pneumatic path between the pressure generator 4140 and a patient interface 3000.

5.4.1.3 Pressure Generator

In one form of the present technology, a pressure generator 4140 for producing a flow, or a supply, of air at positive pressure is a controllable blower 4142. For example the blower 4142 may include a brushless DC motor 4144 with one or more impellers. The impellers may be located in a volute. The blower may be capable of delivering a supply of air, for example at a rate of up to about 120 litres/minute, at a positive pressure in a range from about 4 cmH$_2$O to about 20 cmH$_2$O, or in other forms up to about 30 cmH$_2$O when delivering respiratory pressure therapy. The blower may be as described in any one of the following patents or patent applications the contents of which are incorporated herein by reference in their entirety: U.S. Pat. Nos. 7,866,944; 8,638,014; 8,636,479; and PCT Patent Application Publication No. WO 2013/020167.

The pressure generator 4140 may be under the control of the therapy device controller 4240.

In other forms, a pressure generator 4140 may be a piston-driven pump, a pressure regulator connected to a high pressure source (e.g. compressed air reservoir), or a bellows.

5.4.1.4 Transducer(s)

Transducers may be internal of the RPT device, or external of the RPT device. External transducers may be located for example on or form part of the air circuit, e.g., the patient interface. External transducers may be in the form of non-contact sensors such as a Doppler radar movement sensor that transmit or transfer data to the RPT device.

In one form of the present technology, one or more transducers 4270 are located upstream and/or downstream of the pressure generator 4140. The one or more transducers 4270 may be constructed and arranged to generate signals representing properties of the flow of air such as a flow rate, a pressure or a temperature at that point in the pneumatic path.

In one form of the present technology, one or more transducers 4270 may be located proximate to the patient interface 3000.

In one form, a signal from a transducer 4270 may be filtered, such as by low-pass, high-pass or band-pass filtering.

5.4.1.5 Anti-Spill Back Valve

In one form of the present technology, an anti-spill back valve 4160 is located between the humidifier 5000 and the pneumatic block 4020. The anti-spill back valve is constructed and arranged to reduce the risk that water will flow upstream from the humidifier 5000, for example to the motor 4144.

5.4.2 RPT Device Electrical Components

5.4.2.1 Power Supply

A power supply 4210 may be located internal or external of the external housing 4010 of the RPT device 4000.

In one form of the present technology, power supply 4210 provides electrical power to the RPT device 4000 only. In another form of the present technology, power supply 4210 provides electrical power to both RPT device 4000 and humidifier 5000.

5.4.2.2 Input Devices

In one form of the present technology, an RPT device 4000 includes one or more input devices 4220 in the form of buttons, switches or dials to allow a person to interact with the device. The buttons, switches or dials may be physical devices, or software devices accessible via a touch screen. The buttons, switches or dials may, in one form, be physically connected to the external housing 4010, or may, in another form, be in wireless communication with a receiver that is in electrical connection to a central controller.

In one form, the input device 4220 may be constructed and arranged to allow a person to select a value and/or a menu option.

5.5 Air Circuit

An air circuit 4170 in accordance with an aspect of the present technology is a conduit or a tube constructed and arranged to allow, in use, a flow of air to travel between two components such as RPT device 4000 and the patient interface 3000.

In particular, the air circuit 4170 may be in fluid connection with the outlet of the pneumatic block 4020 and the patient interface. The air circuit may be referred to as an air delivery tube. In some cases there may be separate limbs of the circuit for inhalation and exhalation. In other cases a single limb is used.

In some forms, the air circuit 4170 may comprise one or more heating elements configured to heat air in the air circuit, for example to maintain or raise the temperature of the air. The heating element may be in a form of a heated wire circuit, and may comprise one or more transducers, such as temperature sensors. In one form, the heated wire circuit may be helically wound around the axis of the air circuit 4170. The heating element may be in communication with a controller such as a central controller. One example of an air circuit 4170 comprising a heated wire circuit is described in U.S. Pat. No. 8,733,349, which is incorporated herewithin in its entirety by reference.

5.5.1 Supplementary Gas Delivery

In one form of the present technology, supplementary gas, e.g. oxygen, 4180 is delivered to one or more points in the pneumatic path, such as upstream of the pneumatic block 4020, to the air circuit 4170, and/or to the patient interface 3000.

5.6 Humidifier

In one form of the present technology there is provided a humidifier 5000 (e.g. as shown in FIG. 4B) to change the absolute humidity of air or gas for delivery to a patient relative to ambient air. Typically, the humidifier 5000 is used to increase the absolute humidity and increase the temperature of the flow of air (relative to ambient air) before delivery to the patient's airways.

5.7 Breathing Waveforms

FIG. 5 shows a model typical breath waveform of a person while sleeping. The horizontal axis is time, and the vertical axis is respiratory flow rate. While the parameter values may vary, a typical breath may have the following approximate values: tidal volume Vt 0.5 L, inhalation time Ti 1.6 s, peak inspiratory flow rate Qpeak 0.4 L/s, exhalation time Te 2.4 s, peak expiratory flow rate Qpeak −0.5 L/s. The total duration of the breath, Ttot, is about 4 s. The person typically breathes at a rate of about 15 breaths per minute (BPM), with Ventilation Vent about 7.5 L/min. A typical duty cycle, the ratio of Ti to Ttot, is about 40%.

5.8 Glossary

For the purposes of the present technology disclosure, in certain forms of the present technology, one or more of the following definitions may apply. In other forms of the present technology, alternative definitions may apply.

5.8.1 General

Air: In certain forms of the present technology, air may be taken to mean atmospheric air, and in other forms of the present technology air may be taken to mean some other combination of breathable gases, e.g. oxygen enriched air.

Ambient: In certain forms of the present technology, the term ambient will be taken to mean (i) external of the treatment system or patient, and (ii) immediately surrounding the treatment system or patient.

For example, ambient humidity with respect to a humidifier may be the humidity of air immediately surrounding the humidifier, e.g. the humidity in the room where a patient is sleeping. Such ambient humidity may be different to the humidity outside the room where a patient is sleeping.

In another example, ambient pressure may be the pressure immediately surrounding or external to the body.

In certain forms, ambient (e.g., acoustic) noise may be considered to be the background noise level in the room where a patient is located, other than for example, noise generated by an RPT device or emanating from a mask or patient interface. Ambient noise may be generated by sources outside the room.

Automatic Positive Airway Pressure (APAP) therapy: CPAP therapy in which the treatment pressure is automatically adjustable, e.g. from breath to breath, between minimum and maximum limits, depending on the presence or absence of indications of SDB events.

Continuous Positive Airway Pressure (CPAP) therapy: Respiratory pressure therapy in which the treatment pressure is approximately constant through a respiratory cycle of a patient. In some forms, the pressure at the entrance to the airways will be slightly higher during exhalation, and slightly lower during inhalation. In some forms, the pressure will vary between different respiratory cycles of the patient, for example, being increased in response to detection of indications of partial upper airway obstruction, and decreased in the absence of indications of partial upper airway obstruction.

Flow rate: The volume (or mass) of air delivered per unit time. Flow rate may refer to an instantaneous quantity. In some cases, a reference to flow rate will be a reference to a scalar quantity, namely a quantity having magnitude only. In other cases, a reference to flow rate will be a reference to a vector quantity, namely a quantity having both magnitude and direction. Flow rate may be given the symbol Q. 'Flow rate' is sometimes shortened to simply 'flow' or 'airflow'.

In the example of patient respiration, a flow rate may be nominally positive for the inspiratory portion of a breathing cycle of a patient, and hence negative for the expiratory portion of the breathing cycle of a patient. Device flow rate, Qd, is the flow rate of air leaving the RPT device. Total flow rate, Qt, is the flow rate of air and any supplementary gas reaching the patient interface via the air circuit. Vent flow rate, Qv, is the flow rate of air leaving a vent to allow washout of exhaled gases. Leak flow rate, Ql, is the flow rate of leak from a patient interface system or elsewhere. Respiratory flow rate, Qr, is the flow rate of air that is received into the patient's respiratory system.

Flow therapy: Respiratory therapy comprising the delivery of a flow of air to an entrance to the airways at a controlled flow rate referred to as the treatment flow rate that is typically positive throughout the patient's breathing cycle.

Humidifier: The word humidifier will be taken to mean a humidifying apparatus constructed and arranged, or configured with a physical structure to be capable of providing a therapeutically beneficial amount of water ($H_2O$) vapour to a flow of air to ameliorate a medical respiratory condition of a patient.

Leak: The word leak will be taken to be an unintended flow of air. In one example, leak may occur as the result of an incomplete seal between a mask and a patient's face. In another example leak may occur in a swivel elbow to the ambient.

Noise, conducted (acoustic): Conducted noise in the present document refers to noise which is carried to the patient by the pneumatic path, such as the air circuit and the patient interface as well as the air therein. In one form, conducted noise may be quantified by measuring sound pressure levels at the end of an air circuit.

Noise, radiated (acoustic): Radiated noise in the present document refers to noise which is carried to the patient by the ambient air. In one form, radiated noise may be quantified by measuring sound power/pressure levels of the object in question according to ISO 3744.

Noise, vent (acoustic): Vent noise in the present document refers to noise which is generated by the flow of air through any vents such as vent holes of the patient interface.

Oxygen enriched air: Air with a concentration of oxygen greater than that of atmospheric air (21%), for example at least about 50% oxygen, at least about 60% oxygen, at least about 70% oxygen, at least about 80% oxygen, at least about 90% oxygen, at least about 95% oxygen, at least about 98% oxygen, or at least about 99% oxygen. "Oxygen enriched air" is sometimes shortened to "oxygen".

Medical Oxygen: Medical oxygen is defined as oxygen enriched air with an oxygen concentration of 80% or greater.

Patient: A person, whether or not they are suffering from a respiratory condition.

Pressure: Force per unit area. Pressure may be expressed in a range of units, including $cmH_2O$, $g-f/cm^2$ and hectopascal. 1 $cmH_2O$ is equal to 1 $g-f/cm^2$ and is approximately 0.98 hectopascal (1 hectopascal=100 Pa=100 $N/m^2$=1 millibar 0.001 atm). In this specification, unless otherwise stated, pressure is given in units of $cmH_2O$.

The pressure in the patient interface is given the symbol Pm, while the treatment pressure, which represents a target value to be achieved by the interface pressure Pm at the current instant of time, is given the symbol Pt.

Respiratory Pressure Therapy: The application of a supply of air to an entrance to the airways at a treatment pressure that is typically positive with respect to atmosphere.

Ventilator: A mechanical device that provides pressure support to a patient to perform some or all of the work of breathing.

5.8.1.1 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, an exemplary form of LSR has a Shore A (or Type A) indentation hardness in the range of about 35 to about 45 as measured using ASTM D2240

Polycarbonate: a thermoplastic polymer of Bisphenol-A Carbonate.

5.8.1.2 Mechanical Properties

Resilience: Ability of a material to absorb energy when deformed elastically and to release the energy upon unloading.

Resilient: Will release substantially all of the energy when unloaded. Includes e.g. certain silicones, and thermoplastic elastomers.

Hardness: The ability of a material per se to resist deformation (e.g. described by a Young's Modulus, or an indentation hardness scale measured on a standardised sample size).

'Soft' materials may include silicone or thermo-plastic elastomer (TPE), and may, e.g. readily deform under finger pressure.

'Hard' materials may include polycarbonate, polypropylene, steel or aluminium, and may not e.g. readily deform under finger pressure.

Stiffness (or rigidity) of a structure or component: The ability of the structure or component to resist deformation in response to an applied load. The load may be a force or a moment, e.g. compression, tension, bending or torsion. The structure or component may offer different resistances in different directions. The inverse of stiffness is flexibility.

Floppy structure or component. A structure or component that will change shape, e.g. bend, when caused to support its own weight, within a relatively short period of time such as 1 second.

Rigid structure or component: A structure or component that will not substantially change shape when subject to the loads typically encountered in use. An example of such a use may be setting up and maintaining a patient interface in sealing relationship with an entrance to a patient's airways, e.g. at a load of approximately 20 to 30 cmH$_2$O pressure.

As an example, an I-beam may comprise a different bending stiffness (resistance to a bending load) in a first direction in comparison to a second, orthogonal direction. In another example, a structure or component may be floppy in a first direction and rigid in a second direction.

5.8.2 Respiratory Cycle

Apnea: According to some definitions, an apnea is said to have occurred when flow falls below a predetermined threshold for a duration, e.g. 10 seconds. An obstructive apnea will be said to have occurred when, despite patient effort, some obstruction of the airway does not allow air to flow. A central apnea will be said to have occurred when an apnea is detected that is due to a reduction in breathing effort, or the absence of breathing effort, despite the airway being patent. A mixed apnea occurs when a reduction or absence of breathing effort coincides with an obstructed airway.

Breathing rate: The rate of spontaneous respiration of a patient, usually measured in breaths per minute.

Duty cycle: The ratio of inhalation time, Ti to total breath time, Ttot.

Effort (breathing): The work done by a spontaneously breathing person attempting to breathe.

Expiratory portion of a breathing cycle: The period from the start of expiratory flow to the start of inspiratory flow.

Flow limitation: Flow limitation will be taken to be the state of affairs in a patient's respiration where an increase in effort by the patient does not give rise to a corresponding increase in flow. Where flow limitation occurs during an inspiratory portion of the breathing cycle it may be described as inspiratory flow limitation. Where flow limitation occurs during an expiratory portion of the breathing cycle it may be described as expiratory flow limitation.

Types of flow limited inspiratory waveforms:
(i) Flattened: Having a rise followed by a relatively flat portion, followed by a fall.
(ii) M-shaped: Having two local peaks, one at the leading edge, and one at the trailing edge, and a relatively flat portion between the two peaks.
(iii) Chair-shaped: Having a single local peak, the peak being at the leading edge, followed by a relatively flat portion.
(iv) Reverse-chair shaped: Having a relatively flat portion followed by single local peak, the peak being at the trailing edge.

Hypopnea: According to some definitions, a hypopnea is taken to be a reduction in flow, but not a cessation of flow. In one form, a hypopnea may be said to have occurred when there is a reduction in flow below a threshold rate for a duration. A central hypopnea will be said to have occurred when a hypopnea is detected that is due to a reduction in breathing effort. In one form in adults, either of the following may be regarded as being hypopneas:
(i) a 30% reduction in patient breathing for at least 10 seconds plus an associated 4% desaturation; or
(ii) a reduction in patient breathing (but less than 50%) for at least 10 seconds, with an associated desaturation of at least 3% or an arousal.

Hyperpnea: An increase in flow to a level higher than normal.

Inspiratory portion of a breathing cycle: The period from the start of inspiratory flow to the start of expiratory flow will be taken to be the inspiratory portion of a breathing cycle.

Patency (airway): The degree of the airway being open, or the extent to which the airway is open. A patent airway is open. Airway patency may be quantified, for example with a value of one (1) being patent, and a value of zero (0), being closed (obstructed).

Positive End-Expiratory Pressure (PEEP): The pressure above atmosphere in the lungs that exists at the end of expiration.

Peak flow rate (Qpeak): The maximum value of flow rate during the inspiratory portion of the respiratory flow waveform.

Respiratory flow rate, patient airflow rate, respiratory airflow rate (Qr): These terms may be understood to refer to the RPT device's estimate of respiratory flow rate, as opposed to "true respiratory flow rate" or "true respiratory flow rate", which is the actual respiratory flow rate experienced by the patient, usually expressed in litres per minute.

Tidal volume (Vt): The volume of air inhaled or exhaled during normal breathing, when extra effort is not applied. In principle the inspiratory volume Vi (the volume of air inhaled) is equal to the expiratory volume Ve (the volume of air exhaled), and therefore a single tidal volume Vt may be defined as equal to either quantity. In practice the tidal volume Vt is estimated as some combination, e.g. the mean, of the inspiratory volume Vi and the expiratory volume Ve.

(inhalation) Time (Ti): The duration of the inspiratory portion of the respiratory flow rate waveform.

(exhalation) Time (Te): The duration of the expiratory portion of the respiratory flow rate waveform.

(total) Time (Ttot): The total duration between the start of one inspiratory portion of a respiratory flow rate waveform and the start of the following inspiratory portion of the respiratory flow rate waveform.

Typical recent ventilation: The value of ventilation around which recent values of ventilation Vent over some predetermined timescale tend to cluster, that is, a measure of the central tendency of the recent values of ventilation.

Upper airway obstruction (UAO): includes both partial and total upper airway obstruction. This may be associated with a state of flow limitation, in which the flow rate increases only slightly or may even decrease as the pressure difference across the upper airway increases (Starling resistor behaviour).

Ventilation (Vent): A measure of a rate of gas being exchanged by the patient's respiratory system. Measures of ventilation may include one or both of inspiratory and expiratory flow, per unit time. When expressed as a volume per minute, this quantity is often referred to as "minute ventilation". Minute ventilation is sometimes given simply as a volume, understood to be the volume per minute.

5.8.3 Anatomy 5.8.3.1 Anatomy of the Face

Ala: the external outer wall or "wing" of each nostril (plural: alar)

Alare: The most lateral point on the nasal ala.

Alar curvature (or alar crest) point: The most posterior point in the curved base line of each ala, found in the crease formed by the union of the ala with the cheek.

Auricle: The whole external visible part of the ear.

(nose) Bony framework: The bony framework of the nose comprises the nasal bones, the frontal process of the maxillae and the nasal part of the frontal bone.

(nose) Cartilaginous framework: The cartilaginous framework of the nose comprises the septal, lateral, major and minor cartilages.

Columella: the strip of skin that separates the nares and which runs from the pronasale to the upper lip.

Columella angle: The angle between the line drawn through the midpoint of the nostril aperture and a line drawn perpendicular to the Frankfort horizontal while intersecting subnasale.

Frankfort horizontal plane: A line extending from the most inferior point of the orbital margin to the left tragion. The tragion is the deepest point in the notch superior to the tragus of the auricle.

*Glabella*: Located on the soft tissue, the most prominent point in the midsagittal plane of the forehead.

Lateral nasal cartilage: A generally triangular plate of cartilage. Its superior margin is attached to the nasal bone and frontal process of the maxilla, and its inferior margin is connected to the greater alar cartilage.

Greater alar cartilage: A plate of cartilage lying below the lateral nasal cartilage. It is curved around the anterior part of the naris. Its posterior end is connected to the frontal process of the maxilla by a tough fibrous membrane containing three or four minor cartilages of the ala.

Nares (Nostrils): Approximately ellipsoidal apertures forming the entrance to the nasal cavity. The singular form of nares is naris (nostril). The nares are separated by the nasal septum.

Naso-labial sulcus or Naso-labial fold: The skin fold or groove that runs from each side of the nose to the corners of the mouth, separating the cheeks from the upper lip.

Naso-labial angle: The angle between the columella and the upper lip, while intersecting subnasale.

Otobasion inferior: The lowest point of attachment of the auricle to the skin of the face.

Otobasion superior: The highest point of attachment of the auricle to the skin of the face.

Pronasale: the most protruded point or tip of the nose, which can be identified in lateral view of the rest of the portion of the head.

Philtrum: the midline groove that runs from lower border of the nasal septum to the top of the lip in the upper lip region.

Pogonion: Located on the soft tissue, the most anterior midpoint of the chin.

Ridge (nasal): The nasal ridge is the midline prominence of the nose, extending from the Sellion to the Pronasale.

Sagittal plane: A vertical plane that passes from anterior (front) to posterior (rear). The midsagittal plane is a sagittal plane that divides the body into right and left halves.

Sellion: Located on the soft tissue, the most concave point overlying the area of the frontonasal suture.

Septal cartilage (nasal): The nasal septal cartilage forms part of the septum and divides the front part of the nasal cavity.

Subalare: The point at the lower margin of the alar base, where the alar base joins with the skin of the superior (upper) lip.

Subnasal point: Located on the soft tissue, the point at which the columella merges with the upper lip in the midsagittal plane.

Supramenton: The point of greatest concavity in the midline of the lower lip between labrale inferius and soft tissue pogonion 5.8.3.2 Anatomy of the Skull Frontal bone: The frontal bone includes a large vertical portion, the squama *frontalis*, corresponding to the region known as the forehead.

Mandible: The mandible forms the lower jaw. The mental protuberance is the bony protuberance of the jaw that forms the chin.

Maxilla: The maxilla forms the upper jaw and is located above the mandible and below the orbits. The frontal process of the maxilla projects upwards by the side of the nose, and forms part of its lateral boundary.

Nasal bones: The nasal bones are two small oblong bones, varying in size and form in different individuals; they are placed side by side at the middle and upper part of the face, and form, by their junction, the "bridge" of the nose.

Nasion: The intersection of the frontal bone and the two nasal bones, a depressed area directly between the eyes and superior to the bridge of the nose.

Occipital bone: The occipital bone is situated at the back and lower part of the cranium. It includes an oval aperture, the foramen magnum, through which the cranial cavity communicates with the vertebral canal. The curved plate behind the foramen magnum is the squama occipitalis.

Orbit: The bony cavity in the skull to contain the eyeball.

Parietal bones: The parietal bones are the bones that, when joined together, form the roof and sides of the cranium.

Temporal bones: The temporal bones are situated on the bases and sides of the skull, and support that part of the face known as the temple.

Zygomatic bones: The face includes two zygomatic bones, located in the upper and lateral parts of the face and forming the prominence of the cheek.

5.8.3.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.8.4 Patient Interface

Anti-asphyxia valve (AAV): The component or sub-assembly of a mask system that, by opening to atmosphere in a failsafe manner, reduces the risk of excessive $CO_2$ rebreathing by a patient.

Elbow: An elbow is an example of a structure that directs an axis of flow of air travelling therethrough to change direction through an angle. In one form, the angle may be approximately 90 degrees. In another form, the angle may be more, or less than 90 degrees. The elbow may have an approximately circular cross-section. In another form the elbow may have an oval or a rectangular cross-section. In certain forms an elbow may be rotatable with respect to a mating component, e.g. about 360 degrees. In certain forms an elbow may be removable from a mating component, e.g. via a snap connection. In certain forms, an elbow may be assembled to a mating component via a one-time snap during manufacture, but not removable by a patient.

Frame: Frame will be taken to mean a mask structure that bears the load of tension between two or more points of connection with a headgear. A mask frame may be a non-airtight load bearing structure in the mask. However, some forms of mask frame may also be air-tight.

Headgear. Headgear will be taken to mean a form of positioning and stabilising structure designed for use on a head. For example the headgear may comprise a collection of one or more struts, ties and stiffeners configured to locate and retain a facial interface (e.g., a patient interface) in position on a patient's face for delivery of respiratory therapy. Some ties are formed of a soft, flexible, elastic material such as a laminated composite of foam and fabric.

Membrane: Membrane will be taken to mean a typically thin element that has, preferably, substantially no resistance to bending, but has resistance to being stretched.

Plenum chamber: a mask plenum chamber will be taken to mean a portion of a patient interface having walls at least partially enclosing a volume of space, the volume having air therein pressurised above atmospheric pressure in use. A shell may form part of the walls of a mask plenum chamber.

Seal: May be a noun form ("a seal") which refers to a structure, or a verb form ("to seal") which refers to the effect. Two elements may be constructed and/or arranged to 'seal' or to effect 'sealing' therebetween without requiring a separate 'seal' element per se.

Shell: A shell will be taken to mean a curved, relatively thin structure having bending, tensile and compressive stiffness. For example, a curved structural wall of a mask may be a shell. In some forms, a shell may be faceted. In some forms a shell may be airtight. In some forms a shell may not be airtight.

Stiffener: A stiffener will be taken to mean a structural component designed to increase the bending resistance of another component in at least one direction.

Strut: A strut will be taken to be a structural component designed to increase the compression resistance of another component in at least one direction.

Swivel (noun): A subassembly of components configured to rotate about a common axis, preferably independently, preferably under low torque. In one form, the swivel may be constructed to rotate through an angle of at least 360 degrees. In another form, the swivel may be constructed to rotate through an angle less than 360 degrees. When used in the context of an air delivery conduit, the sub-assembly of components preferably comprises a matched pair of cylindrical conduits. There may be little or no leak flow of air from the swivel in use.

Tie (noun): A structure designed to resist tension.

Vent: (noun): A structure that allows a flow of air from an interior of the mask, or conduit, to ambient air for clinically effective washout of exhaled gases. For example, a clinically effective washout may involve a flow rate of about 10 litres per minute to about 100 litres per minute, depending on the mask design and treatment pressure.

5.8.5 Shape of Structures

Products in accordance with the present technology may comprise one or more three-dimensional mechanical structures, for example a mask cushion or an impeller. The three-dimensional structures may be bounded by two-dimensional surfaces. These surfaces may be distinguished using a label to describe an associated surface orientation, location, function, or some other characteristic. For example a structure may comprise one or more of an anterior surface, a posterior surface, an interior surface and an exterior surface. In another example, a seal-forming structure may comprise a face-contacting (e.g. outer) surface, and a separate non-face-contacting (e.g. underside or inner) surface. In another example, a structure may comprise a first surface and a second surface.

To facilitate describing the shape of the three-dimensional structures and the surfaces, we first consider a cross-section through a surface of the structure at a point, p. See FIG. 3B to FIG. 3F, which illustrate examples of cross-sections at point p on a surface, and the resulting plane curves. FIGS. 3B to 3F also illustrate an outward normal vector at p. The outward normal vector at p points away from the surface. In some examples we describe the surface from the point of view of an imaginary small person standing upright on the surface.

5.8.5.1 Curvature in One Dimension

The curvature of a plane curve at p may be described as having a sign (e.g. positive, negative) and a magnitude (e.g. 1/radius of a circle that just touches the curve at p).

Positive curvature: If the curve at p turns towards the outward normal, the curvature at that point will be taken to be positive (if the imaginary small person leaves the point p they must walk uphill). See FIG. 3B (relatively large positive curvature compared to FIG. 3C) and FIG. 3C (relatively small positive curvature compared to FIG. 3B). Such curves are often referred to as concave.

Zero curvature: If the curve at p is a straight line, the curvature will be taken to be zero (if the imaginary small person leaves the point p, they can walk on a level, neither up nor down). See FIG. 3D.

Negative curvature: If the curve at p turns away from the outward normal, the curvature in that direction at that point will be taken to be negative (if the imaginary small person leaves the point p they must walk downhill). See FIG. 3E (relatively small negative curvature compared to FIG. 3F) and FIG. 3F (relatively large negative curvature compared to FIG. 3E). Such curves are often referred to as convex.

5.8.5.2 Curvature of Two Dimensional Surfaces

A description of the shape at a given point on a two-dimensional surface in accordance with the present technology may include multiple normal cross-sections. The multiple cross-sections may cut the surface in a plane that includes the outward normal (a "normal plane"), and each cross-section may be taken in a different direction. Each cross-section results in a plane curve with a corresponding curvature. The different curvatures at that point may have the same sign, or a different sign. Each of the curvatures at that point has a magnitude, e.g. relatively small. The plane curves in FIGS. 3B to 3F could be examples of such multiple cross-sections at a particular point.

Principal curvatures and directions: The directions of the normal planes where the curvature of the curve takes its maximum and minimum values are called the principal directions. In the examples of FIG. 3B to FIG. 3F, the maximum curvature occurs in FIG. 3B, and the minimum occurs in FIG. 3F, hence FIG. 3B and FIG. 3F are cross sections in the principal directions. The principal curvatures at p are the curvatures in the principal directions.

Region of a surface: A connected set of points on a surface. The set of points in a region may have similar characteristics, e.g. curvatures or signs.

Saddle region: A region where at each point, the principal curvatures have opposite signs, that is, one is positive, and the other is negative (depending on the direction to which the imaginary person turns, they may walk uphill or downhill).

Dome region: A region where at each point the principal curvatures have the same sign, e.g. both positive (a "concave dome") or both negative (a "convex dome").

Cylindrical region: A region where one principal curvature is zero (or, for example, zero within manufacturing tolerances) and the other principal curvature is non-zero.

Planar region: A region of a surface where both of the principal curvatures are zero (or, for example, zero within manufacturing tolerances).

Edge of a surface: A boundary or limit of a surface or region.

Path: In certain forms of the present technology, 'path' will be taken to mean a path in the mathematical—topological sense, e.g. a continuous space curve from f(0) to f(1) on a surface. In certain forms of the present technology, a 'path' may be described as a route or course, including e.g. a set of points on a surface. (The path for the imaginary person is where they walk on the surface, and is analogous to a garden path).

Path length: In certain forms of the present technology, 'path length' will be taken to mean the distance along the surface from f(0) to f(1), that is, the distance along the path on the surface. There may be more than one path between two points on a surface and such paths may have different path lengths. (The path length for the imaginary person would be the distance they have to walk on the surface along the path).

Straight-line distance: The straight-line distance is the distance between two points on a surface, but without regard to the surface. On planar regions, there would be a path on the surface having the same path length as the straight-line distance between two points on the surface. On non-planar surfaces, there may be no paths having the same path length as the straight-line distance between two points. (For the imaginary person, the straight-line distance would correspond to the distance 'as the crow flies'.)

5.8.5.3 Space Curves

Space curves: Unlike a plane curve, a space curve does not necessarily lie in any particular plane. A space curve may be closed, that is, having no endpoints. A space curve may be considered to be a one-dimensional piece of three-dimensional space. An imaginary person walking on a strand of the DNA helix walks along a space curve. A typical human left ear comprises a helix, which is a left-hand helix, see FIG. 3Q. A typical human right ear comprises a helix, which is a right-hand helix, see FIG. 3R. FIG. 3S shows a right-hand helix. The edge of a structure, e.g. the edge of a membrane or impeller, may follow a space curve. In general, a space curve may be described by a curvature and a torsion at each point on the space curve. Torsion is a measure of how the curve turns out of a plane. Torsion has a sign and a magnitude. The torsion at a point on a space curve may be characterised with reference to the tangent, normal and binormal vectors at that point.

Tangent unit vector (or unit tangent vector): For each point on a curve, a vector at the point specifies a direction from that point, as well as a magnitude. A tangent unit vector is a unit vector pointing in the same direction as the curve at that point. If an imaginary person were flying along the curve and fell off her vehicle at a particular point, the direction of the tangent vector is the direction she would be travelling.

Unit normal vector: As the imaginary person moves along the curve, this tangent vector itself changes. The unit vector pointing in the same direction that the tangent vector is changing is called the unit principal normal vector. It is perpendicular to the tangent vector.

Binormal unit vector: The binormal unit vector is perpendicular to both the tangent vector and the principal normal vector. Its direction may be determined by a right-hand rule (see e.g. FIG. 3P), or alternatively by a left-hand rule (FIG. 3O).

Osculating plane: The plane containing the unit tangent vector and the unit principal normal vector. See FIGS. 3O and 3P.

Torsion of a space curve: The torsion at a point of a space curve is the magnitude of the rate of change of the binormal unit vector at that point. It measures how much the curve deviates from the osculating plane. A space curve which lies in a plane has zero torsion. A space curve which deviates a relatively small amount from the osculating plane will have a relatively small magnitude of torsion (e.g. a gently sloping helical path). A space curve which deviates a relatively large amount from the osculating plane will have a relatively large magnitude of torsion (e.g. a steeply sloping helical path). With reference to FIG. 3S, since T2>T1, the magnitude of the torsion near the top coils of the helix of FIG. 3S is greater than the magnitude of the torsion of the bottom coils of the helix of FIG. 3S With reference to the right-hand rule of FIG. 3P, a space curve turning towards the direction of the right-hand binormal may be considered as having a right-hand positive torsion (e.g. a right-hand helix as shown in FIG. 3S). A space curve turning away from the direction of the right-hand binormal may be considered as having a right-hand negative torsion (e.g. a left-hand helix).

Equivalently, and with reference to a left-hand rule (see FIG. 3O), a space curve turning towards the direction of the left-hand binormal may be considered as having a left-hand positive torsion (e.g. a left-hand helix). Hence left-hand positive is equivalent to right-hand negative. See FIG. 3T.

5.8.5.4 Holes

A surface may have a one-dimensional hole, e.g. a hole bounded by a plane curve or by a space curve. Thin structures (e.g. a membrane) with a hole, may be described as having a one-dimensional hole. See for example the one dimensional hole in the surface of structure shown in FIG. 3I, bounded by a plane curve.

A structure may have a two-dimensional hole, e.g. a hole bounded by a surface. For example, an inflatable tyre has a two dimensional hole bounded by the interior surface of the tyre. In another example, a bladder with a cavity for air or gel could have a two-dimensional hole. See for example the cushion of FIG. 3L and the example cross-sections therethrough in FIG. 3M and FIG. 3N, with the interior surface bounding a two dimensional hole indicated. In a yet another example, a conduit may comprise a one-dimension hole (e.g. at its entrance or at its exit), and a two-dimension hole bounded by the inside surface of the conduit. See also the two dimensional hole through the structure shown in FIG. 3K, bounded by a surface as shown.

5.9 Other Remarks

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Furthermore, "approximately", "substantially", "about", or any similar term as used herein means +/−5 to +/−10% of the recited value.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being used to construct a component, obvious alternative materials with similar properties may be used as a substitute. Furthermore, unless specified to the contrary, any and all components herein described are understood to be capable of being manufactured and, as such, may be manufactured together or separately.

It must be noted that as used herein and in the appended claims, the singular forms "a", "an", and "the" include their plural equivalents, unless the context clearly dictates otherwise.

All publications mentioned herein are incorporated herein by reference in their entirety to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

The terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular examples, it is to be understood that these examples are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative examples and that other arrangements may be devised without departing from the spirit and scope of the technology.

5.10 REFERENCE SIGNS LIST

| | |
|---|---|
| patient | 1000 |
| bed partner | 1100 |
| patient interface | 3000 |
| seal - forming structure | 3100 |
| plenum chamber | 3200 |
| orifice | 3202 |
| chord | 3210 |
| projection | 3212 |
| superior point | 3220 |
| inferior point | 3230 |
| structure | 3300 |
| headgear assembly | 3302 |
| sleeve | 3304 |
| first portion | 3304a |
| second portion | 3304b |
| single rigidized arm | 3306 |
| rigidized arm | 3306 |
| cavity | 3308 |
| first rear section | 3310a |
| second rear section | 3310b |
| fastener | 3312 |
| opening | 3315 |
| plug | 3316 |
| body | 3320 |
| first body portion | 3320a |
| second body portion | 3320b |
| aperture | 3324 |
| arm portion | 3328 |
| end | 3329 |
| free end | 3330 |
| inner coupling | 3334 |
| outer coupling | 3338 |
| free end | 3342 |
| projections | 3346 |
| axis | 3348 |
| cover | 3354 |
| fluid conduit | 3358 |
| inlet | 3362 |
| rear strap | 3366 |
| tabs | 3370 |
| vent | 3400 |
| connection port | 3600 |
| forehead support | 3700 |
| ISO | 3744 |
| RPT device | 4000 |
| external housing | 4010 |
| upper portion | 4012 |
| portion | 4014 |
| panel | 4015 |
| chassis | 4016 |
| handle | 4018 |
| pneumatic block | 4020 |
| air filter | 4110 |
| inlet air filter | 4112 |
| outlet air filter | 4114 |
| muffler | 4120 |
| inlet muffler | 4122 |
| outlet muffler | 4124 |
| pressure generator | 4140 |
| blower | 4142 |
| motor | 4144 |
| anti - spill back valve | 4160 |
| air circuit | 4170 |
| ring | 4171 |
| supplementary gas | 4180 |
| electrical components | 4200 |
| single Printed Circuit Board Assembly PCBA | 4202 |
| power supply | 4210 |
| input device | 4220 |
| transducer | 4270 |
| humidifier | 5000 |

What is claimed is:

1. A patient interface comprising:
a plenum chamber pressurisable to a therapeutic pressure of at least 6 cmH2O above ambient air pressure, said plenum chamber including a plenum chamber inlet port sized and structured to receive a flow of air at the therapeutic pressure for breathing by a patient;
a seal-forming structure constructed and arranged to form a seal with a region of the patient's face surrounding an entrance to the patient's airways, said seal forming structure having a hole therein such that the flow of air at said therapeutic pressure is delivered to at least an entrance to the patient's nares, the seal-forming structure constructed and arranged to maintain said therapeutic pressure in the plenum chamber throughout the patient's respiratory cycle in use; and
a positioning and stabilising structure to provide a force to hold a seal forming structure in a therapeutically effective position on the patient's head, the positioning and stabilising structure comprising:
at least one rigidized arm configured, in use, to be positioned adjacent to a cheek of the patient; and
a strap removably received around the rigidized arm and configured to contact, in use, a posterior region of the patient's head, the strap comprising,
a first rigid coupling forming an opening to a cavity, the rigidized arm being positionable through the opening and into the cavity, the first rigid coupling having a mechanical connector that is configured to engage the rigidized arm and limit movement of the rigidized arm into and out of the cavity,
a second rigid coupling spaced apart from an outer surface of the first rigid coupling, and
a sleeve constructed from a flexible material, the sleeve being folded over the second rigid coupling and positioned between the first rigid coupling and the second rigid coupling.

2. The patient interface of claim 1, wherein the sleeve includes an outer surface that comprises an outermost surface of the strap, and an inner surface that comprises a boundary of the cavity.

3. The patient interface of claim 1, wherein the mechanical connector of the first rigid coupling includes a projection, and the rigidized arm includes a recess configured to receive the projection.

4. The patient interface of claim 3, wherein the projection extends at an angle between 40° and 60° from an inner surface of the first rigid coupling, the angle measured with respect to an axis that is parallel to a radial axis of the first rigid coupling.

5. The patient interface of claim 1, wherein the mechanical connector comprises a snap-fit connection.

6. The patient interface of claim 1, wherein the flexible material is a textile.

7. The patient interface of claim 1, wherein the flexible material is elastic and/or elastomeric.

8. The patient interface of claim 1, wherein the first rigid coupling and the second rigid coupling have a generally circular shape, the rigidized arm further including an extension having at least a portion of the generally circular shape.

9. The patient interface of claim 1, wherein the rigidized arm is configured to not extend in a posterior direction further than the patient's ear.

10. The patient interface of claim 1, wherein the strap includes a first piece and a second piece coupled together using a length adjuster, wherein the length adjuster is configured to change a usable length of the strap.

11. The patient interface of claim 1, wherein the strap is bifurcated.

12. The patient interface of claim 1, wherein;
the at least one rigidized arm comprises a first rigidized arm configured, in use, to be positioned on a left side of the patient's head,
a second rigidized arm coupled to the positioning and stabilising structure and configured, in use, to be positioned adjacent to a right cheek of the patient, and the strap is removably received around the second rigidized arm, the strap comprising:
a third rigid coupling defining a second opening to the cavity, the second rigidized arm being positionable through the second opening and into the cavity, the third rigid coupling having a mechanical connector that engages the second rigidized arm and limits movement of the second rigidized arm into and out of the second opening of the cavity,
a fourth rigid coupling spaced apart from an outer surface of the first rigid coupling, and
the sleeve being folded over the fourth rigid coupling and positioned between the third rigid coupling and the fourth rigid coupling.

13. The patient interface of claim 1, wherein the plenum chamber inlet port is a first plenum chamber inlet port, the plenum chamber further includes a second plenum chamber inlet port, the first plenum chamber inlet port configured to receive the flow of air at the therapeutic pressure, and the second plenum chamber inlet port configured to receive a plug configured to prevent the flow of air at the therapeutic pressure from escaping.

14. The patient interface of claim 13, wherein the rigidized arm includes the plug.

15. The patient interface of claim 13, wherein the plug is removable from the second opening in order to permit pressurized air to flow through the second opening.

16. The patient interface of claim 1, wherein the rigidized arm is at least partially flexible in order to adjust a contour to substantially correspond to the cheek of the patient.

17. The patient interface of claim 1, wherein the seal forming structure defines nasal pillows or a cradle.

18. The patient interface of claim 1, wherein the first rigid coupling, the second rigid coupling, and the sleeve are coupled together using an adhesive.

19. The patient interface of claim 1, wherein the cavity includes a width less than a width of the rigidized arm, and wherein the sleeve is configured to stretch upon receiving the rigidized arm.

20. A method of manufacturing the patient interface of claim 1, the method comprising forming the strap by:
providing the flexible material;
inserting the second coupling into the cavity of the flexible material; folding an end of the flexible material into the cavity to enclose the second coupling; and
inserting the first coupling into the cavity.

21. The method of claim 20, the method further comprising the steps of connecting the positioning and stabilising structure to the seal-forming structure by:
providing a plenum chamber with a connection opening; and
inserting a plug of the rigidized arm into the connection opening.

22. The method of claim 21, the method further comprising applying an adhesive around the connection opening in order to secure the plug within the opening.

23. The method of claim 21, the method further comprising removing the plug from the connection opening.

* * * * *